(12) United States Patent
Koltin et al.

(10) Patent No.: US 6,280,963 B1
(45) Date of Patent: Aug. 28, 2001

(54) ESSENTIAL FUNGAL GENES AND THEIR USE

(75) Inventors: Yigal Koltin, Newton; Victoria Gavrias, Upton, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/965,762

(22) Filed: Nov. 7, 1997

(51) Int. Cl.$^7$ ............... G01N 33/53; C12Q 1/68; C07H 21/04
(52) U.S. Cl. ............ 435/7.31; 435/6; 435/320.1; 435/254.3; 530/350; 536/23.1; 536/24.5; 536/23.4
(58) Field of Search .................. 536/23.1, 23.4, 536/245; 435/6, 320.1, 419, 254.3; 530/350

(56) References Cited

FOREIGN PATENT DOCUMENTS

| WO 95/06132 | 3/1995 | (WO) | ............... C12Q/1/02 |
| WO 95/10625 | 4/1995 | (WO) | ............... C12P/1/04 |
| WO 97/42210 | 11/1997 | (WO) | ............... C07H/21/04 |

OTHER PUBLICATIONS

Du, database PIR2, Accession # S59791, Jan. 13, 1996.*
Savitt et al., database PIR2, Accession # 150712, Sep. 13, 1996.*
New England Biolabs Catalog, pp. 60–62, 86/87.*
Berendsen, A glimpse of the holy grail, Science, vol. 282, pp. 642–643, Oct. 1998.*
Tuite; "Discovery and development of new systemic antifungals"; *Tibtech*, vol. 14; pp. 219–220; Jul. 1996.
Topczewski et al.; "Cloning and characterization of the *Aspergillus nidulans* cysB gene encoding cysteine synthase"; *Current Genet.*, vol. 31; pp. 348–356; 1997—XP002109934.
Doshi et al.; "Two α-tubulin genes of *Aspergillus nidulans* encode divergent proteins"; *Mol. Gen. Genet.*, vol. 225; pp. 129–141; 1991—XP002109954.
Yanai et al.; "Isolation and Characterization of Two Chitin Synthase Genes from *Aspergillus nidulans*"; *Biosc. Biotech. Biochem.*, vol. 58; pp. 1828–1835; 1994—XP002109955.
Tuite; "Antifungal drug development: the identification of new targets"; *Trends in Biotechnology*, vol. 10, No. 7; pp. 219–220; Jul. 1, 1996—XP004035757.

* cited by examiner

*Primary Examiner*—Andrew Wang
(74) *Attorney, Agent, or Firm*—Fish & Richardson P.C.

(57) ABSTRACT

Disclosed are essential Aspergillus polypeptides and genes (AN97, AN17, AN80, and AN85), as well as homologs of, which can be used to identify antifungal agents for treating fungal infections such as aspergillosis.

24 Claims, 46 Drawing Sheets

(SEQ ID NO:1)
1    AGGCTGCGCAGGGCAGCTGTGGCAATATGCCGACGCTTTGGCGACGCTGTCCTGAAACAGAAAAGACAAGACGAAGT
     TCGCGACGGTCCCGTCGACACCGTTAGCGGCCTGCGAAACCGCTTTGTGTCTTTTCTGTTCTGCTTCA
(SEQ ID NO:3)

101  TCCCCGATTGTATCTGAATGAGGGACCGATTTCCGGCGGTTAGTAGAGGTCACGTGTAAGATGCGTGCTAACTAGTATGCAAGGCATTTCGGCTCA
     AGGGGCCTAACATAGAGCTTACTACTCCCCTGGCTAAAGCCGCCAATCATTCTCCAGTGCACTTTCTACCGCACGATTGATCATACGTTCCGTAAGCCGAGT

201  GGCAAATACCCAGTCAACAATTGTTGCCTGGAGTGGAAATACGAGAACACCTCCACCCTTTGATTGCGAGCAGTGTGTGATTAGGATAGCTGAGGCATTGTATTCAT
     CCGTTTTATGGGTCAGTTGTTAAACAACGGACCCTCACCTTTATGCTCTCTTGGGAACTAACGCTCGTATCCTATGGACTCCGTAACATAAGTA

301  GTATCAGGAACCTGATCGTCAAAGGCGTTGCAGGCTGCTCAGGGCTGCTGCCCTAACCCTTATCTATCTACTGGTTGTTTGTTTATGCT
     CATAGTCCTTGACTAGCAGTTTCGCAACGTCCGACCCGTGCACCGACGGGATTGGAATAGATAGATGACCAAACCCACAACAATACGA

401  CCGCCCCGTGACTCTCAGCAACGGTTATAACGAGTAGTGCAGCAGCCAACAACTTCTTTGCTGCCGACCTCACGCCAAACAAAGCCTTTACTGAAA
     GGCGGGGCACTGAGAGTCGTGCCAATATTGCTCATCACCGTCGGTTGCTTGGAGTGCGGTTGTTTCGGAAATGACCTTT

501  CAGGCTGATCAGCAAATCAAGATATACTAGGATGAGTTGATATTATCACCGGCCGCAGATTACTGACCGGCCAGACCCTTACTGCTCATTACCCCTCGATC
     GTCCGACTAGTCGTTAGTTCTATATGATCCTACTCAACTATATAATAGTGGCCGGCGTCTAATGACTGGGCTGTGGGAATGACGCAGTAATGGGGAGCTAG

FIG. 1A

```
601  AAGATGCCGAGTCGAGTTTCCGCCCGTTCAACATCCACCGTTGCGCCTCGGCGCAAAGGCTTCTACACAGACTGCGACAAGCGGTCGCGCTCGGCTCAGGACCCCAT    700
     TTCTACGGCTCAGCTCAAGGCGGGCAAGTTGTAGGTGCGGAGCGCGTTCGAGATGTGTCTGACGCTGTTCGCCAGCGCGAGTCGCGTGGGTA
1    M   P   S   R   V   S   A   R   S   T   S   T   A   S   R   K   G   S   T   Q   T   A   T   S   G   R   A   G   S   A   T   P   S    33
                                                                                                                       (SEQ ID NO:2)

701  CATTCGCCATCCCAGAGAGAAACTGCATTACCCGAGGCTGTTCCAACCCTTGCGCCGGATGTATGCCCATTTTCGCGGATCGTTGACTGCCGG    800
     GTAAGCGGTAGGGTCTCTCTTTGACGTAATGGGCTCCGACAAGGTTGGAAGCGGCTACATACGCGGTAAAGCGCCTAGCAACTGACGGCC
34   F   A   I   P   E   E   T   A   L   P   E   A   V   P   T   L   R   R   D   V   C   A   I   F   A   D   A   Q   R   S   T   A   G    66

801  TCATCGCAAACTTGTCGTCCGACTAAGGAAATCCAGGAGGTGTGCTGTGCTATACCCCAGAAGAACTCCAAAAAGACAGTTCAACTGAAGAGCGATTG    900
     AGTAGCGTTTGAACAGCAGCCTGATTCCTTTAGGTCCTCCACACGACACGATATGGGGTCTTCTTGAGTTTTCGTCAAGTTGACTTCTCGCTAAC
67   H   R   K   L   V   V   R   L   R   K   I   Q   E   V   C   C   A   I   P   Q   K   N   S   K   K   D   S   T   E   E   R   L    99

901  ATTCCCGGCGAAGAGACGGTACCAGAAAAGGAGTTCAACGTCGAAGTAGTCGAAGTTCAAGTCGAGCATCTTGTCTATTAAGAAGACAGAGCCTGTTGGCG    1000
     TAAGGGCCGCTTCTCTGCCATGGTCTTTTCCTCAAGTTGCAGCTTCATTCAGCAACACAGCGTAGAACAGATAATTCTTCTGTCTCCGACAACCGC
100  I   P   G   E   E   T   V   P   E   K   E   F   N   V   E   V   S   R   C   V   L   R   I   L   S   I   K   K   T   E   P   V   G   D    133

1001 ATCGAATCCTGCGGTTCTGGGAACTTCCTACTCATGCCTCGGAAATCTTCGGCTCTGAGATCTTCGGCTCTGAAGAAGACGATATGCAGAATTC    1100
     TAGCTTAGGACGCCAAAGACCCTTGAAGGATGAGTACGGAGCCTTTCGACTGAGTCTAGAAGCCGAGACTTCTGCTACTTCTGTATACGTCTTAAG
134  R   I   L   R   F   L   G   N   F   L   T   H   A   S   E   K   D   A   E   I   F   G   S   E   E   D   D   M   Q   N   S    166
```

FIG. 1B

```
1101  GCACGAAAGACCGACTGCCCACTGACCACAGTCTTGTCTGTCTGCAAAGACAAGTTGTGCGCTTCCGTACCACGCAA  1200
      CGTGCTTTCTGGCTGACGGGTGAACTGGTGGTCAGACAGAGGACAATCACGGAAACACAGACGTTTCTGTTCCAACACGTTGCGTT
167    H  E  R  P  T  A  H  L  T  T  S  L  V  S  L  L  V  P  L  L  S  A  K  D  K  V  V  R  F  R  T  T  Q    199

1201  ATTATCGCGCACATCGTCAATTCACTCGATACCGTAGACGACGAATTATACCACACTCTCCGGCAAGCCTTCTAAAACGATTCGCGACAAGAACCTT  1300
      TAATAGCGCGTGTAGCAGTTAAGTGAGCTATGGCATCTGCTTAATATGGTGTGAGAGGCCGTTCGGAAGATTTTGCTAAGCGCTGTTTCTTGGAA
200    I  I  A  H  I  V  N  S  L  D  T  V  D  D  E  L  Y  H  T  L  R  Q  G  L  L  K  R  I  R  D  K  E  P  S    233

1301  CGGTGCGGGTACAAGCAGTGATGGGTCTCGGCCGCCTTGTGCCCTTGTGAGAAGCTCGT  1400
      GCCACGCCCATGTTCGTCACTACCCAGAGCCGGCGGAACGGGTTCGCGGAACACCTCTCGAGCA
234    V  R  V  Q  A  V  M  G  L  G  R  L  A  G  N  E  E  D  D  D  E  N  D  D  T  S  A  L  V  E  K  L  V    266

1401  GGACATAATGCAAAATGACACGGCTGCAGAGGTTCGGAGAGACATTACTCCTCAACCTCCCATTGATTCGTCTACCCTTCCTATACCTCCTCGAACGCGCC  1500
      CCTGTATTACGTTTTACTGTGCCGACGTCTCCAAGCCTCTGTAATGAGGAGTTGGAGGGTAACTAAGCAGATGGAAGTATGGAGAGCTGCGCGG
267    D  I  M  Q  N  D  T  A  A  E  V  R  R  T  L  L  N  L  P  L  I  P  S  T  L  P  Y  L  L  E  R  A    299
```

FIG. 1C

| | | |
|---|---|---|
| 1501 | CGTGACCTGGATGCTCCCACGAAGGGCATTATATTCTCGTCTACTTCGTCTACTTCGACACTGGAGATTTCCGACACTTATCTCTCCATGAGAGAAAGTTGC<br>GCACTGGAGCTACGAGGGTGTCCCGGTGTGTCCCTTCCGGTGACCCTCTAAAGCTGTGACCCTCTAAAGCTGTAATAGAGAGGTACTCTCTTTCAACG | 1600 |
| 300 | R D L D A P T R R A L Y S R L L P T L G D F R H L S L S M R E K L L | 333 |
| 1601 | TCAGATGGGTCTTCGTGATCGCAACAAAAGTGTGAGGAAGGCCACTGAAAGTTGTTCTATGACCGCTGATTGAGATATCGCTGGACGAACAATGAC<br>AGTCTACCCAGAAGCACTAGGCGCTGTTTTCACACTGCTTCCGTGACCTTCAACAGATACTGCGACTAACTCTATAGCGACCTGCTTGTTACTG | 1700 |
| 334 | R W G L R D R D K S V R K A T G K L F Y D R W I E I S L A R T M T | 366 |
| 1701 | CCTGAGAATTCGGGCAGCGCTCGGAACGAGAATTCCCGCTTTACTGAGTGTGTTGGAGCGTATCGATGTGGTGAACTCAGGCATGAATCCGGCATAGCG<br>GGACTCTTAAGCCCGTCGCGAGCCGTCCTTGCTCTTAAGGGCGAAATGACTCACAACCTGCATAGCTACACACCACTTGAGTCCGTACCTAGGCCGTATGC | 1800 |
| 367 | L R I R A A L G T R I P A L L E L L E R I D V V N S G M E S G I A | 399 |
| 1801 | CACGAAGCTATGCGACAGTTTCTGGGAAGTCGACCAGACTATCGAGAGAGGCGGTACTATTCGACGAAGCCTTCGGAGTCAATGACACGCAGAATCCGCTT<br>GTGCTTCGATACGCTGTCAAAGACCCTTCAGCTGGTCTGATAGCTCTCCGCCATGATAAGCTGCTTCGGAAGCACCCTCAGTTACTGTCGTCTTAGGCGAA | 1900 |
| 400 | H E A M R S F W E G R P D Y R E A V L F D E A F W E S M T A E S A F | 433 |
| 1901 | TCCTCCTTCGCTCATTCAATGACTTTTGCCGGGTTGAAAACGAAGGTAAATATGACAGCCTCGCCGATGAGAAGATCCAGTCGTTACGCCCTCGCAAT<br>AGGAGGAAGCGAGTAAGTTACTGAAAACGGCCCAACTTTGCTCCATTTATACTGTCGGAGCGGCTACTCTTCTAGGTGCAGCAATGTCGGAGCGTTA | 2000 |
| 434 | L L R S F N D F C R V E N E G K Y D S L A D E K I P V V T A L A M | 466 |

FIG. 1D

```
2001  GTATCTTCATAAGTACACATGACCGAGCTTCTGCAGCGCCAAGAAGCTCACAAAGGATGCTACTGACGTAAACGACGACGATACCGTCGAAATCGAATTTATC  2100
      CATAGAAGTATTCATGTGTACTGGCTCGAAGACGTCGCGTTCTTCGAGTGTTTCCTACGATGACTGCATTGCTGCTGCTATGGCAGCTTTAGCTTAAATAG
467    Y  L  H  K  Y  M  T  E  L  L  Q  R  K  K  L  T  K  D  A  T  D  V  N  D  D  D  T  V  E  I  E  F  I      499

2101  GTCGAGCAACTGCTTCACATCGCGATGACACTAGACTACAGCGACGAAGTTGGGCGACGAAGTTTTCTCTACTCCGTGAGGCTCTCGCTGTCCCAG       2200
      CAGCTCGTTGACGAAGTGTAGCGCTACTGTGATCTGATGTCGCTGCTTCAACCCGCGCTTCTACAAAGAGATGAGGCACTCCGAGACGACGAGGTC
500    V  E  Q  L  L  H  I  A  M  T  L  D  Y  S  D  E  V  G  R  R  K  M  F  S  L  L  R  E  A  L  A  V  P  E   533

2201  AGCTCCCTCAGGAATCGACCAAGCTCGCGGTTGAGACACTGAGACTTCTGAGGCCCGAGCGCCGACGCCAGAGAGCGAATTCTCAGTGTGTTCTCTGA     2300
      TCGAGGGAGTCCTTAGCTGGTTCGAGCGCCAACTCTGTGACTCTGAAGACGTCACACAACACCCGGGCTGCGGCGCGTCTCGCTTAAGACGTCACAAGACCT
534    L  P  Q  E  S  T  K  L  A  V  E  T  L  R  C  V  C  G  P  D  A  A  A  E  S  E  F  C  S  V  V  L  E      566

2301  AGCCATTGCTGAAGTTCATGACACAATCAGCACCGAGGATAGTTTCGTTTCTGCAAAGTCTGAGATTAGCGACGATGCCAGCAGCCGCCAACGATCCGAA   2400
      TCGGTAACGACTTCAAGTACTGTGTTAGTCGTGGCTCCTATCAAAGCAAGACGTTTCAGACTCTAATGCTGCTACGGTCGTCGGCGGTTGCTAGGCTT
567    A  I  A  E  V  H  D  T  I  S  T  E  D  S  F  V  S  A  K  S  E  I  S  D  D  A  S  S  R  Q  R  S  E      599
```

FIG. 1E

```
2401  ACGCCGATGAGTGAAGATGACAAGCCATTCAACAAGGAGGAGGCAAAGGCTAAGGTCTTCAAGGAAATCGTTATTAATATGAAGTGTCTGCACATTGCCC   2500
      TGCGGCTACTCACTCACTGTTCGGTAAGTTGTTCCTCCTCCGTTCCGATTCCAGAAGTTCCTTAGCAGTTATTATATACTTCACAGACGTGTAACGGG    633
600   T  P  M  S  E  D  D  K  P  F  N  K  E  E  A  K  A  K  V  L  K  E  I  V  I  N  M  K  C  L  H  I  A  L

2501  TTTGCATGCTCCAGAATGTTGAAGGCAACCTGCAAGCAAATATGAATCTGGTGACCATGTTGAATAACTTGGTAGTACCTGCTGTTCGGAGCCACGAAGC   2600
      AAACGTACGAGGTCTTACAACTTCCGTTGGACGTTCGTTTATACTTAGACCACTGGTACAACATCATGGACGACAAGCCTCGGTGCTTCG
634   C  M  L  Q  N  V  E  G  N  L  Q  A  N  M  N  L  V  T  M  L  N  N  L  V  V  P  A  V  R  S  H  E  A    666

2601  GCCAATTCGAGAGGCGCGGTCTCGAATGTCTTGGGCTGTGTGCTGCTGGACACAGTAAGTTCCATCCTTACTAAATACATCTTCTTCTAACCTCTCT    2700
      CGGTTAAGCTCTCCGCGCCAGAACCCGACAGACTTACAGAAACCCGACGACGAACGACCTGTTCCATTCAAGGTAGGAATGATTTATGTAGAAGAGATTGGAGAGA
667   P  I  R  E  R  G  L  E  C  L  G  L  C  C  L  L  D  K

2701  GTTAGACTCTCGCAGAAGAAATATGACGCTGTTTATTCACTGTTACAGCAAGGGCCACGAAAACCTACAGTCACTGCTATTCATATCCTTTGCGATAT    2800
      CAATCTGAGAGCGTCTTCTTTATACTGCGACAACAATAAGTGACAATGTCGTTCCCGGTGCTTTTGGATGTCAGTGACGATAAGTATAGGAAACGCTATA
685   T  L  A  E  E  N  M  T  L  F  I  H  C  Y  S  K  G  H  E  N  L  Q  V  T  A  I  H  I  L  C  D  M    716
(SEQ ID NO:29)

2801  GTTAATTAGCACTCCATCCTTCGCTGTGGCTCCCGTTACCCAGGCCGTCCCCGAGGGCAATGGGTCCGGCTATTCCTGTCAACGGGTGCCGCAAGTCTCGGTGACGAATTCCAGAAAAGG   2900
      CAATTAATCGGTAGGAAGCGACCACCGAGGACACCGAGGGCTTACCGTTACCCAGGCCAT...
717   L  I  S  H  P  S  L  V  A  P  V  T  Q  A  D  K  E  T  V  A  P  P  A  F  Q  K  P  L  L  K  V  F  S    749
```

FIG. 1F

```
2901  AGAGCTCTCAAACCAAATTCACCCGGTCTGTACAACGGCAGCTGCGACAGCTCTTTCTAAGCTTCTGCTCACTGGTGTTTTACTCCATCGCGCCA   3000
      TCTCGAGAGTTTGGTTAAGTGGGCCAGACATGTTGCCGTCGACGCTGTCGAGAAAGATTCGAAGACGAGTGACCACAAAAATGAGGTAGACGGCGGT

750   R   A   L   K   P   N   S   P   A   S   V   Q   T   A   A   A   T   A   L   S   K   L   L   L   T   G   V   F   T   P   S   A   A   N   783

3001  ATATCCCGATGCCATTCAAGAGTTCAACCAACATGCCATTGAAACACTGCTACACAGTCCCTCGTTGTCTCCTTCTCCATCCCGAACTCGCGAGAATCC   3100
      TATAGGGCTACGGTAAGTTCTCAAGTTGGTTGTACGGTAGCTTTGTGACGATGTCAGGGAGCAACAGAGAAGAAGTAGGGCTTGAGCGCTCTTAGG

784   I   P   D   A   I   Q   E   F   N   Q   H   A   I   E   T   L   L   Q   S   L   V   V   S   F   F   H   P   R   T   R   E   N   P   816

3101  CGCACTCCGACAGGCACTCGCTACTCTTCTCCCTGTCTACTGCCACTCCCGGCGATAACACCCCAGCATGAGAAAGATTACTGTACCTGTCATCCGG   3200
      GCGTGAGGCTGTCCGTGAGCGATGAGAAGGACAGATGACGGTGAGGGCCGCTATTGTGGGTCGTATACTCTTTCTAATGACATGGACAGTAGGCC

817   A   L   R   Q   A   L   A   Y   F   F   P   P   V   Y   C   H   S   R   P   D   N   T   Q   H   M   R   K   I   T   V   P   V   I   R   849

3201  ACCATCCTAAACTCAGCGGAAGAATACTACTCACTTGAGGCTGAAGAGGACAGTGATGGTGATATTGATGAGTCTGTTGGGGAGAAGGAATTGAAGGCCC   3300
      TGGTAGGATTTGAGTCGCCTTCTTATGATGAGTGAACTCCGACTTCTCTGTCACTACTCAGACAACCCCTCTTCCTTAACTTCCGGG

850   T   I   L   N   S   A   E   E   Y   Y   S   L   E   A   E   E   D   S   D   G   D   I   D   E   S   V   G   E   K   E   L   K   A   L   883

3301  TGATGAGCGGAGTTCTGGTATGCTTGGCGAGTGACGGATGAGCGAAGAGTGATCGGACTTGGCGGCGAACGGTCCTTGCTGGGCCTTGCTAGCTC   3400
      ACTACTCGCCTCAAGAACCATACGAACGCCTCACCTGCCTACTGCCTTCTCACTAGCCTGAACGCCCGTTGCCCAGGAACGACCCCGGAACGATCGAG

```
3401  CAATGTTTGTGGCATTATCCACTTGCAACTGATTAAGGACATACTGGAACGAGTGCTCGGGATCAGTGAAGGCAGCAATGCTGCTAAACAACAAGA   3500
      GTTACAAACACCGTAATAGGTGAACGTTGACTAATTCCTGTATGACCTTGCTCACGAGCCCTAGTCACTTCCGTCGTAGCGACGAGATTGTGTTGCT
917      N  V  C  G  I  I  H  L  Q  L  I  K  D  I  L  E  R  V  L  G  I  S  E  G  S  N  R  C  S  K  Q  Q  R       949

3501  AAACTCCTGTTTTCACTGAGCAAGCTCTATATTGGCGCCGCCAACGGCACTTTCGCGCTCCAGCCCCCGAAGACGACTCGTTCCGTTCCA         3600
      TTTGAGGACAAAAGTGACTCGTTCGAGATATAACCGCGGCGGTTGCCGTGAAAGCGCGAGTCGGGCCTTGCTGAGCAAGGCAAGT
950      K  L  L  F  S  L  M  S  K  L  Y  I  A  P  P  T  A  L  S  R  S  A  S  Q  A  P  E  D  D  S  F  R  S  S    983

3601  GCGTGCGAAGCTCCATGGCGAACTCAATCCCGAAAACCTTGCCCTCGGCCAGAAGTCAAGGAGTACTTGACCAGACCATCGAAGAAGGTGTGGCGGC 3700
      CGCACGCTTCGAGGGTACCGCTTGAGTTAGGGCTTTTGGAACGGGAGCCGGTCCTTCAGTTCCTCGATGAACTGGTCTGGTAGCTTCTTCCACACCGCCG
984      V  R  S  S  H  G  E  L  N  P  E  N  L  A  L  A  Q  E  V  K  E  L  L  D  Q  T  I  E  E  G  V  A  A       1016

3701  TGATGCTGCTAGCCGAAATGCCCCTCGTCAAGGTGAAGAACGTGGTGCTCAAGCTACTGGCGGCTCCCATGCGACCTTCTAGCGCACGGCCGAGAGC   3800
      ACTACGACGATCGGCTTTACGGGGAGCAGTTCCACTTCTTGCACCACGAGTTCGATGACCGCCGAGGGTACGCTGAAGATCGCGTGCCGGCCGCTCTCG
1017     D  A  A  S  R  N  A  L  V  K  V  K  N  V  V  L  K  L  L  A  A  P  M  R  P  S  S  A  R  G  R  E  S       1049

3801  AGTGTCGAAAGTGACATTGGCAGTGTTCGATCTTCCAGAAGTGTTCGGCCGTCCGTTTGGGCGCCGCCGGTGTATCCGTGAGCCAGTA              3900
      TCACAGCTTTCACTGTAACCGTCACAAGCTAGAAGGTCTTCACAAGCCGGCAGGCATCGGACCGAAACCCGGCGGCCACATAGGCACTCGGGTCAT
1050     S  V  E  S  D  I  G  S  V  R  S  S  R  S  V  R  P  S  V  E  P  G  F  R  R  G  V  S  V  E  P  S  I       1083
```

FIG. 1H

```
3901  TCATGAGGAGGATGAGGAATGAGGATAGCCGGCGACTCTGACAGTAGAATGACTGTTATCAAAGAGGAGATGCCGACGCTATGGAGAATGATTTTC  4000
      AGTACCTCCTCCTACTCCTTACGGCCGCTGAGACCCGCCGCTGAGACCCTGTCATCTTACTGACAATAGTTCTCCTACGGCTGCGATACCTCCTTACTAAAG
1084                                                  M   E   E   D   S   R   M   T   V   I   K   E   E   D   A   D   A   M   E   E   *        1113

4001  GGTCTCAAGATCTTGCTGTCTGGTTCCGGCAGGCTAATGGTCATATTTATGGTTGCGATGTAATTATTCGATTCT  4100
      CCAGAGTTCTAGAACGACAGACCAAGCCGTCCGATTACCAGTATAAATACCAACGCTACAATTAATAAGCTAAGA

4101  TGGTTATGCTTGAACATGCTCTATATGTTACAAATAATTCACTCCAAACGTTCATGATGTATGAGCTCGTTTTATATGGCCTTACCAGGATAGCTC  4200
      ACCAATACGAACTTGTACGAGATATACAATGTTATTAAGTGAGGTTGCAAGTACATACTACTAGACAAAATATAACCGGAATGTCCTATCGAG

4201  AGTTCTTGGCGAAGTTATCCCAGACTGACAGCTGCCTCCAGGCCAGAATTGGCTAGTCTTAGTGTAGCATCTGAGTTATCGCGTGTATCAACAG  4300
      TCAAGAACCGCTTCAATAGGGTCTGACTGTCGACGGAGGTCCGGTCTTAACGATCCAGATCCATCGTAGACTCAGAATCAGAATCAGTGTC

4301  TGATCAGTGTGGAAGGGCCATCCGATCTGTTTGATCTTACCAGAACGTGTTACAACAATTCAACCACCACATATATGGTATCTACGTCAATGTGAATGA  4400
      ACTAGTCACACACCTTCCCGGTAGGCTAGACAAACTAGAAATGGTCTTGCACAATGTTGTTAAGTTGGGTGGTGTATATATACCATAGATGCAGTTACACTTACT
```

FIG. 11

```
4401  ATCTGCTTGGGCAGCCTTATGACTCTTGGTGACGCTCGGGGACTCGGGGCTTGATTCAATGCGGGCTTGACCGGCAAGACCGGATGTGAGACTCCTAGCATCGATGTGAGGCT
      TAGACGAACCCGTCGTCGAGCACTGAGACTACTGAGCTGCCGTGAGCCGCTGAGCCCGACCCCGAGCCGCTGAGCAACTAAGTTACGCCCGTTCTGCCGTACACCTCTGGAGGATCGTAGCCTACACTCCGA                                         4500

4501  TCCGTTTTAATTTCTTCCTCCAAATCGTCTGCCTGCCTCGCCTCGCTGCCTCGCTGCCTCGCTGCCTTTGAAATACTCCGGAGTACCAAAGTAAAGATAAATGGTTGACTCTGAGAGACTG
      AGGCAAAATTAAAGAAGGAGGTTTAGCAGACGAGCGACGACGAGCGACGACGAACTTTATGAGGCCTCCATGGTTTCATTGTTTCATTTCATTTACCAACTGAGACTCTGAC                                                         4600

4601  CTTTGACCTCCTGACCAAGTCGTCTGCCTAGCCAGAGGGGGAGTGTTCAAATGGCTTGTGAGGCTACTAAGGCCCACGATACACCGAGATGCAAAGAA
      GAAACTGGAGACCTGGTTCAGCAGGACGTCGTTCCAGCAGACTCCCTCCCACACAAGTACCGAACACTCCGAAACACTCCGATGATTCCGGGCGTGTGTGGCCTCTACGTTCTT                                                      4700

4701  GTCCGATACGGTCGTCCATATCTCGAGCACCTTTATTACTGGCCAGTTATATGGAGGCGTTTAATGATTGCGTGTTCGAATCCGATGAATAA
      CAGGCTATGCCAGCAGGTATAGAGCTCGTGGAAATAATGACCGGAAAACGTCAATAATACCTCCGAAAATCTAACGCACAAGCCTAGGCTACTTATT                                                                       4800

4801  TATCTCATTAGTCGACTAAACGGGGATGAGGATGATGACTGCTGCTGTATCTTGTCTCAAACTGTAATAAGCCTGTCGCAACACCGTACGGTTGACAAT
      ATAGAGTAATCAGCTGATTTGCCCCTCCTACCTACCTGACGACCTACTGACGACCAGAGTTTTGACATTATTGACATTATCCGAGAGCCGTGTGGCATGGCCAACTGTTA                                                          4900

4901  CCTGGGCAGATGGCAGCACCTGTAGAATCCAAGAAGACGCAGCTGACTCATTGAGACTGAATCCTTAACTATAATGACAGATAATAATACAAAA
      GGACCCGTCTACCGTCGTGGACATCTTAGGTTCTTCTGCGTCGACCTGAGTAACTCTGTCAACTTAAGGAATTGATATTACTGTCTGATTATTATGTTT                                                                    5000
```

FIG. 1J

```
5001  GTGCGGTGGTCAACTTCTTCCCAATCCCTCAAAAGTCCCGACCCTGTCTTCTAATAATCTGAGCGCTCCACCAAAGTCCAGCTTCTGGGCGAC
      CACGCCACCAGTTGAAGAAGGGTTAGGGGAGTTTCAGTCTGGGCTGGGACAAGAAAGATTATTAGACTGCGAGGTGGTTTCAGTCGAAGACCCGCTG   5100

5101  TTTCTTTTTTCTTCCCCATCCTTTTCCTTCCACTCTCCTCCTCGCTTCCTTGCTGTATGTTTTTGTGCTTGATTCACGACTT
      AAGAAAAAGAAGGGTAGGAAAGGTGAGAGAGGAAGGAGAAGCGAAGAAGCGACATACAAAAACAACGAACTAAGTGCTGAA   5200

5201  TCTTTTTCCTTCGTCGTGGATCCGTGTCTTCTGCCCCCACACTTGCAGAGGCACGATTTTTCCCCTCCTCCCTCCCCCTCC
      AGAAAAAGGAAGACCAGCACCTAGGCACAGAAGACGGGGGTGAACGTCTCCGTGCTAAAAGAGGAGGAAGCATGAGGGGGAGG   5300

5301  CCCCTGCTCTGCGCCTTTGGCATCCGGAGCCTGCGTCGATCGGAGACCGTCAGCTCCACGCCCAAGCTGACCGCTACATGCTCGT
      GGGGACGAGACGCGGAAACCGTAGGCCTCGGACACTCGCTGGCACTCGCTGGGCTGGGGTTCGACCTGGGCGATGTAGACGCA   5400

5401  TCATGTGGCAACTACCTGCGATGAGCATGGCGTCACCAAGGACTCTGAGAGTGATCGAGTTGGGGTGATCTTGTTGGATACCAAAACCTGCG
      AGTACACCGTTGATGACGCTACTCGTACCGCAGATGCAGTTGTTCCTGAGACGTCACTAGCTCAACCCACCTAGAACAACCTATGTTTTGGACGC   5500

5501  AGAGTCGCAGTGATTCTCCCTGCACCACACCTATTCCACCCCCTCTTTTGTCTTGATTCTGCGCTGCCGGGCTGCCGGGATTCTGCCGACGACATT   5596
      TCTCAGGTCACTAAGAGAGGACGTGGTGTGGAAGTTGGGGGAGAAAACACAGAACTAAGAACGGGCCGATAGCCCTAAGACGCTGCTGTAA
```

```
501  GGGGGTTGGTCTGGCCTCAATTGGCCTCTGCCGTATGAGCGTTTGCACGACGACGTGGCCAAGTACAAAATTGCGCCTGTAG    600
     CCCCCAACCAGACCGGAGTTAACCGGCATACCTCGCTAATAGTACGCTGCTGCACCGGTTTCATGTTTTAACGGACATC
114  G   G   W   S   G   L   N   W   P   L   A   V   W   S   V   C   T   D   I   I   H   A   T   T   W   P   K   Y   K   I   A   P   V   G   147

601  GTCTCATAACGGACAACCAGAGACAATTACTGTGACCGACAAGGAGCCCCGCCTGGGAACCGTCTTCTGCGCCAACGTCTTCGGCCACTACATGCTCGCGCA    700
     CAGAGTATTGCCTGTGGTCTGTTAATGACACTGGCTGTTCCTCGGGGCGGACCCTTGGCAGAAGACGCGGTTGCAGAAGCCGGTGATGTACGAGCGCGT
148  L   I   T   D   N   Q   T   I   T   V   T   D   K   E   P   R   L   G   T   V   F   C   A   N   V   F   G   H   Y   M   L   A   H   180

701  TAATGTCATGCCTCTCCTGCACCGATCCGACCCCCAACGGACCCGACGCGTGATATGGCTCTCCAGCACTGAAGCCACGATCAACTTCTTCGATGTT    800
     ATTACAGTACGGAGAGACGTGGCTAGGCTGGGCCGAGGCAGACGTCGACTTCGGTGCTAGTTGAAGAAGCTACAA
181  N   V   M   P   L   L   H   R   S   G   S   P   N   G   P   G   R   V   I   W   L   S   S   T   E   A   T   I   N   F   F   D   V   213

801  GATGATTTTCAGGCGCTCCGGTCCAAAGCTCCCTACGAGTCATCAAAAGCGCTAACAGACCTCCTACCCTCACCTCAGACCTTCCCAGTACTGCTCCCT    900
     CTACTAAAAGTCCGCGAGGCCAGTTTCGAGGGATGCTCAGTAGTTTCGATTGTCTGGAGGATAGGAGTGGAGTGAGTCTGAAGGGTCATGACGAGGGA
214  D   D   F   Q   A   L   R   S   K   A   P   Y   E   S   S   K   A   L   T   D   L   L   S   L   T   S   D   L   P   S   T   A   P   W   247
```

FIG. 2B

```
 901  GGGTGAAAAGCTTCTATTCCACCGACTTGAAACCGATTCCAAGCCACCGACCGACCGGCCTGAGACCGCCTGACCATACCCAACGTATACCTCTCTCACCC   1000
      CCCACTTTCGAAGATAAGTGGCTGAACTTTGGCTGAAGTTCGGCGTCGTGCCGGAGACTCTTGCCGGAGCTGTGTATGGTTGCATATGAGAGAGTGGG
 248   V  K  S  F  Y  S  T  D  F  E  T  D  S  K  P  S  T  G  P  E  T  A  S  T  I  P  N  V  Y  L  S  H  P      280

1001  CGGAATCTCGCTAGGCGTAGCCGGCGATTATACCCCTTCCTACAATCCTCATCTACGCAATGGTCGCGGCCCGCATTTTGGCTAGCCCGCATCCTCGGCTCCCCTTGGCAT   1100
      GCCTTAGAGCGATGCCGCTAATATGGGAAGGATGTTAGGATGCGTTACCAGCGGCTAAAACGATGCGGGCTAGAGCGCCGAGGGGAACCGTA
 281   G  I  C  A  T  A  I  I  P  L  P  T  I  L  I  Y  A  M  V  A  A  F  W  L  A  R  I  L  G  S  P  W  H      313

1101  ACCTTATCCACTACTAGGCGCTTGCAGCCCTGCTCTCTCCACACAATCAGAACTCGACGCCGCCGAACCACCGTACCGGAAACACGGCG   1200
      TGGAATAGTGTGATCCGCGAACGTCGGGACGTCGTGTAGTCTTGAGCTGTGTTAGTCTTGAGCTGTCGGGCGCGGGCTCCTGGCATGCCTTTGTGCCGC
 314   T  L  S  T  Y  L  G  A  C  S  P  V  W  L  A  L  S  T  Q  S  E  L  D  A  A  E  A  P  Y  R  K  H  G      347

1201  GCGGCAGGGTGAAATGGGGGTCTTCGGCGTCTCGATTAGGTGTAGCCTCCGTCGTATCTTCGAGGTTGACGGATGGGGCTATGGGGGTGTTCCTGGGGC   1300
      CGCGGTCCCACTTTACCCCAGAGCCCAGAGCTAATCCACATCGAGGCAGCAGCATAGAAGCCTCCAACTGCTACCCGATACCCCACAAGGACCCCG
 348   G  R  V  K  W  G  S  S  A  S  R  L  G  V  A  S  V  V  S  S  E  V  D  G  W  G  Y  G  G  V  P  G  A      380

1301  CGGCTGTGTGTGGCGGAGGATAGGGTCTGAAGGCGCAAGCGTGTGCAGTGGATCTTACGGCTGAGGGGAAGGAGGATTCCAGAACTGGGGGCTATATG   1400
      GCCGACAACACCCGCCTCCTATCCGACTTCCGCGTTCCGCGTCGCACCACGTCGCACCACGTCACCTAGAATGCCACTCCCTAAGTCCTTGACCCCGATATAC
 381   G  C  C  G  G  G  *                                                                                      386
```

FIG. 2C

```
1401  TTGGAGGCAGATGAGAGCTGAGGATCCTGTGGATAACTTACTTGATGAAGAGAAGGGGACTGGTGTGACGGCGTAGGTGGCTTGTCCTGGAGTG      1500
      AACCTCCGTCTACCTCCTGACTCCTCTAGGACACCCTATTGAATGAACTACTTCTCTCTTCCCCTGACCACTGCCGAACAGGACCCTCAC

1501  AGATCTCTTACATTTCGGCCTTCGTCCCTAAATCTTTCTCCCCTTCCTCTTTATTATACGATGTCGGGGTTTTATGTTCAATACAGCACATCTACGG      1600
      TCTAGAGAATGTAAAGCCGGAAGCAGGGATTTTAGAAAGACAGGGAAGGAATAATATGCTACAGCCGCCAAAATACAAGTTATGTCGTGTAGATGCC

1601  TACAAAGACAACATATAGCTAATATAATATCATAGATAATATCAAGCACAAAAGCTGATTCTGCAAGATCTCAATATCTTTATTCCAGTTTT      1700
      ATGTTTCTGTTGTATATCGATTATATTATATAGTATCTATTATCATTATTAGTTCGTGTTTTCGAGCTAAGACGTTCTAGAGTTATAGAATAAGGTCAAA

1701  CACTGCTCTTGTCTTCCATATTTACATTCCACGTCCACGTGCATCCTTTAAAAACAGT   1758
      GTGACGAGAACAGAAGTATAAATGTAAGGTGCAGGTGCACGTAGGAAATTTTTGTCA
```

FIG. 2D (SEQ ID NO:7)
1   GAATTCCTGTGATGGAGCAGAACCTCGGAGTATGCTCCGATGTCTCAGTACATTAAATTTGTAGCGATCCACGTGATTTCTATTTGCGTCCGAATAGT
    CTTAAGGACACTACCTCGTCTTGGAGCCTCATACGAGGCTACAGTCATGTAATTTAAAACATCGCTAGTGCACTAAAGATAAAACGCAGGCGTTATCCA    100
    (SEQ ID NO:9)

101 CTTCTGATACGGCTGAAGAAATATAGTACGTGGTCCAGTGCCTATAGACGGAAAGTATTTCGTAGTGCCTCCAAGGCAATAGGTCAACCTCGCAT
    GAAGACTATGCCGACTTCTTTATATCATGCACCAGGTCACGGAGTCGCCTTTCATAAAGCATGCACCGAGGGTTCGTTATCCAGTTGGAGCGTA    200

201 ACGGAGAATAACGGTACGTCCTGAAGAATGAGGGGATGTATTCTCCTTCTCCGAGGCCAGAAGGGGAACAGGCCCGACTGATCCGGCGAAAATTTC
    TGCCTCTTATTGCCATGCCAGAGACTTCCTTACTCCCCTACTAAGAGGAAGAGGCTCCCGTCTTCCCGGTTGTCCGGGGTGACTAGGCCGCTTTTAAAG    300

M  R  G  C  I  L  L  L  R  G  P  E  G  E  Q  A  R  T  D  P  A  K  I  S
1                                                                                     (SEQ ID NO:8)    24

301 CCCTCTCGAGTCTTCGCTCTCCCCCCACACGGCTGACTAACCCTTCCATTCTTGCCGCATCCAGCCAGCCTTTGTCGCCCCTTGTTCGG
    GGGAGAGCTCAGAAGCGAGAGGGGGGTGTGCCGACTGATTGGGAAGGTAAGAACGGGCGTAGGTCGGTCGGAAAACAGCGGGGAACCAAGCCC    400

25  P  L  D    L  L  S  P  P  L  V  R  A    36

(SEQ ID NO:30)

FIG. 3A

```
401  CTACTGTCATCTTCCCTTCTTCATCTTCAGCCGCTCTCGACTGTCTCTGCTCGATTTACAGTTACTACGGCGCAGACACGCTGCACAT   500
     GATGACAGTAGAAGGAAGAAGTAGACGGCGAGAGCTGACTTTATAAGTCAGAGAACTAAGTGATGCGTCTGTGCGACGTGTA

37   T  V  I  F  P  S  S  S  C  R  S  R  L  K  Y  S  V  S  C  S  D  L  Q  L  L  R  A  D  T  L  H  I   69

501  CTCCGGGATCATGACCGAATCCACTCAGGAACAGGCAACGATGGCCAGCGAATGCCCCCGCTGAGGACCCCGTTGAGGATTAGTCTTCCCTGAA   600
     GAGGGCCTAGTACTGGCTTAGTGAGTTCTTGTCCGTTGCTACCGGTCGCTTACGCCGGTGGGGGCGGGGCAACTCCTAATGCAGAAGGACTT

70   S  A  I  M  T  E  S  T  Q  E  Q  G  N  D  G  Q  R  M  P  P  A  P  A  T  P  V  E  D  Y  V  F  P  E   102

601  TATCGCCTGAAGCGTGTGATGGATGACCCGGAAAAGACGCCGCTATTGCTTATAGCTTGCGGTTCATTCTCACCTATTACGTTCCTGCACCTGCGCATGT   700
     ATAGCGGACTTCGCACACTACTGGGCCTTTTCTGCGGCGATAACGAATCGAACGCCAAGTAAGATGATAATCGAACGTAAGACGCTACA

103  Y  R  L  K  R  V  M  D  D  P  E  K  T  P  L  L  L  I  A  C  G  S  F  S  P  I  T  F  L  H  L  R  M  F   136

701  TCGAAATGGCCGCCGATTACGTCAAACTCGAGCACAGATTTCGAAATAATTGAGGTTATCTTTGCCGTCTCGGACGCCTACCGCAAGGCAGGTCTGC   800
     AGCTTTACCGGCGGCTAATGCAGTTGACTCGTGTCTAAAGCTTTATTAACTCCAATAGAAAGGCGGAGCCTGCGGATGGCCGGTTCCGTCCAGAACG

137  E  M  A  A  D  Y  V  K  L  S  T  D  F  E  I  I  G  G  Y  L  S  P  V  S  D  A  Y  R  K  A  G  L  A   169

801  GAGTGCCAATCACAGGTAGTTACTTTAACACACTCTTCCATAGTTACTATCCAGGACTGATCTGGCGGCTTTAGAATTGCAATGCCAAGAGCCGTG   900
     CTCACGGTTAGTGTCCATCAATGAAATTGTGTGAAGAAGGTATCAATGATAGGTCCTGACTAGACCGCCGAAATCTTAACGTTACACGGTTGCTCGGCAC

170  S  A  N  H  R  (SEQ ID NO:31)  I  A  M  C  Q  R  A  V   182
```

FIG. 3B

```
 901  GACCAAACGTCAGACTGTGATGATGGTGGATACAATGGAGCCGATCGACACAAGGAGTACCAGCCAACTGCCATCGTACTGGATCATTTGACTACGAGATCA     1000
      CTGGTTTGCAGTCTGACACTACTACCACCTATGTACCCTCGGCTAGCTGTTCCTCATGGTCGTTGACGGTAGCATGACCTAGTAAAACTGATGCTCTAGT
 183    D  Q  T  S  D  D  W  M  M  V  D  T  W  E  P  M  H  K  E  Y  Q  P  T  A  I  V  L  D  H  F  D  Y  E  I  N     216

1001  ACACTGTCCGCAAAGTATCGATACCGGAAAAGGCACTCGAAAAGTGAGTGCAAGTCTGTCTTATTGGCCGGGCAGATTTGGTCCATACCATGTCTACGCC     1100
      TGTGACAGGCGTTTCATAGCTATGGCCTTTTCCGTGAGCTTTTCACGTTCAGACAGAATAACCGGCCCGTCTAAACCAGGTATGGTACAGATGCGG
 217    T  V  R  K  G  I  D  T  G  K  G  T  R  K  R  V  Q  V  L  S  E  L  L  A  G  A  D  L  V  H  T  M  S  T  P     249

1101  CGGAGTATGGAGTGAGAAGGATCTCGATCATATTCTTGACAGTACGGGGTATGTTATGTGTATCTATCCTAAACTCGCCAAGCTACTGGTCTAGA     1200
      GCCTCATACCTCACTCTTCCTAGAGCTAGTATAAGAACCTGTCATGCCCATACAATACACATAGATAGGATTGAAGCGCGTTCGATTGACCAGATCT
 250    G  V  W  S  E  K  D  L  D  H  I  L  G  Q  Y  G                                                           266
                                           (SEQ ID NO:32) T

1201  CTTTCATCGTCGAGCGAAGCGGACAGATATTGACGAGGCGCATTGAGCGCCATGAAAAAGAATATCCATGTTATTCAACAACTTATTCAAAA     1300
      GAAAGTAGCAGCTCGCTTCGCCTGTCTATAACTGCTCCGAGCGTCGGTACCTTTCTATAGTACAATAAGTGTTGAATAAGTTTT
 267    F  I  V  E  R  S  G  T  D  I  D  E  A  L  A  A  L  Q  P  W  K  K  N  I  H  V  I  Q  Q  L  I  Q  N     299

1301  TGACGTTAGCAGCACTAAGATTCGCTTATTCCTCAGGCGGAGATATGAGCGTACGCTACTGATCCCGTGATTGAGTACTATGAGAATAAC     1400
      ACTGCAATCGTCGTGATTCTAAGCGAATAAGGAGTCCGCTCTATACTCGCATGCGATGAACTAGGAGCACTAACTGATACTCTTATTG
 300    D  V  S  S  T  K  I  R  L  F  L  R  R  D  M  S  V  R  Y  L  I  P  D  P  V  I  E  Y  I  Y  E  N  N     332
```

FIG. 3C

```
1401  CTCTACATGACGACGGTACGACACAACCGACGGCCGACAAGGGCAAGACACGAGAGGAGCCCGCGCCTTCAAATTAGCATTGCTCAAAAGCCAGATAA   1500
      GAGATGTACCTGCTGCCATGCTGTGTTGGCTGCCGGCTGTTCCCGTTCTGTGCTCTCGTGCTCCGGGCGCGGAAGTTTAATCGTAACGAGTTTTCGGTCTATT
333   L  Y  M  D  D  G  T  T  Q  P  T  A  D  K  G  K  T  R  E  E  P  P  A  P  S  N  *                    357

1501  GGCCACGCGACGACGTCATGACGACCATTGCTGGTTTCACGAAGATATCAAACCGCGGGCGAATGCAAATCTCTGCGCTGATCTGAGCAAGCACTGATTC   1600
      CCGGTGCGCTGCTGCAGTACTGCTGTGTAACGACGTGGTAACACCAAAGTGCTTCTATAGTTTGGCGCGCCCGCTTACGTTAGAGACGGACTAGACTCGTTCGTGACTAAG

1601  CGGTAAGCCGCAAGTTGGGGGAGGATTTAATGAGCCCAACCGTATGGGTTTGTTCCGGTTCAAGTCACTGCGATTAACGACACGCCTTATGACTGTCATAT   1700
      GCCATTCGGCGTTCAACCCCTCCTAAATTACTCGGGTTGGCAGTACCAAACAAGGCCAGTTCAGTTGACGCTAATTGCTGTGCGGAATACTGACAGTATA

1701  CGACAGGTCCCTCTCCAGAGCCGGCCTACACAACAGTGATGCTGGCGTTCTTCTATTCCAAGCCCTCAACATCTAAGTGCAGCGGGCGAATTC   1792
      GCTGTCCAGGGAGAGGTCTCGGCCCGATGTGTTGTCACTACGACCGCAAGAAGATAAGGTTCGGGAGTTGTAGATTCACGTCGCGCTTAAG
```

FIG. 3D

(SEQ ID NO:10)

1  TTGCCTTCTTAGACTTGATATCTGAAGGAATATAACGGAAGAGATCATCTGGTTTGATGTACTGTATTAGCGGGAGCACGTGATTATTCCCTCGATA
   AACGGAAGAATCTGAACTATAGACTTCCTTATATTGCCTTCTCTAGTAGACCAAACTACCATGACATAATCGCCCCTCGTGACTAATAAGGAGGCTAT
(SEQ ID NO:12)

101 GGCCAGTGGCGTATGTCATAAGGAAGACTGACGCCTGAGGGGAAAACACCTCCCGCCCGAGTTCCATCTTTCACGCTCGATCTCTCCAAG
    CCGGTCACCGCATACAGTATTCCTTCTGACTGCGAGCTCCCCTTTTGTGGAGGGAGCGGGCTCAAGGTAGAATAGTGAAAGTGCGAGCTAGAGAGTTC

201 TTTCTGGCTTCATTGACTGAGTGCTCGCCTTGCCTAGTGGGTAGATTTAGATCTAGTGCAAATCACTTGCCTACATTCTGAACCTGTTTGTTCAGCC
    AAAGACCGAAGTAACTGACTCAGCGAGCGGAACGGATCACCCATCTAAATCTAGATCAGCGTTAGTGAACGATGTAAGACGATCTTGACAACAAGTCGG

301 TTGCGGTTCCCCTCACTACTATCTCTTCTACCGTTTCGAAAACACTTCCTCCTGCGGCGAGACTAGTATCTATGCCTGTCGCCACTTTC
    AACGCCAAGGGAGTGATGATAGAGAAGAATGGCAAGCTTTGTGAAGGAGGACGCCGCTCTGATCATAGATAGCGGACAGCGGGTGAAAG

401 ACCACCGTGTTCACTAGAGAATAGTGAAAGACTCAAGTCGTCTACCAAAAATGTGGTCATGGTTCCGGTGGTGCCGGCGAGAAGCCAAGGAAGC
    TGGTGGCACAAGTGATCTCTTATCACTTTCTGAGTTCAGCAGAGATCAGCATGACCAAGGCCACCACGGCCGCTTCGGTTCCTTCG

1   M  W  S  W  F  R  W  C  G  R  A  E  A  Q  G  S       16
                    (SEQ ID NO:11)

```
1001  ACAAACCCGGGGTTCGGCGAGCAGGTGGACGAAGAAGATCTGGAGGCGGAACTCGAGGGCATGGAGCAGGAAGCT
      TGTTTGGGCCCCAAGCCGCTCGTCCACCTGCTTCTTCTAGACCTCCGCTTGAGCTCCGCCTACTGCTCGAGCTGTC
145   T  N  P  G  F  G  E  Q  V  D  E  E  D  L  E  A  E  L  E  G  M  E  Q  E  A  M  D  E  R  M  L  H  T  G

1101  GCACAGTACCAGTTGCAGATCAGCTGAGTCGGCTCAATCGGCTCTCCCTTTCCCACCTCAAAAGGAACTCCGACTGA
      CGTGTCATGGTCAACGTCTAGTCGAGTCGATTAGCCGAGACGCGTTACGCTTGAGAGGGAAAGGGTGAGTTTCGCTTGAGGCTGACT
179   T  V  P  V  A  D  Q  L  N  R  L  P  A  P  A  N  A  E  P

1201  CAGCCTTCCAGCCGCCAAAGCGCCAAAGCGAAACAGAAGCAGAAGAAGAAGACGAGGAAGCCGAGTTGGAGAAGTTACGCGCGGAAATGGCCATGTGAGAGTGGTCC
      GTCGGAAGGTCGGCGGTTTCGCTTTGTCTTCGCTTTGTCTTCGTCTTCTTCTTCTGCTCCTTCGGCTCAACCTCTTCAATGCGGCGCCTTACCGGTACACTCTCACCAGG
198   A  K  A  K  Q  K  A  E  E  E  D  E  E  A  E  L  E  K  L  R  A  E  M  A  M  *
(SEQ ID NO:33)

1301  TGGTGCTTTGGTCTCTTTGGTCTAACTTTAATCTTTTTCTCCCCCTACACATATGATGAACAGGGAATCGTTATCATGACGCACTACGATTAGCCAAG
      ACCACGAAACCAGAGAAACCAGATTGAAATTAGAAAAAAGAAAGGGGATTGTATACTACTTGTCCCTTAGCAATGTGCGTGATGCTAATCGGTTC

1401  CACTGTGTTCTTTTCCGTCGGCTCGTTGCGATTCCTCTCTCGGCGGCTAATTACTTATCTAGTTGTACCAACTACCCCGCGAGGCTTCTGTTGAGG
      GTGACACAAGAAAAAGGCAGCCGAGCAACGTCTAAGGAAGAAGAAGAGGCGCCGATTAATGAATAGATCAACATGTTGATGGGGCCGCTCCGAAGACAACTCC
```

FIG. 4C

```
1501 CGAGAGCGAAAGCCCAGACGTGTCGCCCCTTGCCCTGATTACTGCTGGCCACTCCGTTCTGTCCACGCTGTGTATCCCACTCTG 1600
     GCTCTCGCTTTCGGGTCTGCACAGCGGGAACGGGACTAATGACCCGTGAGGGACTCGTGCGATGGAGCAGGTGCGACACATAGGGTGAGAC

1601 TAATAATCTACCAAGTGAATACTTTTCTGGATGATTTGAAGGGCCTATGTTTCCTACGCCATCATGTCATTAGATATGTTTTGGATCATGTTTCCCCA 1700
     ATTATTAGATGGTTCACTTATGAAAAGACCTACTAAACTTCCCGGATACAAAGATGCGGTAGTACAGTACACACTTAGTACAAAGGGT

1701 GCGCAATTGATGCCCATTTGCAGTTCACACTCGTGTCATATGAACCTCAGAATATGAAAAGCCGGTTCTCAACCCAGCAAAACGTCACTGAGGATTAAAT 1800
     CGCGTTAACTACGGGTAAACGTCAAGTGTGAGCACAGTATACTTGGAGTCTTATACTTTCGGGAAGAGTTGGGTCGTTTTGCAGTGACTCCTAATTTTA

1801 TGAGTAATTGAGTAAAACTAAATTAGTAGCTAGATAACTCCCGTTTCCCACCAGACCTAACACCGTCAAACAGATAATCAACAAGGAAAGAAAGAAA 1899
     ACTCATTAACTCATTTGATTAATCATCGATCTATTGAGGGCTGATTGTGGCAGGTTGTCTATTAGTTGTTCTTTCTTT
```

```
22001  CTGCATTATAGCTTCTTTAGAAAGGGAGTTGATATTGGCCAAAAACAAAACTATAAGCTCACGAATGATGAAGAAGGATATCTCAAGGTTCGTCGA  22100
       GACGTAAATATCGAAGAAATCTTCCCTCAAGTTTTTGATATTGAGTGCTTACTACTTCTTCCCTATAAGAGTTCCAAGCAGCT
100      A  F  I  A  S  L  E  R  E  L  I  L  A  K  K  Q  N  Y  K  L  T  N  D  E  E  G  I  F  S  R  F  V  D           132

22101  TCAGTTCATAAGAACATGTTTTGCTGGTGTGGAAAGCCCTGACAAGAACGTCAGATTTAGAGTTTTACAGTTATTGCCGTTATAATGGATAATATAGGG  22200
       AGTCAAGTATTCTGTACAAAACGCCACCACACCTTTCGGGACTGTTCAAGTCTAAATCTCAAAATGTCAATAATCGGCAATATTACCTATTATATCCC
133      Q  F  I  R  K  V  L  R  G  V  E  S  P  D  K  N  V  R  F  R  V  L  Q  L  L  A  V  I  M  D  N  I  G           165

22201  GAAATCGATGAATCACTTTTCAATTTATTATTAAATATTGTCTTTAAATAAGGAGGATTATGATAAGAGAACCACGGTTAGGATACAGGCTGTGTTTGTTTAA  22300
       CTTTAGCTACTTAGTGAAAGTTAAATAATAATTATAACAGAAATTTAAATACTAAGGAAATACTAATATCTGAATCCAATCCTATGTCCGCACAAACAAATT
166      E  I  D  E  S  L  F  N  L  L  I  L  S  L  N  K  R  I  Y  D  R  E  P  T  V  R  I  Q  A  V  F  C  L  T       199

22301  CTAAATTCAGGATGAAGAGCAAACTGAACATTAACTGAGCTTTCTGATAATGAAGAAAATTTTGAAGCTACCAGAACTCTAGTTGCTTCTATCCAGAA  22400
       GATTTAAAGTCCTACTTCTGTTTGACTTGTAAATTGACTCGAAAGACTATTACTTCTTAAACTTCGATGCTCTTGAGATCAACGAAGATAGGTCTT
200      K  F  Q  D  E  E  Q  T  E  H  L  T  E  L  S  D  N  E  E  N  F  E  A  T  R  T  L  V  A  S  I  Q  N        232
```

FIG. 5B

```
22401  CGATCCGTCAGCTGAAGTACGGAGGGCTGCAATGCTGAATTTGATCAATGATAATACTAGACCGTATATCTTGGAGAGGCTACAGATGTAAACATC   22500
       GCTAGGCAGTCGACTTCATGCCTCCCGACGTTACGACTTAAACTAGTTACTATTATGATCTGGCATATAGAACCTCTCCGATCTCTACATTTGTAG
233    D  P  S  A  E  V  R  R  A  A  M  L  N  L  I  N  D  N  T  R  P  Y  I  L  E  R  A  R  D  V  N  I          265

22501  GTTAATAGAAGGCTCGTGTATTCGAGAATTTGAAATCAATGGAAGAAAGTGTTTCGATGAATATTGACCGCCATATTTGATCAATTGATTGAGTGGG   22600
       CAATTATCTTCCGAGCACATAAGTCTTAAACTTTAGTTACCCTCTTCACAAAGCTACTATAATAACTGGCGTATAAAACTAGTTAACTAACTCACCC
266    V  N  R  R  L  V  Y  S  R  I  L  K  S  M  G  R  K  C  F  D  D  I  E  P  H  I  F  D  Q  L  I  E  W  G   299

22601  GTTTAGAAGATAGGAATTATCAGTGAGAATGCCGTGTAAGAGACTCATTGCTCTCATGATTGGTTAAATGCTCTGGATGGCGATTTGATAGAATTACTAGA   22700
       CAAATCTTCTATCCTTAATAGTCACTCTTTACCGCACATTCTCTGAGTAACGAACAATTACGGACTAACCTACCGCTAAACTATCTTAATGATCT
300    L  E  D  R  E  L  S  V  R  N  A  C  K  R  L  I  A  H  D  W  L  N  A  L  D  G  D  L  I  E  L  L  E   332

22701  AAAATTGGATGTCTCAGATCCTCAGTGTGTGTTAAGGCTATAGAAGCACTTTTCAATCAAGGCCAGATATATTATCTAAATCAAATTCCTGAAAGT   22800
       TTTTAACCTACAGAGTCTAGGAGTCACACAATTCGATATCTTCGTGAAAAAGTTAGTTCCGGTCTATATAATAGATTTAGTTAAGGACTTTCA
333    K  L  D  V  S  R  S  S  V  C  V  K  A  I  E  A  L  F  Q  S  R  P  D  I  L  S  K  I  K  F  P  E  S   365
```

FIG. 5C

```
22801  ATTGGAAAGACTTACCGTAGAAATTGCCTTCCTCTTTCGGGCTATTATTATTGTACTGTTGGATAATATAACAGAAATAACAGAATTCTTTGAAAG   22900
 366    I  G  K  T  L  P  *  K  L  P  S  S  F  G  A  I  I  I  V  L  L  D  N  I  T  E  H  L  E  E  N  F     399
        TAACCTTTCTGAAATGGCATCTTTAACGGAAGAAGCCCGATAATATTATCATAGACAACCTATTATATTTGTCTTTACGACTTCTTTTGAAAG         P

22901  CAGAAGCCTCAAAATTATCCGAGCATTAAACCTATATATTCTTCAGATATCATCACAACGACATTTCTAATGACTCTCAGTTGCCATTTGATATAA   23000
 400    E  A  S  K  L  S  E  H  *  T  Y  I  L  Q  I  S  S  Q  R  H  F  *  *  L  S  V  A  I  *  Y                432
        GTCTTCGGAGTTTTAATAGGCTCGTAAATTTGGTAATATAAGAAGAGTCTATAGTAGTTGCTGTAAAGATTACTGAGAGTCAACGGTAAACTATAATT

23001  CACTTTAGAGTTTATTATTGAGCAACTATCGATTGCCGCCGAAAGGTATAGGATGATTATAGCAGTGTACGAGGAGATGCTACGAT   23100
 433    T  L  E  F  I  I  E  Q  L  S  I  A  A  E  R  Y  R  *  L  *  Q  C  T  R  R  C  Y              465
        GTGAAATCTCAAATAATAACTCGTTGATAGCTAACGGCGGCTTTCCATATCCTACTAATATCGTCACATGCTCCTCTACGATGCTA

23101  ATGCTGGCCTTAACTACACTCTCCGAACCTCTTATTAAATTGGTATTCGTGTAATGAAAGTCTGCATAATGAAAGATTTTGTAACAATGCAA   23200
 466    M  L  A  L  T  T  L  S  E  P  L  I  K  L  V  F  V  *  *  K  S  A  *  *  K  I  L  *  Q  C  K        499
        TACGACCGGAATTGATGTGAGAGGCTTGGAGAATAATTTAACCATAAGCACATTACTTTCAGACGTATTACTTTCTAAACATTGTTACGTT

23201  TAGAAATCATTAATGATATTAGAGACGACGATATTGAAAAACAAGAAGAAAAATAAAAGCAAGAAGAGATTAATGCCAGAAATGAGACTTCGT   23300
 500    *  N  H  *  *  Y  *  R  R  R  Y  *  K  T  R  R  K  *  K  Q  E  E  I  N  A  R  N  E  T  S           532
        ATCTTTAGTAATTACTATAATCTCTGCTGCTATACTTTTGTTCTTCTTTTATTTCGTTCTTCTCTAATTAGGCTTTACTCTGAAGCA                V
```

FIG. 5D

```
23301  CGATGAAGAGGACGAAAACGGCACACATAATGACGAAGTTAACGAGGATGAAGAAGACGACAATATTCATCCTTCATTCTGCTGTAGAAAACTTAGTG  23400
       GCTACTTCTCCTGCTTTGCCGTGTGATACTGCTTCAATTGCTCCACTTCTTCTGCTGTTATAAAGTAAGGAAGTAAGACATCTTTGAATCAC
533    D  E  E  D  E  N  G  T  H  N  D  E  V  N  E  D  E  E  D  D  N  I  S  S  T  H  S  A  V  E  N  L  V      565

23401  CAGGGAAACGGCAACGTATCTGAGAGTGACATATAAATAATCTCCACCCGAAAAGGAAGCGTCCTCAGCAACAATTGTTCTGTCTTACAAGGTCAT  23500
       GTCCCTTTGCCGTTGCATAGACTCTCACTGTATTATTATTAGAGGGTGGGCTTTCCTTCGCAGGAGTCGTTGTTAACAAGACAGAATGTTCCAGTA
566    Q  G  N  V  S  E  S  D  I  I  N  N  L  P  P  E  K  E  A  S  S  A  T  I  V  L  C  L  T  R  S  S      599

23501  CATATATGCTAGAACTAGTTAACACCGTTAACAGAAAACATTTTAATTGCGTCGTTGATGGACACTTTGATCACACCAGCGGTTAGAATACCGGCC  23600
       GTATATACGATCTTGATCAATTGTGGCAATTGTCTTTTGTAAAATTAACGCAGCAACTACCTGTGAAACTAGTGGTCGCCAATCTTATGGCGGGG
600    Y  M  L  E  L  V  N  T  P  L  T  E  N  I  L  I  A  S  L  M  D  T  L  I  T  P  A  V  R  N  T  A  P    632

23601  AAATATTAGGGAGCTTGGTGTCAAGAACCTTGGTTATGTTGTCTCTTGGATGTGAAGTTGGCTATTCATAACATGTACATTGTCGTTTCG  23700
       TTTATAATCCCTCGAACCACAGTTCTTGGAACCACAGAGAACCTACACTTCAACCGATAACTATTGTACATGTAGAATCCATACGCAAGC
633    N  I  R  E  L  G  V  K  N  L  G  L  C  C  L  L  D  V  K  L  A  I  D  N  M  Y  I  L  G  M  C  V  S    665
```

```
24201  TAACCAGACAGGTTCAACAAAAAGATACAGTGCAGCTTACATTCTTGATCGATGTGCTCAAATATACGCTCAAATTGAGAAGAAGAAATAAGAAG     24300
       ATTGGCTGTCCAAGTTGTTTTTCATGTCACGTCAAGTCGAATGTAAGAACTAGTACACCAGTTTATATGGAGTTAACTCTTCTTTCTTATTCTTC
833    N Q T G S T K K D T V Q L T F L I D V L K I Y A Q I E K K E I K K                                   865

24301  ATGATCATCACTAATATAAACGCTATATTCTTCTTGAACAAGATTATTGAAGAACTTCTTGAGTATTCTGAGGATTATTCAGAAACTCAGAAATG     24400
       TACTAGTAGTGATTATATTTGCGATATAAGAAGAACTTGTTCTAATAACTTCTTGAAGAACTCATAAGACTCCTGAAGACTCCTAAGAGTCTTTAC
866    M I I T N I N A I F L S S E Q D Y S T L K E L L E Y S D D I A E N D                                899

24401  ATAATTAGACAATGTTAGCAAAAATGCTCTGGACAAGCTAAGGAATAATTTGATTGAAGAGATCAATGAAGGTCAGAAACTCAGAACTCAGTCAAA     24500
       TATTAATCTGTTACAATCGTTTTTACGAGACCTGTTCGATTCCTTATTAAACTTCTCTAGTACTTCTCCAGTCTTTGAGTCTGTT
900    N L D N V S K N A L D K L R N N L N Q L I E E I N E R S E T Q T K                                  932

24501  AGATGAGAACAACACTGCGAATGACCAATACTCGTCTATTTTGGGAATTCATTCAATAATCTTCAAATGACACCATAGAACACGGTGCTGATATAACT     24600
       TCTACTCTTGTTGTGACGGCTTACTGGTTATGAGCAGATAAAACCCTTAAGTAAGTTATTAGAACTTACTGTGGTATCGTGCGCGACTATATATGA
933    D E N N T A N D Q Y S S I L G N S F N K S N D T I E H A A D I T                                    965
```

FIG. 5G

```
24601  GATGGAAATAACACAGAATTGACTAAACGTACTACTGTTAATATTTCGGCAGTCACAATACACAGAGCAAGTAACTCAAGGAAAGAACGAGGATCAAGAG   24700
       CTACCTTTATTGTGTCTTAACTGATTTGTTGACAATTATAAAGCCGTCAGTGTTGTCTCGTTCATTGAGTTCCTTTCTTGCTCTAGTCTTC
  966    D  G  N  T  E  L  T  K  T  T  V  N  I  S  A  V  D  N  T  T  E  Q  S  N  R  K  R  T  R  S  E  A      999

24701  CGGAGCAAATTGACACATCCAAAACCTGGAAAACATGAGTATTCAAGACGTGACTGTAGCAAAAATGTAAGTTTTGTTTTACCTGACGAGAAATC    24800
       GCCTCGTTTAACTGTGTAGGTTTTGGACCTTTTGTACTCATAAGTTCTGCAGTTGACATCGTTTTTACATTCAAACAAATGGACTGCTCTTTAG
 1000   E  Q  I  D  T  S  K  N  L  E  N  M  S  I  Q  D  T  S  T  V  A  K  N  V  S  F  V  L  P  D  E  K  S      1032

24801  AGATGCAATGTCCATAGATGAAGAAGATAAGGATTCAGAGTCTGTAAAATTGATATGCGAGCTCTTCATCTATTTAAGTTGATTTT             24900
       TCTACGTTACAGGTATCTACTTCTTCTATTCCTAAGTCTCAGACACATTTTAACTATATACCTCGAGAAGTAGATAAATTCAACTAAAA
 1033   D  A  M  S  I  D  E  E  D  K  D  S  E  S  F  S  E  V  C  •                                   1051

24901  TTGGTTGTAAACATATTGTATTTTATTCTTAGGTTTGTTAATTCTTACGGCTTACCAGATATAGATGCTATATGTTATTGCATTACGCACATTACCCG  25000
       AACCAACATTTGTATAACATATAAAATAAGAATCCAAACAATTAAGAATGCCGAATGGCGAATGCTATATATCACGATATACAATACGTAATGGGC

25001  GTGGCACAAATTATGCAAATATTCCAAGGCTATAAATTCTTGGTGAAAGGAACTGAAATTAGTCCAGTAATTAGTCACCAGAATGGACATATAAACTAT  25100
       CACCGTGTTTAATACCTTTATAAGGTTCCGATATTTAAGAACCACTTCCTTGACTTAATAAGACAGGTCATTACGGTCCTGTATATTTGATA

25101  TAATGCATTTTATTACAATTATCCTAGAAAATATCCTATATAATTAAGTAAAGAATATAAGATCAAAGAACAAATAAAGTCGAGTAGAATTTTC      25200
       ATTACGTAAAATAAATGTTAATAGGAATTCTTTTATAGGATATATTAATTCATTTCATTCAGCTCATCTAAAG
```

FIG. 5H (SEQ ID NO:16)

1 TCTTTGGTGTCAATGTGTATTATTCCGAGTTACTCCAGGCTAGGTTCAGGAGTACTTATTTATTATTATACACCGGAGCAAGTCATAT
AGAAACCAGTTACCACAGTATAAGGCTCAATGAGGTCCGATCCAAGTCCTCATGGTCTTACATGAAATAAATATGTGCCTCGTTCAGTATA
(SEQ ID NO:18)

101 AATTACGCAAACGATTCGAAATTGTTAAAGCAGGATCAACGTATCTCATTTCTTTTTGAAAGACGGGTAATAGAAAGTCTCACCCCACATG
TTAATGCGTTTGCTAAGCTTTAACAATTTTCGTCCTAGTGCATAGAGTAAAGAAAAACTTTCGCCCATTATCTTCAGAGACTCAGCGTGGGGTGTAC

201 GATATCGTACTATTCGTATATGAATGTAAATACTCGCAATAATCGATTTTATTTAGCTTCACAATCTCTCAAACTTATCGTCTTGATCAATCTTTACGTT
CTATAGCATGCATATACCTTACATTTTATGAGCGTTATGCTAAATATCGAAGTGTTAGAGAGTTTGAATCAGAACTAGTTAGAAATGCAA

301 TTACCAAATAATCGCCTGTTCTCGGCCATTTTTTGCTTATACCATCTGCTTCTACCATACTGCTCATATGTGACGGTGTCGTCTCCAAGAAAATAACAATG
AATGGTTATTAGGGACAAAGACCGGTAAAAACGAATATGGTAGAGATGGTATACACTGCCACAGGTATACACTGCCACAGAGTGTCTTTTTATTGTTAC

401 TAAAATTGACCCAGCGTGACGACAGTAGACTGTAAGTTATATAGTACAATCATATCTCTACCTTAGTCACTGTTCCTCCACTGTTAAGTAGAGAGAGAGAGA
ATTTAACTGGGTCGCACTGCTGTCATCGACATTCAATAGTTAGTAGATGAATCAGTGACAAGGAGTGACAATTCATCTCTCTCTCT

501 GTTTAAAGTGGAGAAGGCAAGAAAAAGTCCACTCACTTATTACGTAATGGATCCAAGCACCCGATTTTAAACCGGCCAGCCAAATGAAGAACTACAAC
CAAATTTCACCTCTTCCGTCTTTTCACGTGAATAATTGCATTACCTAGGGTGGTTCGTGGGCTAAAATTGGGGCGTCGGTTTACTTCTGATGTTG

M D P T K A P D F K P P Q P N E E L Q P
(SEQ ID NO:17)

FIG. 6A

| | | |
|---|---|---|
| 601 | CACCGCCAGATCCAACACATACGATACCAAAATCTGACCACCATAGTTCCATATGTTTAGCTGATTATAATTCTCGATGATGCTCCTTCAATCTCGA<br>GTGGCGGTCTAGGTTGTGTATGCTATGGTTTTAGACTGGTGGTATCAAGGTATACAAATCGACTAATATTAAGAAGCTAGCTACGAGGAAGTTAGAGCT | 700 |
| 21 | P  P  D  P  T  H  T  I  P  K  S  G  P  I  V  P  Y  V  L  A  D  Y  N  S  S  I  D  A  P  P  N  L  D | 53 |
| 701 | CATTTACAAAACCCTGTCGTCAAGGAAAAAAACGCCAACTCAAGCAACCGAATGACCATATTCCATTAAATACTAGTGACTTCCAGCCACTATCTCGG<br>GTAAATGTTTTGGGACAGCAGTTCCTTCCTTTTTTTTGCGGTTGAGTTCGTTGGCTTACCTGGTTGAGTTCGTTGGCTATAAGGTCGGTGATAGAGCC | 800 |
| 54 | I  Y  K  T  L  S  S  R  K  K  N  A  N  S  S  N  R  M  D  H  I  P  L  N  T  S  D  F  Q  P  L  S  R | 86 |
| 801 | GATGTATCATCGGAGGAGAAAGTGAAGGGCAATCGAATTGACGCTACTCTACAGGATGTTACGATGACTGGAATTTGGGGTACTGAAGAGCC<br>CTACATAGTAGCCTCCTCTTCACTTCCCGTTAGCTTAAGCTGCGATGAGATGTCTACAACTGCTACTGACCCTAAACTCCCATGACTCTCGG | 900 |
| 87 | D  V  S  S  E  E  E  S  E  G  Q  S  N  G  I  D  A  T  L  Q  D  V  T  M  T  G  N  L  G  V  L  K  S  Q | 120 |
| 901 | AAATTGCTGATTTGGAAGAAGTTCCTCACACAATTGTAAGACAAGCCAGAACTATTGAAGATTACGAATTTCCTGTACACAGAAAAGTTACA<br>TTTAACGACTAAACCTTCTTCAAGGAGTGTGTTAACATTCTGTTCGGTCTTGATAACTTCTAATGCTTAAAGGACATGTGTCTAACTGCTTTTCAATGT | 1000 |
| 121 | I  A  D  L  E  E  V  P  H  T  I  V  R  Q  A  R  T  I  E  D  Y  E  F  P  V  H  R  L  T  K  K  L  Q | 153 |

FIG. 6B

```
1001  AGATCCTGAAAAACTGCCTCTGATCATCGTTGCTTGTGGATCATTTTCTCCCATAACTACATTTGAGAATGGCTTTAGATGATATC  1100
      TCTAGGACTTTTTGACGGAGACTAGTAACGAACACTAGTAAAAGAGGTATTGTATGATGTAAACTCTTACAAATCTACTATAG
154    D  P  E  K  L  P  L  I  V  A  C  G  S  F  S  P  I  T  Y  L  H  L  R  M  F  E  M  A  L  D  D  I    186

1101  AATGAGCAAACGCGTTTGAAGTGGTTGGTTATTTCTCAGTAAGTGATAACTATCAAAAGCGAGGGTTAGCCCCAGCTTATCATCGTGTCCGCA  1200
      TTACTCGTTTGCGCAAACTTCACCAACCAATAAAGAGTCATTCACTATTGATAGTTTTCGCTCCCAATGGGGTCGAATAGTAGCACAGGCGT
187    N  E  Q  T  R  F  E  V  V  G  G  Y  F  S  P  V  S  D  N  Y  Q  K  R  G  L  A  P  A  Y  H  R  V  R  M    220

1201  TGTGCGAATTAGCATGCGAGCGGACATCATCTGGTTAATGGTTGATGCCTGGGAATCTTTACAATCAAGTCTTATACAAGGACAGCAAAAGTCTTGGACCA  1300
      ACACGCTTAATCGTACGCTCGCCTGTAGTAGAACCAATTACCAACTACGGACCCTTAGAAAATGTTAGTTCATATGTTCCTGTCGTTTCAGAACCTGGT
221    C  E  L  A  C  E  R  T  S  S  W  L  M  V  D  A  W  E  S  L  Q  S  S  Y  T  R  T  A  K  V  L  D  H    253

1301  TTTCAATCATGAAATAATCAAGAGAGTGGAATCATGACTGTAGATGGTGAAAAAATGGGCGTAAAAATCATGTTATTGGCAGGCGGTGATCTTATC  1400
      AAAGTTAGTACTTTATTAGTTCTCTCCACCTTAGTACTGACATCTACCACTTTTTTTACCGCATTTTTAGTACAATAACCGTCCGCCACTAGAATAG
254    F  N  H  E  I  N  I  K  R  G  G  I  M  T  V  D  G  E  K  M  G  V  K  I  M  L  L  A  G  G  D  L  I    286

1401  GAATCCATGGGCGAGCCTCATGTGTGGCCTGATTCAGACCTGCACCATATTTGGGTAATTATGATGTTTGATCGTGAAAGGACTGGTTCTGATGTTA  1500
      CTTAGGTACCCGCTCGGAGTACACACCCGGACTAAGTCTGGACGTGGTATAAAACCCATTAATAATACCTACAAACTAGCACCTTCCTGACCAAGACTACAAT
287    E  S  M  G  E  P  H  V  W  A  D  S  D  L  H  H  I  L  G  N  Y  G  C  L  I  V  E  R  T  G  S  D  V  R    320
```

FIG. 6C

```
1501  GGTCCTTCTTGCTTTCCATGATATCATGTATGAACACAGAAGAAATATCCTTATTATTACAAACAACTATTATTACAATGATATTCCTCTACGAAGTGCCG
       CCAGGAAGAACGAAAGGTACTACTATAGTACAATACTGTGTCTTCTTATAGGAATAATAGTTGTTGAATATAAATGTTACTATAAGGAGATGCTTCACGC
321    S   F   L   L   S   H   D   I   M   Y   E   H   R   R   N   I   L   I   K   Q   L   I   Y   N   D   I   S   S   T   K   V   R

1601  GCTTTTCATCAGACGTGGAATGTCAGTTCAGTATAGATATCTCCAAACTCTGTCATCCGTTACATCCAAGAGTATAATCTATACATTAATCAAGTGAACCG
       CGAAAAGTAGTCTGCACCTTACAGTCAAGTCAAGTATAGAAGAAGGTTGAGACAGTAGCAATGTTCTCATATTAGATATGTAATTAGTTCACTTGGC
354    L   F   I   R   R   G   M   S   V   Q   Y   L   L   P   N   S   V   I   R   Y   I   Q   E   Y   N   L   Y   I   N   Q   S   E   P

1701  GTCAAGCAGTCTTGGATAGCAAAGAGTGAGTTTATTACAACTCTGATACTGCAGCAGTTCAAATTTACCACTTTCCTCTTCAAGGTGCATAGAAAAAAA
       CAGTTCGTCCAGAACCTATCGTTTCTCACTCAAATAATGTTGAGACTATGACGTCGTCAAGTTTAAATGGTGAAAGGAAGTTCCACGTATCTTTTTTT
387    V   K   Q   V   L   D   S   K   E   *

1801  GTTCCTGATGCACGATTTAAAATGTTTACAGCAGAGCAACAATCATGTGAACATGTCAAACATTTATTTTAACACTTAATAATTATATTATAATAACCACA
       CAAGGACTACGTGCTAAATTTACAAATGTCGTCTCGTTGTTAGTACACTTGTACAGTTGTAAATAAAATGTGAATTATTAATAATTATATATGGTGT

1901  CCAGCGGTAAGTTTCATAAGAAAACCTTTCAGACAAACATTCCAGTGAATCGTATACGTAAATCAGCAAAATAGCTTATAAAATCAGAATCGAAGA
       GGTCGCCATTCAAAGTATTCCTTTGGAAAGTCGTTGTAAGGTCACTTAGTCACATATGCATATATTTAGTCGTTTAATCATTTAGTTCTTAGCTTCT

2001  TACTTGATCTACTCGCTTACTATTAATGCGGTAATGATCTATATTGAATTTTGCACGTCTATAGTAACTTAAAAGTCTTGTAATATTTGAAGTAACAA
       ATGAACTAGATAATGACGTATTATCGGGATAGTTTAGCCTTAGTAAACGTGCAGATATCATTGAATTTTCAGAACATTATAAACTTCATTGTT

2101  TGCCGTATAATACTGCATAATAGCCCTATCAATCGGAATATACCAAAACATCCTTT  2156
       ACGGCATATTATGACGTATTATCGGGATAGTTAGCCTTATATGGTTTTGTAGGAAA
```

FIG. 6D (SEQ ID NO:19)
28401 GTTTGAATTGTGTTGTTGTAGAAATTTGTGTGCTTTAAATGTTATGTTATAATGAAATCTTATTTAGAATTTATTTAACGTTTTTGCTGTGCTTATATAAA   28500
      CAACTTAACACAACACAATCTTTAAACACACAAATTACAATACAATATTACTTTAGAATAATCTAAATAATTGCAAAACGACACGAATATTATTT
(SEQ ID NO:21)

28501 CATTACATATAATAAAAGGAGTAGAGAAGAAGTGGTAGAGAGAGAGTACAAAATCTACCTGCCAGAACTCTCCTATATATATTTCAGTGGTGTCTGGATTA   28600
      GTAAATGTATTATTTCCTCACCATCTCTCTTCACGATCGGTCTTCATGTTTAGATGACGGTCTTGAGAGGAATATATATATAAAGGTCACCACAGACCTAAT

28601 CCTACCTCAAGCCATACCATATCCATATAGTATGGTATAGGTATAGTATTTGCGGATGTATTTGCAAATTCTACCCCAATCCAGCAGCTTCTATCACTATCTCGTATACCACCATA   28700
      GGATGGAGTTCGGTATGGTATAGTATAGTATATTTGCGGATGTATTTGCAAATGTTTTAAAGATGTTTAAAGATGTCGAAGATAGTGATAGAGCATATGGTGTAT

28701 GGCACCACCACTGTTTGTGTAAATTTACTCTCCTGAGGGGGGGGTGGCTCAACACGGTTAGGCCTTCTTCCCGCACAATCCGATGAAACCCACAATCGCC   28800
      CCGTGGTGTGACAAACACATTTAAATGAGACTCCCCCCCCACCGAGTTGTGCCAATCCGGAAGAAGGGTTGGTATACGTTAGGCCTACTTTGGGGTGTTAGCGG

28801 TCCGTCTCTTCCACTGTGCACGGCGCTAGCTCAACATCTTCCCGCCACATTTACTGTGCAAAGAAGGTGCATAATCTAAAAAACATACTTAGAGAA   28900
      AGGCAGAGAAGGTGACACGTGCCGCCGGATCGAGTTGTAGAAGGGCGGTGTAAATGACACCGTTCTTCCACGTATTAGATTTTTTGTATGCATACTCTT

28901 TGGAAAGGGCAAGATAATATCGGACCGTAGTGAGTCACTGCTTTTGGTATTGCAACAACTGCTTTTGGTATTGCAACAACTGGTGTTGTTGCGATTAAAT   29000
      ACCTTTCCCGTTCTATTATAGCCTGGCATCACTCAGTCATCGACGATGATCCAGTCCTGTGAACGAAACCATAACGTTGTTGACGGCAGAACGTGGTTTGCGATTA

FIG. 7A

```
29001  GCCCATTGTGATGGCTCATCACCCTCACGACGAAGTAAGACCCGGGGCACAAGAAATACGAGATCATAACAGTTCGAGTCCGTTTATTGTGTGCGGTT    29100
       CGGGTAACACTACCGAGTAGGTGGGAGTGCTGCTTCATTCTGGGCCCCGTGTTCTTTATGCTCTAGTATTGTCAAGCTCAGGCAAATAACACACGCCAA

29101  TTGGTACGCTTTTCGTGAGGTGTACTACCATTCATGAGAGTCGTTTTAGGAGTCTCATGAAAGATATGTATCTGTTGATGAACTGTAAAATTTGCA     29200
       AACCATGCGAAAAAGCACTCCACATGATGGTAAGTACTCTCAGCAAATCCTGACAGTACTTCTATACATAGACAACTACTTGACATTTTTAAACGT

29201  GAAATTGCGCTATTCCGTTTATTTCATTGTCGATTCGGTGTGTTAATATATTAGGGGTACAAATATACTAGAAGTTCTCCCTGAGGATATAGGAATGCGCAA  29300
       CTTTAACGCGATAAGGCAAATAACAGCTAAGTAAACTGTTATTATAATCCCATGTTTTATATGATCTTCAAGAGGGAGCTCCTATATCCTTACGCGTT

29301  ATGGGCATTTGATGTGACACAAAATTTGGACAATATAACGATTCATTTTTAGATCGTTGTTCAACGTCCCAGTGGCCGAGTGGTTAAGGCGATGCCTGC    29400
       TACCCGTAAACTACACTGTGTTTTAAACCTGTTATATTGCTAAGTAAAAATCTAGCAACAAGTTGGCAGGGTACCGCGTCACCGGCTACGGACG

29401  TATTTCCTCAGAAAAGCAATTAGGCATTGGGTTTTACCTGGCAGGTTCGAATCCTGTCTGTGACGCTTTTTTAATTCTTACTCCATGACAAAAGCG       29500
       ATAAAGGAGTCTTTTCGTTAATCCGTAACCCAAATGAGCGGTTCCAAGCTTAGGACAGACACTGCGAAAAATTAAAGAAATAAGAGTACTGTTTCGC
```

FIG. 7B

29501 GATAAAAATTCCCGCATTCGGCGTAAAAAATCCGGTTTTTTTTTAGCACTCGCTGTTTTGCCTCTACCGGGTGAAAATGACGATGAAGACGGCTGG 29600
      CTATTTTTAAGGGCGTAAGCCCGCATTTTTTAGGCCAAAAAAAATCGTGAGGCGACAAAAACGGAGACGATGCCCACTTTTACTGCTACTCTGCCGACC

29601 AATGCGCTGCATCCGCTTACGTAGGATAGAACACCTACAAGATTTACGAACTTTATTGCTGCTAAGATTCGTGAAGATTCGCTATCCATATCTTTTTAGTTTCCCCCA 29700
      TTAACGCGACGTAGGCGAATGCATCCTATCTTGTGATGTTTCTAAATAACGAGCTTCTGAAATAACGATAGTATAGAAAAATCAAGGGGGT

29701 TTTCACAATGGGATACCGTGTTTTTCTGTAGGTACGCTTTCTCATAGTTAATAGAGTCAGTAATTCATTTTCATTTTTGCAGAAAGGAATTYCTTCAC 29800
      AAGTGTTACCCTATGCAACAAAAAGACATTCGAAAGAGTATCAATTATCTCAGTCATTAAGTAAAAACGTCTYCCTTAAAGAAGTG

29801 CTAATTTAGAATTTCATCAACATTTATTGTATCTGCATGGTATAACAAATTAGAAAAAATTGGAAGGGAAAAAAACTGTYGCTCAATTACTYATACC 29900
      GATTAAATCTTAAAGTAGTTGTAAATAACATAGACGTACCATATGTYAATCTTTTAAACCTYCCCTTTTTTTAAACCTYTTAACTAAGTATGG

29901 AGGGATAGAAAAAAAAGGAAACATGGATCCCACAAGAGCTCCGATTTCAAACCGCCATCTGCAGACGAGGAATGATTCCTCACCCGACCCGGAA 30000
      TCCCCTATCTTTTTTTTTTTCCTTGTGTACCTAGGGTGTTCTGAGGCCTAAGTTGGCGTAGACGTCTGCTCCTTAACTAAGGAGGTGGGCTGGGCCTT

1   M D P T R A P D F K P P S A D E E L I P P D P E    25
                              (SEQ ID NO:20)

```
30501  CTCTGAACAAACAAGGTTTGAAGTCATAGGTGGATATTACTCCCCTGTTAGTGATAACTATCAAAGCAAGGCTTGGCCCCATCCTACCATAGAGTACGT  30600
       GAGACTTGTTTGTTCCAAACTTCAGTATCCACCTATATCAGTATATTGATAGTTTCGTTCCGAACGGGGTAGGATGGTATCCATGCA
193    S  E  Q  T  R  F  E  V  I  G  G  Y  Y  S  P  V  S  D  N  Y  Q  K  Q  G  L  A  P  S  Y  H  R  R  V  R    225

30601  ATGTGTGAATTGGCCTGCTGCGAAAGAACCTCATCTTGGTTGATGATGCATGGGAGTCATTGCAACCTTCATACACAAGAACTGCCAAGTCTTGGATC  30700
       TACACACTTAACCGGACGCTTTCTTGGAGTAGAACCAACTACTACGTACCCTCAGTAACGTTGGAAGTATGTTCTTGACGGTTCCAGAACCTAG
226    M  C  E  L  A  C  E  R  T  S  S  W  L  M  V  D  A  W  E  S  L  Q  P  S  Y  T  R  T  A  K  V  L  D  H    259

30701  ATTTCAATCACGAAATCAATATTAAGAGAGGTGGTAGCTACTGTTACTGGAGAAAAATTGGTGTGAAAATAATGTTGCTGGCTGGTGACCTAAT      30800
       TAAAGTTAGTGCTTTAGTTATAATTCTCTCCACCATCGATGACAATGACCTCTTTTTAACCACACTTTATTACAACGACCACTGGATTA
260    F  N  H  E  I  N  I  K  R  G  G  V  A  T  V  T  G  E  K  I  G  V  K  I  M  L  L  A  G  G  D  L  I       292

30801  AGAGTCAATGGGTGAACCAAACGTTTGGGCGGACGCCGATTTACATCACATTCTCGGTAATTACGGTTGTTGATTGTGAACTACTGGTTCTGATGTA  30900
       TCTCAGTTACCCACTTGGTTTGCAAACCCGCCTGCGGCTAAATGTAGTTGTAAGAGCCATTAATGCCAACAACTAACAGCTTGATGACCAAGACTACAT
293    E  S  M  G  E  P  N  V  W  A  D  A  D  L  H  H  I  L  G  N  Y  G  C  L  I  V  E  R  T  G  S  D  V       325
```

FIG. 7E

```
30901  AGGTCTTTTTTGTTATCCATGATGTATGAACATAGAAGGAATATTCTTATCATCAAGCAACTCATCTATAATGATATTTCCACGAAAGTTC     31000
       TCCAGAAAAACAATAGGTACTATAATACATACTTGTATCTTCCTTATAGAATAGTTCGTTGAGTAGATATTACTATAAAGAAGGTGCTTCAAG
326    R  S  F  L  L  S  H  D  I  M  Y  E  H  R  R  N  I  L  I  I  K  Q  L  I  Y  N  D  I  S  S  T  K  V  R    359

31001  GTCTATTTATCAGACGGCCATGTCTGTACAATATTTGTTACCTAATTCGGTCATCAGTGTATATCCAAGAACATAGACTATATGTGGACCAACCGAACC     31100
       CAGATAAATAGTCTGCGCGGTACAGACATGTTATAAACAATGATTAAGCACAGTAGTTCCAGTAGTTCTTGTATCTGATATACACCTGGTTGGCTTGG
360    L  F  I  R  R  A  M  S  V  Q  Y  L  L  P  N  S  V  I  R  Y  I  Q  E  H  R  L  Y  V  D  Q  T  E  P    392

31101  TGTTAAGCAAGTTCTTGGAAACAAAGAATGATTGCCGTCCGGAATTGCTTCGTTCTTCTTCATCTTCTTCTTACAATTTCCCCTACAG     31200
       ACAATTCGTTCAAGAACCTTGTTTCTTACTAAACGGCAGGCCTTAACGAAGCAAGAAGTAGAAAGAATAGTTAAAGGGATGTC
393    V  K  Q  V  L  G  N  K  E  *    401

31201  GAATTAATTGGAGGTACAAGCGAGTAGAAATGTGACATATGACTTACCTATCTGTGTTTTAGTATAGTTTTTTTTCTGTAGTATAATTCACTTTTACA     31300
       CTTAATTAACCTCCATGTTCGCTCATCTTTACACTGTATACTGAATGATAGAACAAAATCATATCAAAAAAAGACATCATATTAAGTGAAAATGT

31301  CTAATTTTTCGCCTTTTCTTAAAGAGCTAATTTCTATAACCTTCAGCGGTTATACCAAATATAAAAATGGAAGGAAACAAACAGTAAGAAATAA     31400
       GATTAAAAAGCGGAAAAGAATTTCTCGATTAAGATATATTGAAGTGCGCCAATATGGTTTATATTTTTACCTTCCTTTGTTGTCATTCTTTATT

31401  GCGCAACAGCACGTTAGTTCACCATTGGAATTCCAACATTTCAAAATTTAATCTAATGGCAAGAGATATCACATTTTGACCGTATTTTGAGAAAGTTGTG     31500
       CGCGTTGTCGTGCAATCAAGTGGTAACCTAAGTTGTAAAGTTTTAAATTAGATTAAAACTGCATAAATCTTCAACAC
```

FIG. 7F

```
31501  GCGCTGTAAATAATGATGAGGCAGGAAAATTGTTATCTGCTTGGACTTCAACCGTACGCATTGAGGACCGGAATCAACCGACTCTAATTCATTATATAT
       CGGACACATTTATTACTACTCCGTCCTTTTAACAATAGACGAACCTGAAGTTGGCATGCGTAACTCCCTGCCTTAGTTGGCTGAGATTAAGTAATATATA  31600

31601  TCCACTCGTACCACCTGGAATGTTGAAGTATGTTTCTCCTAGCAAAATTAAAACCATCGTGAATGAAGCGTTACTAACTATAACTGGTAGCTTT
       AGGTGACGATGGTGGACCCTACAACTTCATACAAAGAGATCGTTTTAATTTGGGTAGGCACTTACTTCGCAATGATTGATATTATTGACCATCGAAA  31700

31701  GTCACTCGTACCAGGAAAGTGAAGATTAAACTGAATTTTAAA  31743
       CAGTGAGCATGGTCCTTTTCACTTCTAATTTGACTTAAAATTT

FIG. 7G
```

(SEQ ID NO:22)
15901 TTCTACTACTCAGTACAAAAAGAGACAGGCTGCTTTATTTATACTTTGTGCCACAAGAATGATCAACATAAATATCAATAGTATCTGCAA        16000
       AAGATGATGAGGTGCATGTTTTTCTGGTGCGACGAAATAAATATGAAAACACGTGTTCTTACTAGTTGTATTTATAAGTTCATCATAGACGTT (SEQ ID NO:24)
16001 CACATCTGCTTCACGGAACTAAACCCGTTGAGCCAGTGCCCCTGGAACGTAAACTATCGAATTGGAACAGCCAAAACAGCCAAGCAAGATT        16100
       GTGTAGACGAGGTGCCTTGATTTGGGCACCTCGTTGATTTGATAGCGTTTAACCCTAATTGTTCGGTTTTGTCGGTTCGTTCTAA

16101 CACGAAACCGGCGCCTCGTTTGGACCCCGAAGCCCCATTAACGCGGGCCGGCCTTTAACGCCGTTACGACCAAGATCGGACAAGCAAACACTCCCAGCGACCACT        16200
       GTGCTTGCGCCGGACCAACCTGGGGCTTCCGGGTAAATTGCGCCAATGTTACGGCAATGTTCGTTCTAGCCGTCTGGTGAGGGTCGTGGTGTCGTA

16201 CACTGCACGACGACCAACATAACTAGAACATGGCAGATACTCCTGTATCTGCAGGGATCATCAACAGCGTTCCGCAGGACATCAACAGCGTGTCCGAAG        16300
       GTGACGTGCTTCGTTGTTATTGATCTTGTACCGTCTATCGCTAGGACGTCCCGTAGTTGTCGTCAGCACCTCCGGACCTTC

16301 AAGATGGTTACCTCAGCAACGAGGACGACTCACTCAGCAACGAGCTCGAGATGCACAGGTCGATGGAAGAGTCGTCGACGACGTGTCAACAAGCTGCT        16400
       TTCTACCAATGGAGTCGCCTGCTCTGTGCAGTGAGTCGTTGCAGTGTCGCAGTTACCTTCTCAGGACGACGTGCAACTTGTTCGACGA

16401 CAACTGGGTCCTGCTCGCTGCCCCTGGGCAAGTATAGGTAGGAGAATGGCCAAGACTCTATGGAGTAGGTTCATTGAACACTTTGTAAAGTGTTGTT        16500
       GTTGACCCAGGACGGGACGACCGTTCACGGTTCTAGATACCTCATGGAGATACCTCAATCGAACAACATTGAACAATACTCACAAACAA

```
16901 GGATTTGGAAATAGACTTTGATTATCTCGTTGGTGGACTTCACCAACATGGTGAGTGTCTTTGAACGCATTACGACATCAACAAAAGTACAGGGCGATA 17000
      CCTAAACCTTTATCTGAAACTAATAGACAACCACCTGAAGTGGTTGTACCACTGAAGACTGGTATAATGCTGTAGTTGTTTTCATGTCCGCTAT
   64  D  L  E  I  D  F  D  Y  L  L  V  D  F  T  N  M  V  S  V  L  N  A  Y  Y  D  I  N  K  K  Y  R  R  A  I         96

17001 AACTACCTTTCGTGAATGCTGCGCAAGGTATCTTTGACGGTATAGATTGGATCGGAGCGGTCAAGGAGTTTCACCAATCCATTCGAGGCAGTGACAA 17100
      TTGATGGAAAGCACTTACGACGCGTTCCATAGATCTAACCTAGCCAGTCCAGTTCCTCCAAAGTGTTAGGTAACCTCTCCGTCACTGTT
   97  N  Y  L  F  V  N  A  A  Q  G  I  F  D  G  I  D  W  I  G  A  V  K  E  V  F  T  N  P  L  E  A  V  T  N        130

17101 ATCCGACATACAAGATACAACTGGTGGGCGTCAAGTCTAAGATGACATGGGGCCTTATTTTCCAGGCCAATGTGTTTGGTCCGTACTACTTATCAGTAA 17200
      TAGGCTGTATGTTCTATGTTGACCACCCGCAGTTCAGATTTCTACTGTACCCCGGAATAAAAGGTCCGGTTACAACCAGGCATGATGAATAGTCATT
  131  P  T  Y  K  I  Q  L  V  G  V  K  S  K  D  D  M  G  L  I  F  Q  A  N  V  F  G  P  Y  Y  F  I  S  K          163

17201 AATTCTGCCTCAATTGACCAGGGGAAAGGCTTATATCTTTCGAGTATTATGTCCGATCCTAAGTATCTTTCGTTGAACGATATTGAACTACTA 17300
      TTAAGACGGAGTTAACTGGTCCCCCTTTCCGAATATAGAAAGCTCATAATACAGGCTAGGATTCATAGAAGCAACTTGCTATAACTTGATGAT
  164  I  L  P  Q  L  T  R  G  K  A  Y  I  V  W  I  S  S  I  H  S  D  P  K  Y  L  S  L  N  D  I  E  L  L         196
```

ESSENTIAL FUNGAL GENES AND THEIR USE

BACKGROUND OF THE INVENTION

The invention relates to essential fungal genes and their use in identifying antifungal agents.

Fungal infections (mycoses) may be cutaneous, subcutaneous, or systemic. Superficial mycoses include tinea capitis, tinea corporis, tinea pedis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections can also contribute to meningitis and pulmonary or respiratory tract diseases. Opportunistic fungal infections proliferate, especially in patients afflicted with AIDS or other diseases that compromise the immune system.

Examples of pathogenic fungi include dermatophytes (e.g., *Microsporum canis* and other M. spp.; and Trichophyton spp. such as *T. rubrum*, and *T. mentagrophytes*), yeasts (e.g., *Candida albicans*, C. Tropicalis, or other Candida species), *Torulopsis glabrata, Epidermophyton floccosum, Malassezia furfur* (*Pityropsporon orbiculare*, or *P. ovale*), *Cryptococcus neoformans, Aspergillus fumigatus,* and other Aspergillus sp., Zygomycetes (e.g., Rhizopus, Mucor), *Paracoccidioides brasiliensis, Blastomyces dermatitides, Histoplasma capsulatum, Coccidioides immitis,* and *Sporothrix schenckii.*

Various strains of the fungus Aspergillus sp. cause aspergillosis, a potentially life-threatening disease in humans and other mammals. The clinical manifestations of aspergillosis in humans are very similar to those observed in rodents and cows. For example, necrosis, angioinvasion, and hematogenous dissemination are common features of aspergillosis in rodent and bovine model systems and in humans. In humans, aspergillosis typically is caused by inhalation of conidia (i.e., asexual spores produced by the fungus). In cattle, pathogenic Aspergillus typically enter the animal through the forestomach and then disseminate through the blood of the animal. Putative virulence factors produced by pathogenic species of Aspergillus include hydroxymate siderophores (i.e., compounds that compete with human iron-binding proteins to acquire iron to support fungal growth), lipids having the ability to inhibit complement and phagocytosis, and proteinases that can degrade elastin and other substrates.

SUMMARY OF THE INVENTION

The invention is based on the discovery of four new genes in the fungus *Aspergillus nidulans* that are essential for survival. These genes are referred to herein as AN97, AN80, AN17, and AN85; for convenience, the polypeptides encoded by these genes are referred to herein as "AN polypeptides." The genes encoding the AN polypeptides are useful molecular tools for identifying similar genes in pathogenic microrganisms, such as pathogenic strains of Aspergillus (e.g. *Aspergillus fumigatus* and *Aspergillus flavus*). In addition, the AN polypeptides and the essential genes encoding them are useful targets for identifying compounds that are inhibitors of the pathogens in which the AN polypeptides are expressed. Such inhibitors inhibit fungal growth by being fungistatic (e.g., inhibiting reproduction or cell division) or by being fungicidal (i.e., by causing cell death).

The invention, therefore, features an isolated AN97 polypeptide having the amino acid sequence set forth as partial sequences in SEQ ID NOs: 2 and 29, or conservative variations thereof. Nucleic acids encoding AN97 also are included within the invention. In particular, the invention includes an isolated nucleic acid of (a) SEQ ID NO:2, as depicted in FIG. 1, or degenerate variants thereof; (b) SEQ ID NO:2, or degenerate variants thereof, wherein T is replaced by U; (c) nucleic acids complementary to (a) and (b); and (d) fragments of (a), (b), and (c) that are at least 15 base pairs in length and that hybridize under stringent conditions to genomic DNA encoding the polypeptide set forth as partial sequences in SEQ ID NOs: 2 and 29.

The invention also features an isolated AN80 polypeptide having the amino acid sequence set forth in SEQ ID NO:5, or conservative variations thereof. Nucleic acids encoding AN80 also are included. In particular, the invention includes an isolated nucleic acid of: (a) SEQ ID NO:4, as depicted in FIG. 2, or degenerate variants thereof; (b) SEQ ID NO:4, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO:5.

The invention also includes an isolated AN85 polypeptide having the amino acid sequence set forth as partial sequences in SEQ ID NOs:8, 30, 31, and 32, or conservative variations thereof. Nucleic acids encoding AN85 also are included. In particular, the invention includes an isolated nucleic acid of: (a) SEQ ID NO:7, as depicted in FIG. 3, or degenerate variants thereof; (b) SEQ ID NO:7, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs: 8, 30, 31, and 32.

The invention also features an isolated AN17 polypeptide having the amino acid sequence set forth as partial sequences in SEQ ID NOs: 11, 33, 34, and 35, or conservative variations thereof. Nucleic acids encoding AN17 also are included. In particular, the invention includes an isolated nucleic acid of: (a) SEQ ID NO:10, as depicted in FIG. 4, or degenerate variants thereof; (b) SEQ ID NO:8, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs: 11, 33, 34, and 35.

The invention also includes isolated nucleic acids that are at least 15 base pairs in length and which hybridize under stringent conditions to a nucleotide sequence selected from the group consisting of SEQ ID NO:1, SEQ ID NO:4, SEQ ID NO:7, and SEQ ID NO:10. In addition, the invention includes allelic variants (i.e., genes encoding isozymes) of the genes encoding AN97, AN17, AN80, and AN85. For example, the invention includes genes that encode an AN polypeptide but which gene includes point mutation, deletion, promoter variant, or splice site variant, provided that the resulting AN polypeptide functions as an AN polypeptide (e.g., as determined in a complementation assay, as described herein and elsewhere). Also included within the invention are isolated nucleic acid molecules containing the cDNA sequences contained with ATCC accession number 209473, (deposited on Nov. 19, 1997), as well as polypeptides encoded by the cDNA sequences of these nucleic acid molecules.

Identification of the AN97, AN17, AN80, and AN85 genes and the determination that they are essential allows homologs of these genes to be found in other organisms (e.g., fungi, such as yeast like *S. cerevisiae;* mammalian cells, such as human or murine cells; or plant cells). Thus, the AN polypeptides used not only can be as a model for identifying similar essential genes in other Aspergillus strains, but also to identify homologous essential genes in other organisms, e.g., *S. cerevisiae*. Because such genes are homologs, they can be expected to be essential for survival without the need for extensive characterization of the homologous gene or polypeptide. Even though some such homologous genes may have previously been identified, the invention allows one to determine that such genes are essential for survival. Having identified such homologous genes as essential, these genes and the polypeptides encoded by these genes can be used to identify compounds that inhibit the growth of the host organism (e.g., compounds that are fungicidal or fungistatic against pathogenic strains of the organism).

As used herein, the term "yeast" refers to organisms of the order Saccharomycetales, which includes yeast such as Saccharomyces and Candida. As described below, several homologs of the AN polypeptides have been identified in the yeast *S. cerevisiae* and are essential for survival. Given the identification of such genes as essential in *S. cerevisiae*, homologs of these essential yeast genes can also be found in pathogenic yeast strains (e.g., *Candida albicans*). The *S. cerevisiae* polypeptide and gene termed D9798.4 are homologs of the AN97 polypeptide and gene. The D9798.4 polypeptide and nucleic acid are depicted in FIG. 5, and are set forth in SEQ ID NOs:14 and 13, respectively (GenBank Accession No. U32517). As described herein, various methods of the invention can utilize the D9798.4 polypeptide or conservative variations thereof. Also useful are isolated nucleic acids of (a) SEQ ID NO:13, as depicted in FIG. 5, or degenerate variants thereof; (b) SEQ ID NO:13, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO:14.

Yeast homologs of the AN85 and AN80 polypeptides and genes also have been identified as being essential for survival, and these homologs can be used in the methods described herein. As described above for AN97, conservative variations, degenerate variants, complementary sequences, fragments, and nucleic acids in which T is replaced by U also can be used in various methods of the invention. Two homologs of AN85 have been identified. The amino acid and nucleic acid sequences of the AN85 homolog termed YGR010W are depicted in FIG. 6 (GenBank Accession No. Z72795); these sequences are set forth as SEQ ID NOs:17 and 16, respectively. The amino acid and nucleic acid sequences of the AN85 homolog termed L8543.16 are depicted in FIG. 7 (GenBank Accession No. U20618); these sequences are set forth as SEQ ID NOs:20 and 19, respectively. The AN80 polypeptide and gene have a homolog in yeast, termed L8004.2, the amino acid and nucleic acid sequences of which are depicted in FIG. 8 (GenBank Accession No. U53876). These sequences are set forth as SEQ ID NOs:23 and 22, respectively.

The term AN97 polypeptide or gene as used herein is intended to include the polypeptide and gene set forth in FIG. 1 herein, as well as homologs of the sequences set forth in FIG. 1. For example, encompassed by the term AN97 gene are degenerate variants of the nucleic acid sequence set forth in FIG. 1. (SEQ ID NO:1). Degenerate variants of a nucleic acid sequence exist because of the degeneracy of the amino acid code; thus, those sequences that vary from the sequence represented by SEQ ID NO:1, but which nonetheless encode an AN97 polypeptide are included within the invention. Likewise, because of the similarity in the structures of amino acids, conservative variations can be made in the amino acid sequence of the AN97 polypeptide while retaining the function of the polypeptide (e.g., as determined in a complementation assay, as described herein and elsewhere). AN97 polypeptides and genes identified in additional Aspergillus strains may be such conservative variations or degenerate variants of the particular AN97 polypeptide and nucleic acid set forth in FIG. 1 (SEQ ID NOs:2 and 29; and 1, respectively). The AN97 polypeptide and gene share at least 80%, e.g., 90%, sequence identity with SEQ ID NOs:2 and 29; and 1, respectively. Regardless of the percent sequence identity between the AN97 sequence and the sequence represented by SEQ ID NOs:1 and 2, the AN97 genes and polypeptides encompassed by the invention are able to complement for the lack of AN97 function (e.g., in a temperature-sensitive mutant) in a standard complementation assay. AN97 genes that are identified and cloned from additional Aspergillus strains, and pathogenic strains in particular, can be used to produce AN97 polypeptides for use in the various methods described herein, e.g., for identifying antifungal agents. Likewise, the term AN80 encompasses homologues and conservative and degenerate variants of the sequences depicted in FIG. 2. Such homologues, conservative variations, and degenerate variants of AN17, AN85, and AN80 also are included within the invention. Excluded from the invention are the naturally-occuring homologs of AN polypeptides and nucleic acids found in *S. cerevisiae* (D9798.4, L8543.16, YGR010W, and L8004.2), although methods employing such polypeptides and nucleic acids are encompassed by the invention.

The AN97, AN17, AN80, and AN85 genes have been identified and shown to be essential for survival, these AN polypeptides and their yeast homologs (e.g., D9798.4, L8543.16, YGR010W, and L8004.2) can be used to identify antifungal agents. More specifically, these AN polypeptides and their yeast homologs can be used, separately or together, in assays to identify test compounds which bind these polypeptides. Such test compounds are expected to be antifungal agents, in contrast to compounds that do not bind AN97, AN17, AN80, AN85, D9798.4, L8543.16, YGR010W, and/or L8004.2. As described herein, any of a variety of art-known methods can be used to assay for binding of test compounds to the polypeptides. The invention includes, for example, a method for identifying an antifungal or anti-yeast agent where the method entails: (a) contacting an AN polypeptide, or homolog thereof, with a test compound; (b) detecting binding of the test compound to the AN polypeptide or homolog; and (c) determining whether a test compound that binds the AN polypeptide or homolog inhibits growth of fungi or yeast, relative to growth of fungi or yeast cultured in the absence of the test compound that binds the AN polypeptide or homolog, as an indication that the test compound is an antifungal or anti-yeast agent.

In various embodiments, the AN polypeptide is derived from a non-pathogenic or pathogenic Aspergillus strain, such as *Aspergillus nidulans, Aspergillus fumigatus, Aspergillus flavus,* and *Aspergillus niger*. Preferably, homologs thereof are derived from the yeast *Saccharomyces cerevisiae*. The test compound can be immobilized on a substrate, and binding of the test compound to the AN polypeptide or homolog can be detected as immobilization of the AN polypeptide or homolog on the immobilized test compound, e.g., in an immunoassay with an antibody that specifically binds AN97.

If desired, the test compound can be a test polypeptide (e.g., a polypeptide having a random or predetermined amino acid sequence; or a naturally-occurring or synthetic polypeptide). Alternatively, the test compound can be a nucleic acid, such as a DNA or RNA molecule. In addition, small organic molecules can be tested. The test compound can be a naturally-occurring compound or it can be synthetically produced, if desired. Synthetic libraries, chemical libraries, and the like can be screened to identify compounds that bind the AN polypeptides. More generally, binding of test compound to the AN polypeptide or homolog can be detected either in vitro or in vivo. Regardless of the source of the test compound, the AN polypeptides described herein can be used to identify compounds that are fungicidal or fungistatic to a variety of pathogenic or non-pathogenic strains.

In an exemplary method, binding of a test compound to an AN polypeptide can be detected in a conventional two-hybrid system for detecting protein/protein interactions (e.g., in yeast or mammalian cells). Generally, in such a method, (a) the AN polypeptide is provided as a fusion protein that includes the AN polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the AN polypeptide polypeptide is detected as reconstitution of a transcription factor. The yeast homologs can be used in similar methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an AN polypeptides is used to identify a compound that decreases the expression of the AN polypeptide in vivo. Such compounds can be used as antifungal agents. To discover such compounds, cells that express an AN polypeptide are cultured, exposed to a test compound (or a mixture of test compounds), and the level of expression or activity is compared with the level of AN polypeptide expression or activity in cells that are otherwise identical but that have not been exposed to the test compound(s). Many standard quantitative assays of gene expression can be utilized in this aspect of the invention.

In order to identify compounds that modulate expression of an AN polypeptide (or homologous sequence), the test compound(s) can be added at varying concentrations to the culture medium of cells that express an AN polypeptide (or homolog), as described above. Such test compounds can include small molecules (typically, non-protein, non-polysaccharide chemical entities), polypeptides, and nucleic acids. The expression of the AN polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the AN polypeptide. Because the AN polypeptides are essential for survival, test compounds that inhibit the expression and/or function of the AN polypeptide will inhibit growth of the cells or kill the cells.

Compounds that modulate the expression of the polypeptides of the invention can be identified by carrying out the assay described above and then measuring the levels of the AN polypeptides expressed in the cells, e.g., by performing a Western blot analysis using antibodies that bind an AN polypeptide.

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of anti-fungal therapeutic agents. These antifungal agents reduce the action of the gene product in a wild type strain, and therefore are useful in treating a subject with that type, or a similarly susceptible type of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic fungus of the same genus or similar species), and the absence or divergence of the sequence in host cells can be determined, if desired. Therapeutic agents directed toward genes or gene products that are not present in the host have several advantages, including fewer side effects, and lower overall dosage.

The invention includes pharmaceutical formulations that include a pharmaceutically acceptable excipient and an antifungal agent identified using the methods described herein. In particular, the invention includes pharmaceutical formulations that contain antifungal agents that inhibit the growth of, or kill, pathogenic Aspergillus strains. Such pharmaceutical formulations can be used for treating an Aspergillus infection in an organism. Such a method entails administering to the organism a therapeutically effective amount of the pharmaceutical formulation. In particular, such pharmaceutical formulations can be used to treat aspergillosis in mammals such as humans and domesticated mammals (e.g., cows and pigs). The efficacy of such antifungal agents in humans can be estimated in an animal model system well known to those of skill in the art (e.g., bovine and rodent (e.g., mouse) model systems). These formulations also can be used to treat fungal infections in plants, e.g., by topically applying the antifungal agent to the plant. Alternatively, where the antifungal agent is a polypeptide or an antisense RNA, a gene encoding the polypeptide or expressing the antisense RNA can be transfected into the plant, using conventional techniques, and the polypeptide or antisense RNA can be expressed in the plant.

Also included within the invention are polyclonal and monoclonal antibodies that specifically bind AN97, AN17, AN80, or AN85 polypeptide. Such antibodies can facilitate detection of AN polypeptides in various Aspergillus strains.

These antibodies also are useful for detecting binding of a test compound to AN97, AN17, AN80, or AN85 polypeptides (e.g., using the assays described herein). In addition, monoclonal antibodies that bind AN97, AN17, AN80, or AN85 polypeptide are themselves adequate antifungal agents when administered to a mammal, as such monoclonal antibodies are expected to impede one or more functions of AN97, AN17, AN80, or AN85 polypeptide.

As used herein, "nucleic acids" encompass both RNA and DNA, including cDNA, genomic DNA, and synthetic (e.g., chemically synthesized) DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

A nucleic acid sequence that is "substantially identical" to an AN97, AN17, AN80, or AN85 nucleotide sequence is at least 80% or 85% identical to the nucleotide sequence of the Aspergillus AN97, AN80, AN85, and AN17 nucleic acids of SEQ ID NO:1, NO:4, NO:7, and NO:10, respectively, as depicted in FIGS. 1, 2, 3, and 4, respectively. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

The AN polypeptides of the invention include, but are not limited to, recombinant polypeptides and natural polypeptides. The invention also encompasses nucleic acid sequences that encode forms of AN97, AN17, AN80, or AN85 polypeptides in which naturally occurring amino acid sequences are altered or deleted. Preferred nucleic acids encode polypeptides that are soluble under normal physiological conditions. Also within the invention are nucleic acids encoding fusion proteins in which a portion of AN97, AN17, AN80, or AN85 is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes isolated, for example, polypeptides (and the nucleic acids that encode these polypeptides) that include a first portion and a second portion; the first portion includes, e.g., an AN polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode AN97, AN17, AN80, or AN85 fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequence of SEQ ID NO:1, NO:4, NO:7, or NO:10, or their complements. The hybridizing portion of the hybridizing nucleic acids is typically at least 15 (e.g., 20, 30, or 50) nucleotides in length. The hybridizing portion of the hybridizing nucleic acid is at least 80%, e.g., at least 95%, or at least 98%, identical to the sequence of a portion or all of a nucleic acid encoding an AN97, AN17, AN80, or AN85 polypeptide. Hybridizing nucleic acids of the type described herein can be used as a cloning probe, a primer (e.g., a PCR primer), or a diagnostic probe. Nucleic acids that hybridize to the nucleotide sequences of SEQ ID NO:1, NO:4, NO:7, or NO:10 are considered "antisense oligonucleotides." Also included within the invention are ribozymes that inhibit the function of AN97, AN17, AN80, or AN85, as determined, for example, in a complementation assay.

In another embodiment, the invention features cells, e.g., transformed host cells, that contain a nucleic acid encompassed by the invention. A "transformed cell" is a cell into which (or into an ancestor of which) has been introduced, by means of recombinant DNA techniques, a nucleic acid encoding an AN polypeptide. Both prokaryotic and eukaryotic cells are included, e.g., bacteria, Aspergillus, yeast, and the like.

The invention also features genetic constructs (e.g., vectors and plasmids) that include a nucleic acid of the invention which is operably linked to a transcription and/or translation sequence to enable expression, e.g., expression vectors. By "operably linked" is meant that a selected nucleic acid, e.g., a DNA molecule encoding an AN polypeptide, is positioned adjacent to one or more sequence elements, e.g., a promoter, which directs transcription and/or translation of the sequence such that the sequence elements can control transcription and/or translation of the selected nucleic acid.

The invention also features purified or isolated AN97, AN17, AN80, and AN85 polypeptides. As used herein, both "protein" and "polypeptide" mean any chain of amino acids, regardless of length or post-translational modification (e.g., glycosylation or phosphorylation). Thus, the terms "AN97 polypeptide" (or AN97), "AN17 polypeptide" (or AN17), "AN80 polypeptide" (or AN80), or "AN85 polypeptide" (or AN85) include full-length, naturally occurring AN97, AN17, AN80, or AN85 proteins, respectively, as well as recombinantly or synthetically produced polypeptides that correspond to a full-length, naturally occurring AN97, AN17, AN80, or AN85 protein, or to a portion of a naturally occurring or synthetic AN97, AN17, AN80, or AN85 polypeptide.

A "purified" or "isolated" compound is a composition that is at least 60% by weight the compound of interest, e.g., an AN97 polypeptide or antibody. Preferably the preparation is at least 75% (e.g., at least 90% or 99%) by weight the compound of interest. Purity can be measured by any appropriate standard method, e.g., column chromatography, polyacrylamide gel electrophoresis, or HPLC analysis.

Preferred AN97, AN17, AN80, AN85 polypeptides include a sequence substantially identical to all or a portion of a naturally occurring AN97, AN17, AN80, or AN85 polypeptide, e.g., including all or a portion of the sequences shown in FIGS. 1, 2, 3, and 4, respectively. Polypeptides "substantially identical" to the AN polypeptide sequences described herein have an amino acid sequence that is at least 80% or 85% (e.g., 90%, 95% or 99%) identical to the amino acid sequence of the AN97, AN80, AN85 or AN17 polypeptides of SEQ ID NOs:2 and 29; No:5; Nos:8, 30, 31, and 32; and NOs: 11, 33, 34, and 35, respectively. For purposes of comparison, the length of the reference AN polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to an AN polypeptide. By "specifically binds" is meant that an antibody recognizes and binds a particular antigen, e.g., an AN97, AN17 polypeptide, but does not substantially recognize and bind other molecules in a sample, e.g., a biological sample that naturally includes AN97, AN17, AN80, or AN85. In one embodiment the antibody is a monoclonal antibody.

In another aspect, the invention features a method for detecting an AN polypeptide in a sample. This method includes: obtaining a sample suspected of containing AN97, AN17, AN85, or AN80; contacting the sample with an antibody that specifically binds an AN97, AN17, AN85 or AN80 polypeptide under conditions that allow the formation of complexes of an antibody and AN97, AN17, AN85 or AN80; and detecting the complexes, if any, as an indication of the presence of AN97, AN17, AN85 or AN80 in the sample.

Also encompassed by the invention is a method of obtaining a gene related to (i.e., a functional homologue of) the AN97, AN17, AN85, or AN80 gene. Such a method entails obtaining a labeled probe that includes an isolated nucleic acid which encodes all or a portion of AN97, AN17, AN85, or AN80, or a homolog thereof (e.g., D9798.4, L8543.16, YGR010W, or L8004.2); screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the AN97, AN17, AN85, or AN80 gene.

The invention offers several advantages. By combining gene knockout assays, as described herein, with assays of conditional sensitivity, we have identified genes that are truly essential, i.e., genes whose absence is fungicidal to Aspergillus. In addition, the methods for identifying antifungal agents can be configured for high throughput screening of numerous candidate antifungal agents.

Other features and advantages of the invention will be apparent from the following detailed description, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

BRIEF DESCRIPTION OF THE DRAWINGS

FIGS. 1A to 1K are a representation of the amino acid and nucleic acid sequences of the AN97 polypeptide and gene from an *Aspergillus nidulans* strain (SEQ ID NOs:2 and 29; and NO:1, respectively). The non-coding sequence is set forth as SEQ ID NO:3.

FIGS. 2A to 2D are a representation of the amino acid and nucleic acid sequences of the AN80 polypeptide and gene from an *Aspergillus nidulans* strain (SEQ ID NOs:5 and 4, respectively). The non-coding sequence is set forth as SEQ ID NO:6.

FIGS. 3A to 3D are a representation of the amino acid and nucleic acid sequences of the AN85 polypeptide and gene from an *Aspergillus nidulans* strain (SEQ ID NOs:8, 30, 31, and 32; and NO:7, respectively). The non-coding sequence is set forth as SEQ ID NO:9.

FIGS. 4A to 4D are a representation of the amino acid and nucleic acid sequences of the AN17 polypeptide and gene from an *Aspergillus nidulans* strain (SEQ ID NOs:11, 33, 34, and 35; and NO:10, respectively). The non-coding sequence is set forth as SEQ ID NO:12.

FIGS. 5A to 5H are a representation of the amino acid and nucleic acid sequences of the D9798.4 polypeptide and gene from *S. cerevisiae* (SEQ ID NOs:14 and 13, respectively). The non-coding sequence is set forth as SEQ ID NO:15.

FIGS. 6A to 6D are a representation of the amino acid and nucleic acid sequences of the YGR010W polypeptide and gene from *S. cerevisiae* (SEQ ID NOs:17 and 16, respectively). The non-coding sequence is set forth as SEQ ID NO:18.

FIGS. 7A to 7G are a representation of the amino acid and nucleic acid sequences of the L8543.16 polypeptide and gene from *S. cerevisiae* (SEQ ID NOs:20 and 19, respectively). The non-coding sequence is set forth as SEQ ID NO:21.

FIGS. 8A to 8D are a representation of the amino acid and nucleic acid sequences of the L8004.2 polypeptide and gene from *S. cerevisiae* (SEQ ID NOs:23 and 22, respectively). The non-coding sequence is set forth as SEQ ID NO:24.

DETAILED DESCRIPTION OF THE INVENTION

Identifying Essential Aspergillus Genes

As shown by the experiments described below, expression of each of the AN97, AN17, AN80, and AN85 polypeptides is essential for survival of *Aspergillus nidulans*. *Aspergillus nidulans* is available from the ATCC (#FGSC4). To identify genes for which inhibition of gene expression is fungicidal, various mutants of *Aspergillus nidulans* were assayed for conditional sensitivity. In general, mutagenesis of *Aspergillus nidulans* can be accomplished using any of various art-known methods. For example, exposure to ultraviolet light, x-rays, and/or chemical mutagens is acceptable. Examples of suitable chemical mutagens include ethylmethansulfonate (EMS), metyhlmethanesulfonate (MMS), methylnitrosoguanidine (NTG), 4-nitroquinoline-1-oxide (NQO), 2-aminopurine, 5-bromouracil, ICR 191 and other acridine derivatives, sodium bisulfite, ethidium bromide, nitrous acid, hydroxylamine, N-methyl-N'-nitroso-N-nitroguanidine, and alkylating agents (for further description of art-known mutagens and mutagenesis methods, see, e.g., Current Protocols in Molecular Biology, 1995 and Adelberg et al., *Biochem. Biophys. Res. Comm.* 18:788, 1965).

To identify conditional-sensitive mutants, mutagenized cells can be grown under (a) a first set of permissive conditions, then shifted to (b) restrictive conditions, and then to (c) a second set of permissive conditions. The cells of interest are those mutants that grow under the permissive conditions of (a), but fail to grow under the restrictive conditions of (b), and fail to recover under the permissive conditions of (c).

Ostensibly, any change in a growth parameter can serve as the "restrictive condition." For example, the restrictive conditions may be met by increasing or decreasing the temperature at which the cells are grown, thereby allowing the identification of temperature-sensitive mutants. For example, the optimal growth temperature for *A. nidulans* is 28° C., and a typical restrictive temperature is 42° C. In alternative methods, the change to a restrictive condition may entail changing one or more of the following parameters of the growth conditions: pH, type and/or concentration of carbon and nitrogen sources, trace minerals, vitamins, salts, conidia-forming materials (e.g., DMSO, glycerol, and deuterated water), humidity, and the like. In general, permissive growth conditions allow the strains to grow at a rate that is at least 75% of that of the wild-type growth rate of Aspergillus. The second set of permissive conditions (in (c)) can be the same as, or different from, the first permissive conditions. Typically, the cells are subjected to the second permissive conditions for at least 2 growth cycles (more typically, at least 5, 10, 15 or even 20 growth cycles). Generally, the cells are subjected to the restrictive conditions for 2 to 20 growth cycles (typically 2–10 growth cycles) and for 24 hours or less.

In practicing the invention, cell death (e.g., in (b)) can be detected using any of a number of conventional criteria. For example, cell death can be detected macroscopically by observing that a colony of cells has approximately the same size, or a reduced size, after a length of time that is normally sufficient for several growth cycles under the second permissive conditions. Detection of cell death also can be facilitated by the use of light microscopy and cell staining to reveal cytological deformations and/or morphologies commonly known to be indicative of cell death. The absence of DNA, RNA, or protein synthesis also can signify cell death.

Identification of Homologs of AN Polypeptides

Having shown that the AN97, and AN80, and AN85 genes and polypeptides are essential for survival in Aspergillus, it can be expected that homologs of these polypeptides, when present in other organisms, for example pathogenic yeast, are essential for survival of those organisms as well. Using the sequences of the AN polypeptides identified in Aspergillus, homologs of these polypeptides were identified in the yeast *S. cerevisiae*. The coding sequences of AN97, AN80, and AN85 were used to search the GenBank database of nucleotide sequences to identify homologs of AN97, AN80, and AN85, respectively, which are essential genes in other organisms. Sequence comparisons were performed using the Basic Local Alignment Search Tool (BLAST) (Altschul et al., *J. Mol. Biol.*, 215:403–410 1990). The percent sequence identity shared by the AN polypeptides and their homologs were determined using the GAP program from the Genetics Computer Group (GCG) Wisconsin Sequence Analysis Package (Wisconsin Package Version 9.0, GCG; Madison, Wis.). The following parameters were used: gap creation penalty, 12 (protein) 50 (DNA); gap extension penalty, 4 (protein) 3 (DNA). The percent sequence identity shared by the AN polypeptides and their homologs are summarized in Table 1. Typically, the AN polypeptides and their homologs share at least 25% (e.g., at least 40%) sequence identity. Typically, the DNA sequences encoding AN polypeptides and their homologs share at least 35% (e.g., at least 45%) sequence identity.

TABLE 1

Sequence Identity Shared by AN Polypeptides and Their Homologues.

| AN Polypeptide | Homolog in Saccharomyces | % Identity of DNA Sequences (coding region) | % Identity of Polypeptide Sequences |
|---|---|---|---|
| AN80 | L8004.2 | 37.4 | 27.9 |
| AN85 | YGR010W | 50.2 | 41.0 |
| AN85 | L8543.16 | 49.2 | 43.7 |
| AN97 | D9798.4 | 38.7 | 25.8 |

To confirm that these yeast homologs of the AN polypeptides are essential for survival of yeast, the gene encoding each of the homologs was, separately, deleted from the *S. cerevisiae* genome. To this end, standard methods for making yeast "knock outs" were used, as described by Baudin et al., *Nucl. Acids. Res.* 21:3329–3330, 1993. Briefly, a portion of the yeast genome was amplified in a polymerase chain reaction (PCR) that employed two primers. The primers for L8004.2 were 5'AGGAAAGTAGCTATCGTAACGGG-TACTAATAGTAA TCTTGGTCTCTTGGCCTC-CTCTAG3' (SEQ ID NO: 25) and 5'TACGCA-GAGATATATTAAA
TGGGGGTTCTAGTTTCAACAATTTCGT-TCAGAATGACACG3' (SEQ ID NO:26). The primers for D9798.4 were 5'TTAACAGCCGCGCCCATCATGCAA-GATCCTGATGGTATTGACA TTCTCTTGGCCTC-CTCTAG3' (SEQ ID NO:27) and 5'GCATATCAATTTTAA-CAGACCTCGCTG
AAAGACTCTGAATCCTCGTTCAGAATGACACG3'

(SEQ ID NO:28). These primers hybridized to a portion of the 5' and 3' sequences flanking the open reading frames of the yeast homologs and include nucleotides that are homologous to the HIS3 selectable marker. Following PCR amplification, the resulting crude mix was directly used to transform yeast, following a standard protocol.

Identification of AN97, AN17, AN80, and AN85 Genes in Additional Aspergillus Strains Now that the AN97, AN80, AN17, and AN85 genes and their yeast homologs, L8004.2, YGR010W, L8543.16, and D9798.4, have been identified as essential for survival (as described below under "Examples"), these genes, or fragments thereof, can be used to detect homologous essential genes in other organisms. In particular, these genes can be used to analyze various pathogenic and non-pathogenic strains of Aspergillus (e.g., *Aspergillus fumigatus, Aspergillus flavus* and *Aspergillus niger*) and yeast (e.g., *Candida albicans*). In particular, fragments of a nucleic acid (DNA or RNA) encoding an AN polypeptide or yeast homolog (or sequences complementary thereto) can be used as probes in conventional nucleic acid hybridization assays of pathogenic organisms (e.g., pathogenic Aspergillus strains). For example, nucleic acid probes (which typically are 8–30, or usually 15–20, nucleotides in length) can be used to detect the AN97, AN17, AN80, AN85 genes or homologs thereof in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library or a cDNA library constructed from mRNA obtained from an Aspergillus or yeast strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the cDNA library, or other nucleic acid sample, typically is performed under moderate to high stringency conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by 5° C.). In practice, the change in $T_m$ can be between 0.5° and 1.5° C. per 1% mismatch.

As used herein, high stringency conditions include, for example, hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, cDNA libraries constructed from pathogenic or non-pathogenic Aspergillus or yeast strains can be screened. For example, such strains can be screened for AN97, AN17, AN85, or AN80 expression by Northern blot analysis. Upon detection of AN97, AN17, AN85, or AN80 transcripts or transcripts of homologs thereof, cDNA libraries can be constructed from RNA isolated from the appropriate strain, utilizing standard techniques well known to those of skill in the art. Alternatively, a total genomic DNA library can be screened using an AN97, AN17, AN85, or AN80 probe (or a probe directed to a homolog thereof).

New gene sequences can be isolated, for example, by performing PCR using two degenerate oligonucleotide primer pools designed on the basis of nucleotide sequences within the AN97, AN17, AN85 or AN80 genes, or their homologs, as depicted herein. The template for the reaction can be cDNA obtained by reverse transcription of mRNA prepared from strains known or suspected to express an AN97, AN17, AN85, or AN80 allele or an allele of a homolog thereof. The PCR product can be subcloned and sequenced to ensure that the amplified sequences represent the sequences of a new AN97, AN17, AN85, or AN80 nucleic acid sequence, or a sequence of a homolog thereof.

The PCR fragment can then be used to isolate a full length cDNA clone by a variety of known methods. For example, the amplified fragment can be labeled and used to screen a bacteriophage cDNA library. Alternatively, the labeled fragment can be used to screen a genomic library.

PCR technology also can be used to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Now that the AN97, AN17, AN85, and AN80 genes and their homologs have been cloned, synthesis of the AN polypeptides or their homologs (or an antigenic fragment thereof) for use as antigens, or for other purposes, can readily be accomplished using any of the various art-known techniques. For example, an AN polypeptide or homolog, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or insect cells (e.g., by using a baculovirus-based expression vector).

Proteins and polypeptides can also be produced in plant cells, if desired. For plant cells viral expression vectors (e.g., cauliflower mosaic virus and tobacco mosaic virus) and plasmid expression vectors (e.g., Ti plasmid) are suitable.

Such cells are available from a wide range of sources (e.g., the American Type Culture Collection, Rockland, Md.; also, see, e.g., Ausubel et al., *Current Protocols in Molecular Biology,* John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors:* A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, AN polypeptides or their homologs can be produced as fusion proteins. For example, the expression vector pUR278 (Ruther et al., *EMBO J.,* 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary insect cell expression system, a baculovirus such as *Autographa californica* nuclear polyhedrosis virus (AcNPV), which grows in *Spodoptera frugiperda* cells, can be used as a vector to express foreign genes. A coding sequence encoding an AN polypeptide or homolog can be cloned into a non-essential region (for example the polyhedrin gene) of the viral genome and placed under control of a promoter, e.g., the polyhedrin promoter or an exogenous promoter. Successful insertion of a gene encoding an AN polypeptide or homolog can result in inactivation of the polyhedrin gene and production of non-occluded recombinant virus (i.e., virus lacking the proteinaceous coat encoded by the polyhedrin gene). These recombinant viruses are then used to infect insect cells (e.g., *Spodoptera frugiperda* cells) in which the inserted gene is expressed (see, e.g., Smith et al., *J. Virol.,* 46:584, 1983; Smith, U.S. Pat. No. 4,215,051).

In mammalian host cells, a number of viral-based expression systems can be utilized. When an adenovirus is used as an expression vector, the nucleic acid sequence encoding the AN polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an AN97, AN17, AN85, or AN80 gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In cases where an entire native gene (e.g., AN97) or cDNA, including its own initiation codon and adjacent sequences, is inserted into the appropriate expression vector, no additional translational control signals may be needed. In other cases, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., Methods in Enzymol., 153:516, 1987).

The AN polypeptides and homologs can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the AN polypeptide or homolog thereof can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, cDNA encoding the protein is cloned into an expression vector that includes the dihydrofolate reductase (DHFR) gene. Integration of the plasmid and, therefore, the AN polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA,* 78:2072, 1981); neo, which confers resistance to the aminoglycoside G-418 (Colberre-Garapin et al., *J. Mol. Biol.,* 150:1, 1981); and hygro, which confers resistance to hygromycin (Santerre et al., *Gene,* 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, an AN polypeptide or homolog, or a portion thereof, can be fused to an immunoglobulin Fc domain. Such a fusion protein can be readily purified using a protein A column, for example. Moreover, such fusion proteins permit the production of a chimeric form of an AN polypeptide or homolog having increased stability in vivo.

Once the recombinant AN polypeptide (or homolog) is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-AN97 antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an AN polypeptide (e.g., an AN97-maltose binding fusion protein, an AN97-β-galactosidase fusion protein, or an AN97-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of AN97, AN17, AN85, ANSO from pathogenic Aspergillus strains, and fragments of D9798.4, L8004.2, L8543.16, and YGR010W from yeast, can be produced by standard chemical synthesis (e.g., by the methods described in *Solid Phase Peptide Synthesis*, 2nd ed., The Pierce Chemical Co., Rockford, Ill., 1984) and used as antigens, for example.

Antibodies

AN97, AN17, AN85, or AN80 polypeptides (or antigenic fragments or analogs of such polypeptide) can be used to raise antibodies useful in the invention, and such polypeptides can be produced by recombinant or peptide synthetic techniques (see, e.g., *Solid Phase Peptide Synthesis*, supra; Ausubel et al., supra). Likewise, antibodies can be raised against the yeast homologs. In general, the polypeptides can be coupled to a carrier protein, such as KLH, as described in Ausubel et al., supra, mixed with an adjuvant, and injected into a host mammal. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies (mAbs), which are homogeneous populations of antibodies to a particular antigen, can be prepared using the AN polypeptides or homologs thereof and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of an AN polypeptide or homolog thereof in an immunoassay, such as a Western blot or immunoprecipitation analysis using standard techniques, e.g., as described in Ausubel et al., supra. Antibodies that specifically bind to AN97, AN17, AN85, or AN80, or conservative variants and homologs thereof, are useful in the invention. For example, such antibodies can be used in an immunoassay to detect AN97 in pathogenic or non-pathogenic strains of Aspergillus (e.g., in Aspergillus extracts).

Preferably, antibodies of the invention are produced using fragments of the AN polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant AN polypeptide or homolog, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; and 4,946,778 and 4,704,692) can be adapted to produce single chain antibodies against an AN polypeptide or homolog. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind AN polypeptides or homologs can be used, for example, to detect expression of an AN97, AN17, AN85, AN80 gene or homolog in another strain of Aspergillus. For example, AN97 polypeptide can be readily detected in conventional immunoassays of Aspergillus cells or extracts. Examples of suitable assays include, without limitation, Western blotting, ELISAs, radioimmune assays, and the like.

Assay for Antifungal Agents

The invention provides a method for identifying an antifungal agent(s). Although the inventors are not bound by any particular theory as to the biological mechanism involved, the new antifungal agents are thought to inhibit specifically the function of the AN polypeptides or expression of the AN97, AN17, AN85, or AN80 genes, or homologs thereof. Screening for antifungal agents can be rapidly accomplished by identifying those compounds (e.g., polypeptides, ribonucleic acids (including ribozymes), nucleic acids (including antisense nucleic acids), or small molecules) that specifically bind to an AN polypeptide. A homolog of an AN polypeptide (e.g., D9798.4, L8004.2, L8543.16, or YGR010W) can be substituted for the AN polypeptide in the methods summarized herein. Specific binding of a test compound to an AN polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with an AN polypeptide (or a combination of AN polypeptides and/or homologs) by adding the polypeptide(s) in a solution (typically, at a concentration of 0.05 to 1 mg/ml in a volume of 1–100 µl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the AN polypeptide or homolog is contained in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the new AN polypeptides (or homologs thereof) can be detected by any of a variety of art-known methods. For example, an antibody that specifically binds an AN polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-AN97 antibody). In an alternative detection method, the AN polypeptide is labeled, and the label is detected (e.g., by labeling an AN polypeptide with a radioisotope, fluorophore, chromophore, or the like). In still another method, the AN polypeptide is produced as a fusion protein with a protein that can be detected optically, e.g., green fluorescent protein (which can be detected under UV light). In an alternative method, the AN polypeptide can be produced as a fusion protein with an enzyme having a detectable enzymatic activity, such as horse radish peroxidase, alkaline phosphatase, α-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and α-galactosidase) and non-enzymatic polypeptides (e.g., serum proteins, such as BSA and globulins, and milk proteins, such as caseins).

In various in vivo methods for identifying polypeptides that bind AN polypeptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Kits for practicing various two-hybrid methods are commercially available (e.g., from Clontech; Palo Alto, Calif.).

Generally, the two-hybrid methods involve in vivo reconstitution of two separable domains of a transcription factor. The DNA binding domain (DB) of the transcription factor is required for recognition of a chosen promoter. The activation domain (AD) is required for contacting other components of the host cell's transcriptional machinery. The transcription factor is reconstituted through the use of hybrid proteins. One hybrid is composed of the AD and a first protein of interest. The second hybrid is composed of the DB and a second protein of interest. In cases where the first and second proteins of interest interact with each other, the AD and DB are brought into close physical proximity, thereby reconstituting the transcription factor. Association of the proteins can be measured by assaying the ability of the reconstituted transcription factor to activate transcription of a reporter gene.

Useful reporter genes are those that are operably linked to a promoter which is specifically recognized by the DB. Typically, the two-hybrid system employs the yeast *Saccharomyces cerevisiae* and reporter genes, the expression of which can be selected under appropriate conditions. Other eukaryotic cells, including mammalian and insect cells, can be used, if desired. The two-hybrid system provides a convenient method for cloning a gene encoding a polypeptide (i.e., a candidate antifungal agent) that binds a second, preselected polypeptide (e.g., AN97). Typically, though not necessarily, a cDNA library is constructed such that randomly generated sequences are fused to the AD, and the protein of interest (e.g., AN97 or AN80) is fused to the DB.

In such two-hybrid methods, two fusion proteins are produced. One fusion protein contains the AN polypeptide (or homolog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the AN polypeptide to the test polypeptide (i.e., candidate antifungal agent) reconstitutes the transcription factor. Reconstitution of the transcription factor can be detected by detecting expression of a gene (i.e., a reporter gene) that is operably linked to a DNA sequence that is bound by the DNA binding domain of the transcription factor.

The methods described above can be used for high throughput screening of numerous test compounds to identify candidate antifungal (or anti-yeast) agents. Having identified a test compound as a candidate antifungal agent, the candidate antifungal agent can be further tested for inhibition of fungal growth in vitro or in vivo (e.g., using an animal, e.g., rodent, model system) if desired. Using other, art-known variations of such methods, one can test the ability of a nucleic acid (e.g., DNA or RNA) used as the test compound to bind an AN polypeptide or homolog thereof.

In vitro, further testing can be accomplished by means known to those in the art such as an enzyme inhibition assay or a whole-cell fungal growth inhibition assay. For example, an agar dilution assay identifies a substance that inhibits fungal growth. Microtiter plates are prepared with serial dilutions of the test compound; adding to the preparation a given amount of growth substrate; and providing a preparation of Aspergillus spores. Inhibition of growth is determined, for example, by observing changes in optical densities of the fungal cultures.

Inhibition of fungal growth is demonstrated, for example, by comparing (in the presence and absence of a test compound) the rate of growth or the absolute growth of fungal sporulation or nuclei. Inhibition includes a reduction of one of the above measurements by at least 20% (e.g., at least 25%, 30%, 40%, 50%, 75%, 80%, or 90%).

Rodent (e.g., murine) and bovine animal models of aspergillosis are known to those of skill in the art, and such animal model systems are accepted for screening antifungal agents as an indication of their therapeutic efficacy in human patients (Rhodes et al., *J. Med. and Vet. Myco.*, 30:51–57, 1992). Indeed, the clinical manifestations of bovine aspergillosis show many pathological similarities to aspergillosis in humans and rodents. In a typical in vivo assay, an animal is infected with a pathogenic Aspergillus strain, e.g., by inhalation of Aspergillus spores (i.e., conidia), and conventional methods and criteria are used to diagnose the mammal as being afflicted with aspergillosis. The candidate antifungal agent then is administered to the mammal at a dosage of 1–100 mg/kg of body weight, and the mammal is monitored for signs of amelioration of disease. Alternatively, the test compound can be administered to the mammal prior to infecting the mammal with Aspergillus, and the ability of the treated mammal to resist infection is measured. Of course, the results obtained in the presence of the test compound are compared with results in control animals, which are not treated with the test compound. Administration of candidate antifungal agent to the mammal can be carried out as described below, for example.

Antisense Methods

Antisense approaches involve the design of oligonucleotides (either DNA or RNA) that are complementary to AN97, AN17, AN80, or AN85 mRNA. The antisense oligonucleotides bind to the AN97, AN17, AN80, or AN85 coding sequences and/or mRNA transcripts and inhibit transcription and/or translation. Absolute complementarity is not required. A sequence "complementary" to a portion of an RNA, as referred to herein, means a sequence having sufficient complementarity to be able to hybridize with the RNA and form a stable duplex; in the case of double-stranded antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (Wagner, *Nature*, 372:333, 1984). Thus, oligonucleotides complementary to either the 5'- or 3'- non-translated, non-coding regions of the AN97, AN17, AN80, or AN85 genes, or their yeast homologs D9798.4, L8543.16, YGR010W, of L8004.2, as represented by SEQ ID NOs:1, 4, 7, 10, 13, 16, 19, and 22 can be used in an antisense approach to inhibit translation of the endogenous sequences. Oligonucleotides complementary to the 5' untranslated region of the mRNA typically also include the complement of the AUG start codon.

Antisense oligonucleotides complementary to mRNA coding regions are less preferred inhibitors of translation, but can be used in accordance with the invention. Whether designed to hybridize to the 5'-, 3'-, or coding region of the mRNA, antisense nucleic acids should be at least six nucleotides in length (e.g., oligonucleotides ranging from 6 to about 50 nucleotides in length). In specific aspects, the oligonucleotide is at least 10 nucleotides, at least 15 nucleotides, or at least 25 nucleotides.

Regardless of the choice of target sequence, in vitro studies typically are first performed to quantitate the ability of the antisense oligonucleotide to inhibit gene expression. Typically, these studies utilize controls that distinguish between antisense gene inhibition and nonspecific biological effects of oligonucleotides. Generally, these studies compare levels of the target RNA or protein with that of an internal control RNA or protein. Additionally, it is envisioned that results obtained using the antisense oligonucleotide are compared with those obtained using a control oligonucleotide. Typically, the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA, or chimeric mixtures, or derivatives or modified versions thereof, and can be single-stranded or double-stranded. The oligonucleotides can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA*, 86:6553, 1989; Lemaitre et al., *Proc. Natl. Acad. Sci. USA*, 84:648, 1987; PCT Publication No. WO 88/09810) or the blood-brain barrier (see, e.g., PCT Publication No. WO 89/10134), or hybridization-triggered cleavage agents (see, e.g., Krol et al., *BioTechniques*, 6:958, 1988), or intercalating agents (see, e.g., Zon, *Pharm. Res.*, 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropyl) uracil, (acp3) w, and 2,6-diaminopurine.

The antisense oligonucleotide can also include at least one modified sugar moiety selected from the group including, but not limited to, arabinose, 2-fluoroarabinose, xylulose, and hexose.

In yet another embodiment, the antisense oligonucleotide includes at least one modified phosphate backbone, e.g., a phosphorothioate, a phosphorodithioate, a phosphoramidothioate, a phosphoramidate, a phosphorodiamidate, a methylphosphonate, an alkyl phosphotriester, and a formacetal, or an analog of any of these backbones.

In addition, the antisense oligonucleotide can be an α-anomeric oligonucleotide that forms specific double-stranded hybrids with complementary RNA in which, contrary to the usual β-units, the strands run parallel to each other (Gautier et al., *Nucl. Acids. Res.*, 15:6625, 1987). The oligonucleotide can be a 2'-O-methylribonucleotide (Inoue et al., *Nucl. Acids Res.*, 15:6131, 1987), or a chimeric RNA-DNA analog (Inoue et al., *FEBS Lett.*, 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al., *Nucl. Acids Res.*, 16:3209, 1988, and methylphosphonate oligonucleotides can be prepared by use of controlled pore glass polymer supports (Sarin et al., *Proc. Natl. Acad. Sci. USA*, 85:7448, 1988).

While antisense nucleotides complementary to the AN97, AN17, AN80, AN85, D9798.4, L8543.16, YGR010W, or L8004.2 coding region sequence could be used, those complementary to the transcribed untranslated region are preferred. Generally, such antisense oligonucleotides are 10–100 nucleotides in length (e.g., 15–50 nucleotides). Pathogenic microorganisms, such as Aspergillus, can spontaneously phagocytose oligonucleotides. Accordingly, these antisense oligonucleotides can be administered systemically or locally to a patient suffering from a pathogen infection in order to deliver the antisense oligonucleotides to the infectious organism in a method of treatment. For example, such antisense oligonucleotides can be used to inhibit expression of an AN polypeptide and thereby treat or inhibit fungal infections. A suitable approach uses a recombinant DNA construct in which the antisense oligonucleotide is placed under the control of a strong pol III or pol II promoter. The use of such a construct to transfect fungal cells in the patient will result in the transcription of sufficient amounts of single stranded nucleic acids that form complementary base pairs with the endogenous transcripts encoding AN polypeptides and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Appropriate vectors can be constructed by recombinant DNA technology methods standard in the art. Vectors can be plasmid, viral, or others known in the art, used for replication and expression in fungal cells. Expression of the sequence encoding the antisense RNA can be by any promoter known in the art to act in fungi, e.g. Aspergillus, cells. Such promoters can be inducible or constitutive, such as an alcohol dehydrogenase promoter (e.g., alcA) and a nitrate reductase promoter (e.g., niiA). Any type of plasmid, cosmid, or viral vector can be used to prepare the recombinant DNA construct which can be administered systemically or directly to the infected tissue.

Ribozymes

Ribozyme molecules designed to catalytically cleave mRNA transcripts encoding AN polypeptides also can be used to prevent translation of mRNA and expression of the AN polypeptides (see, e.g., PCT Publication WO 90/11364; Saraver et al., *Science*, 247:1222, 1990). Various ribozymes that cleave mRNA at site-specific recognition sequences can be used to destroy mRNAs encoding the AN polypeptides (e.g., the use of hammerhead ribozymes). Hammerhead ribozymes cleave mRNAs at locations dictated by flanking regions that form complementary base pairs with the target mRNA. It is recommended that the target mRNA have the following sequence of two bases: 5'-UG-3'. The construction and production of hammerhead ribozymes is known in the art (Haseloff et al., *Nature*, 334:585, 1988). There are numerous examples of potential hammerhead ribozyme cleavage sites within the nucleotide sequence of cDNAs encoding AN polypeptides (FIGS. 1 to 3). Typically, the ribozyme is engineered so that the cleavage recognition site is located near the 5' end of the mRNA encoding the AN polypeptide in order to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., *Science,* 224:574, 1984; Zaug et al., *Science,* 231:470, 1986; Zug et al., *Nature,* 324:429, 1986; PCT Application No. WO 88/04300; and Been et al., *Cell,* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in AN polypeptides.

As in the antisense approach, the ribozymes can be composed of modified oligonucleotides (e.g., for improved stability, targeting, etc.), and should be delivered to cells that express the AN polypeptide. A typical method of delivery involves using a DNA construct "encoding" the ribozyme under the control of a strong constitutive promoter, e.g., a pol III or pol II promoter, so that transfected cells will produce sufficient quantities of the ribozyme to destroy endogenous mRNAs encoding AN polypeptides and inhibit translation thereof. Because ribozymes, unlike typical antisense molecules, are catalytic, a lower intracellular concentration is required for efficiency.

Pharmaceutical Formulations

Treatment includes administering a pharmaceutically effective amount of a composition containing an antifungal agent to a subject in need of such treatment, thereby inhibiting fungal growth in the subject. Such a composition typically contains from about 0.1 to 90% by weight (such as 1 to 20% or 1 to 10%) of an antifungal agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antifungal agent in each pharmaceutical formulation varies according to the formulation itself and the therapeutic effect desired in the specific pathologies and correlated therapeutic regimens. Appropriate dosages of the antifungal agents can readily be determined by those of ordinary skill in the art of medicine by monitoring the mammal for signs of disease amelioration or inhibition, and increasing or decreasing the dosage and/or frequency of treatment as desired. The optimal amount of the antifungal compound used for treatment of conditions caused by or contributed to by fungal infection may depend upon the manner of administration, the age and the body weight of the subject and the condition of the subject to be treated. Generally, the antifungal compound is administered at a dosage of 1 to 100 mg/kg of body weight, and typically at a dosage of 1 to 10 mg/kg of body weight.

EXAMPLE

In this example, the identification and cloning of AN97, AN17, AN85, and AN80 are described.

A library of approximately 1,000 *A. nidulans* mutants was obtained, which was prepared using 4-nitroquinoline as a mutagen, as described previously (Harris et al., *Genetics* 136:517–532 1994). To identify strains having a temperature-sensitive mutation in an essential gene, the collection of 1,000 strains was grown at the permissive temperature of 28° C. for 16 hours in minimal medium (MN; pH 6.5, 1% glucose, nitrate salts and trace elements as described in Kafer, *Adv. Genet.* 19:33–131, 1977). The trace element solution was stored at 4° in the dark; each liter contained 40 mg $Na_2B_4O_7$ (10 $H_2O$), 400 mg cupric sulfate (5 $H_2O$), 1 g ferric phosphate (4 $H_2O$), 600 mg manganese sulfate (4 $H_2O$), 800 mg disodium molybdate (2 $H_2O$), and 8 g zinc sulfate (7 $H_2O$). Salt solution was stored at 4° C. after adding 2 ml chloroform as a preservative; each liter contained 26 g potassium chloride, 26 g magnesium sulfate (7 $H_2O$) 76 g monobasic potassium phosphate and 50 mL trace element solution. Supplement solution was sterilized by autoclaving for 15 minutes and stored in a light-proof container due to the reactivity of riboflavin. Each liter contains 100 mg nicotinic acid, 250 mg riboflavin, 200 mg pantothenic acid, 50 mg pyridoxin, 1 mg biotin, and 20 mg p-aminobenzoic acid.

Conidia ($2 \times 10^6$/ml in sterile, distilled water) were mutagenized with NQO (4 µg/ml) for 30 minutes at 37° C. with constant shaking. Diluting the conidia with an equal volume of 5% sodium thiosulfate inactivated the NQO. Mutagenized conidia were diluted and plated onto CM+TRITON X-100 plates (from Union Carbide Chemicals,) and incubated at 28° C. for 3 days. Colonies were replica plated and the replica plated plates were incubated at 28° C. and 42° C. Putative temperature-sensitive mutants were picked and retested, then stored as a colony plug in 15% glycerol at −70° C.

The cells were replica plated and shifted to 42° C. for 24 hours. Strains that grew poorly or not at all were selected, because they were most likely to represent strains having a mutation in an essential gene. After 1 round of subjecting the collection of cells to the temperature shift, approximately 100 strains (10% of the strains) were identified as having failed to recover once they were shifted to the second permissive temperature. These 100 strains were again grown at a first permissive temperature, followed by 24 hours at 42° C., and 24 or 48 hours at 28° C. (the second permissive temperature). After this second round of selection, 10 strains were identified as having failed to recover, and therefore as containing a temperature sensitive mutation in an essential gene.

Complementation analysis was used to identify the essential gene containing the mutation for each strain. Each of the 10 mutant strains was transformed, separately, with an Aspergillus genomic cosmid library containing an ArgB marker in a pCosAx vector (Adams et al., *FEMS Microbiol. Lett.*, 122:227–231 1994). The strains were grown for 3–4 days at 28° C., replica plated, and shifted to 42° C. for a maximum of 3 days. Strains that grew were collected, and the cosmid DNA was packaged by "selfing" the organism to force it to undergo meiosis. In this method, a colony is picked and grown on a separate plate (which typically is sealed to prevent contamination). The resulting spores then are picked and grown in liquid culture, prior to isolating the DNA. The cosmid was packaged using GIGAPACK III Gold packaging system (Stratagene; La Jolla, Calif.), which produced plasmids that were subsequently isolated, purified, and used to transform bacteria for amplification, isolation, purification, and sequencing.

In one of the resulting strains, the mutation was in a gene designated "AN97," indicating that in *A. nidulans* this gene is essential for survival. The amino acid sequence of the AN97 polypeptide and the AN97 gene of *A. nidulans* are provided in FIG. 1 as SEQ ID NOs:2 and 29; and NO:1, respectively.

In a second strain, the mutation was in a gene designated "AN80," indicating that this gene is essential for survival. The AN80 amino acid and nucleic acid sequences are shown in FIG. 2 as SEQ ID NOs:5 and 4, respectively.

In a third strain, the mutation was in a gene designated "AN85," indicating that this gene is essential for survival. The AN85 amino acid and nucleic acid sequences are shown in FIG. 3 as SEQ ID NOs:8, 30, 31, and 32; and NO:7, respectively.

In a fourth strain, the mutation was in a gene designated "AN17," indicating that this gene is essential for survival. The AN17 amino acid and nucleic acid sequences are shown in FIG. 4 as SEQ ID NOs:11, 33, 34, and 35; and NO:10, respectively.

Now that each of these genes is known to be essential for survival of Aspergillus; the AN polypeptides (AN97, AN17, AN80, and AN85) can be used to identify antifungal agents by using the assays described herein. Other art-known assays to detect interactions of test compounds with proteins, or to detect inhibition of fungal growth also can be used with the AN97, AN17, AN80, and AN85 genes and gene products and homologs thereof.

Other Embodiments

The invention also features fragments, variants, analogs, and derivatives of the AN polypeptides described above that retain one or more of the biological activities of the AN polypeptides, e.g., as determined in a complementation assay. Also included within the invention are naturally-occurring and non-naturally-occurring allelic variants. Compared with the naturally-occurring AN97, AN80, AN85, and AN17 nucleotide sequences depicted in FIGS. 1, 2, 3, and 4 respectively, the nucleic acid sequence encoding allelic variants may have a substitution, deletion, or addition of one or more nucleotides. The preferred allelic variants are functionally equivalent to an AN polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 35

<210> SEQ ID NO 1
<211> LENGTH: 5596
<212> TYPE: DNA
<213> ORGANISM: Aspergillus nidulans
<220> FEATURE:
<221> NAME/KEY: CDS
<222> LOCATION: (604)...(2655)
<221> NAME/KEY: CDS
<222> LOCATION: (2706)...(3992)

<400> SEQUENCE: 1
agcgctgcgc agggcagctg tggcaaatcg ccggacgctt tggcgaaaca tcctgtcaat      60
atcaatgctg ctcctgaaac agaaaaagac aagacgaagt tccccggatt gtatctcgaa     120
tgaggggacc gatttccggc gttagtaaga ggtcacgtga aagatggcgt gctaactagt     180
atgcaaggca tttcggctca ggcaaaatac ccagtcaaca atttgttgcc tggaggtgga     240
aatacgagac ccttgattgc gagcagtgtg tgattaggat agctgaggca ttgtattcat     300
```

-continued

```
gtatcaggaa cctgatcgtc aaagcgttgc aggctgctgg gctgggcacg tgctgccta     360 acccttatct atctactggt ttggggtgtt tgtttatgct ccgccccgtg actctcagca    420
acggttataa cgagtagtgg cagcagccaa cgaacttctt tgctgccgac ctcacgccaa    480
acaaaagcct ttactggaaa caggctgatc agcaaatcaa gatatactag gatgagttga   540
tattatcacc ggccgcagat tactgacccg acacccttac tgcgtcatta cccctcgatc   600
```

| aag atg ccg agt cga gtt tcc gcc cgt tca aca tcc acc gcc tcg cgc | 648 |
|---|---|
| Met Pro Ser Arg Val Ser Ala Arg Ser Thr Ser Thr Ala Ser Arg | |
| 1           5           10           15 | |

| aaa ggc tct aca cag act gcg aca agc ggt cgc gct ggc tca gcg acc | 696 |
|---|---|
| Lys Gly Ser Thr Gln Thr Ala Thr Ser Gly Arg Ala Gly Ser Ala Thr | |
|           20           25           30 | |

| cca tca ttc gcc atc cca gag gaa act gca tta ccc gag gct gtt cca | 744 |
|---|---|
| Pro Ser Phe Ala Ile Pro Glu Glu Thr Ala Leu Pro Glu Ala Val Pro | |
|           35           40           45 | |

| acc ctt cgc cgc gat gta tgc gcc att ttc gcg gat gcc cag cgt tcg | 792 |
|---|---|
| Thr Leu Arg Arg Asp Val Cys Ala Ile Phe Ala Asp Ala Gln Arg Ser | |
|      50           55           60 | |

| act gcc ggt cat cgc aaa ctt gtc gtc cga cta agg aaa atc cag gag | 840 |
|---|---|
| Thr Ala Gly His Arg Lys Leu Val Val Arg Leu Arg Lys Ile Gln Glu | |
| 65           70           75 | |

| gtg tgc tgt gct ata ccc cag aag aac tcc aaa aaa gac agt tca act | 888 |
|---|---|
| Val Cys Cys Ala Ile Pro Gln Lys Asn Ser Lys Lys Asp Ser Ser Thr | |
| 80           85           90           95 | |

| gaa gag cga ttg att ccc ggc gaa gag acg gta cca gaa aag gag ttc | 936 |
|---|---|
| Glu Glu Arg Leu Ile Pro Gly Glu Glu Thr Val Pro Glu Lys Glu Phe | |
|           100           105           110 | |

| aac gtc gaa gta agt cgt tgt gtg ttg cgc atc ttg tct att aag aag | 984 |
|---|---|
| Asn Val Glu Val Ser Arg Cys Val Leu Arg Ile Leu Ser Ile Lys Lys | |
|           115           120           125 | |

| aca gag cct gtt ggc gat cga atc ctg cgg ttt ctc ggg aac ttc ctt | 1032 |
|---|---|
| Thr Glu Pro Val Gly Asp Arg Ile Leu Arg Phe Leu Gly Asn Phe Leu | |
|           130           135           140 | |

| act cat gcc tcg gaa aag gac gct gag atc ttc ggc tct gaa gaa gat | 1080 |
|---|---|
| Thr His Ala Ser Glu Lys Asp Ala Glu Ile Phe Gly Ser Glu Glu Asp | |
| 145           150           155 | |

| gaa gac gat atg cag aat tcg cac gaa aga ccg act gcc cac ttg acc | 1128 |
|---|---|
| Glu Asp Asp Met Gln Asn Ser His Glu Arg Pro Thr Ala His Leu Thr | |
| 160           165           170           175 | |

| acc agt ctt gtc tcc ctg tta gtg cct ttg ttg tct gca aaa gac aag | 1176 |
|---|---|
| Thr Ser Leu Val Ser Leu Leu Val Pro Leu Leu Ser Ala Lys Asp Lys | |
|           180           185           190 | |

| gtt gtg cgc ttc cgt acc acg caa att atc gcg cac atc gtc aat tca | 1224 |
|---|---|
| Val Val Arg Phe Arg Thr Thr Gln Ile Ile Ala His Ile Val Asn Ser | |
|           195           200           205 | |

| ctc gat acc gta gac gac gaa tta tac cac act ctc cgg caa ggc ctt | 1272 |
|---|---|
| Leu Asp Thr Val Asp Asp Glu Leu Tyr His Thr Leu Arg Gln Gly Leu | |
|           210           215           220 | |

| cta aaa cgg att cgc gac aaa gaa cct tcg gtg cgg gta caa gca gtg | 1320 |
|---|---|
| Leu Lys Arg Ile Arg Asp Lys Glu Pro Ser Val Arg Val Gln Ala Val | |
| 225           230           235 | |

| atg ggt ctc ggc cgc ttg gcc gga aat gaa gag gac gat gac gaa aat | 1368 |
|---|---|
| Met Gly Leu Gly Arg Leu Ala Gly Asn Glu Glu Asp Asp Asp Glu Asn | |
| 240           245           250           255 | |

| gat gat acc agt gcc ctt gtg gag aag ctc gtg gac ata atg caa aat | 1416 |
|---|---|
| Asp Asp Thr Ser Ala Leu Val Glu Lys Leu Val Asp Ile Met Gln Asn | |
|           260           265           270 | |

| gac acg gct gca gag gtt cgg agg aca tta ctc ctc aac ctc cca ttg | 1464 |

```
Asp Thr Ala Ala Glu Val Arg Arg Thr Leu Leu Leu Asn Leu Pro Leu
            275                 280                 285 att ccg tct acc ctt cca tac ctc ctc gaa cgc gcc cgt gac ctc gat    1512
Ile Pro Ser Thr Leu Pro Tyr Leu Leu Glu Arg Ala Arg Asp Leu Asp
        290                 295                 300 gct ccc aca cga agg gca tta tat tct cgt cta ctt ccg aca ctg gga    1560
Ala Pro Thr Arg Arg Ala Leu Tyr Ser Arg Leu Leu Pro Thr Leu Gly
305                 310                 315 gat ttc cga cat tta tct ctc tcc atg aga gaa aag ttg ctc aga tgg    1608
Asp Phe Arg His Leu Ser Leu Ser Met Arg Glu Lys Leu Leu Arg Trp
320                 325                 330                 335 ggt ctt cgt gat cgc gac aaa agt gtg agg aag gcc act gga aag ttg    1656
Gly Leu Arg Asp Arg Asp Lys Ser Val Arg Lys Ala Thr Gly Lys Leu
                340                 345                 350 ttc tat gac cgc tgg att gag ata tcg ctg gca cga aca atg acc ctg    1704
Phe Tyr Asp Arg Trp Ile Glu Ile Ser Leu Ala Arg Thr Met Thr Leu
            355                 360                 365 aga att cgg gca gcg ctc gga acg aga att ccc gct tta ctg gag ttg    1752
Arg Ile Arg Ala Ala Leu Gly Thr Arg Ile Pro Ala Leu Leu Glu Leu
        370                 375                 380 ttg gag cgt atc gat gtg gtg aac tca ggc atg gaa tcc ggc ata gcg    1800
Leu Glu Arg Ile Asp Val Val Asn Ser Gly Met Glu Ser Gly Ile Ala
385                 390                 395 cac gaa gct atg cgc agt ttc tgg gaa ggt cga cca gac tat cga gag    1848
His Glu Ala Met Arg Ser Phe Trp Glu Gly Arg Pro Asp Tyr Arg Glu
400                 405                 410                 415 gcg gta cta ttc gac gaa gcc ttc tgg gag tca atg aca gca gaa tcc    1896
Ala Val Leu Phe Asp Glu Ala Phe Trp Glu Ser Met Thr Ala Glu Ser
                420                 425                 430 gct ttc ctc ctt cgc tca ttc aat gac ttt tgc cgg gtt gaa aac gaa    1944
Ala Phe Leu Leu Arg Ser Phe Asn Asp Phe Cys Arg Val Glu Asn Glu
            435                 440                 445 ggt aaa tat gac agc ctc gcc gat gag aag atc cca gtc gtt aca gcc    1992
Gly Lys Tyr Asp Ser Leu Ala Asp Glu Lys Ile Pro Val Val Thr Ala
        450                 455                 460 ctc gca atg tat ctt cat aag tac atg acc gag ctt ctg cag cgc aag    2040
Leu Ala Met Tyr Leu His Lys Tyr Met Thr Glu Leu Leu Gln Arg Lys
465                 470                 475 aag ctc aca aag gat gct act gac gta aac gac gac gat acc gtc gaa    2088
Lys Leu Thr Lys Asp Ala Thr Asp Val Asn Asp Asp Asp Thr Val Glu
480                 485                 490                 495 atc gaa ttt atc gtc gag caa ctg ctt cac atc gcg atg aca cta gac    2136
Ile Glu Phe Ile Val Glu Gln Leu Leu His Ile Ala Met Thr Leu Asp
                500                 505                 510 tac agc gac gaa gtt ggg cgg cga aag atg ttt tct cta ctc cgt gag    2184
Tyr Ser Asp Glu Val Gly Arg Arg Lys Met Phe Ser Leu Leu Arg Glu
            515                 520                 525 gct ctc gct gtc cca gag ctc cct cag gaa tcg acc aag ctc gcg gtt    2232
Ala Leu Ala Val Pro Glu Leu Pro Gln Glu Ser Thr Lys Leu Ala Val
        530                 535                 540 gag aca ctg aga tgt gtt tgt ggg ccc gac gcc gcg gca gag agc gaa    2280
Glu Thr Leu Arg Cys Val Cys Gly Pro Asp Ala Ala Ala Glu Ser Glu
545                 550                 555 ttc tgc agt gtt gtt ctg gaa gcc att gct gaa gtt cat gac aca atc    2328
Phe Cys Ser Val Val Leu Glu Ala Ile Ala Glu Val His Asp Thr Ile
560                 565                 570                 575 agc acc gag gat agt ttc gtt tct gca aag tct gag att agc gat gat    2376
Ser Thr Glu Asp Ser Phe Val Ser Ala Lys Ser Glu Ile Ser Asp Asp
                580                 585                 590
```

```
                                                        -continued gcc agc agc cgc caa cga tcc gaa acg ccg atg agt gaa gat gac aag    2424
Ala Ser Ser Arg Gln Arg Ser Glu Thr Pro Met Ser Glu Asp Asp Lys
            595                 600                 605 cca ttc aac aag gag gag gca aag gct aag gtc ctc aag gaa atc gtt    2472
Pro Phe Asn Lys Glu Glu Ala Lys Ala Lys Val Leu Lys Glu Ile Val
        610                 615                 620 att aat atg aag tgt ctg cac att gcc ctt tgc atg ctc cag aat gtt    2520
Ile Asn Met Lys Cys Leu His Ile Ala Leu Cys Met Leu Gln Asn Val
    625                 630                 635 gaa ggc aac ctg caa gca aat atg aat ctg gtg acc atg ttg aat aac    2568
Glu Gly Asn Leu Gln Ala Asn Met Asn Leu Val Thr Met Leu Asn Asn
640                 645                 650                 655 ttg gta gta cct gct gtt cgg agc cac gaa gcg cca att cga gag cgc    2616
Leu Val Val Pro Ala Val Arg Ser His Glu Ala Pro Ile Arg Glu Arg
                660                 665                 670 ggt ctc gaa tgt ctt ggg ctg tgc tgc ttg ctg gac aag gtaagttcca     2665
Gly Leu Glu Cys Leu Gly Leu Cys Cys Leu Leu Asp Lys
            675                 680 tccttactaa atacatcttc ttctctaacc tctctgttag act ctc gca gaa gaa    2720
                                             Thr Leu Ala Glu Glu
                                                             685 aat atg acg ctg ttt att cac tgt tac agc aag ggc cac gaa aac cta    2768
Asn Met Thr Leu Phe Ile His Cys Tyr Ser Lys Gly His Glu Asn Leu
690                 695                 700                 705 cag gtc act gct att cat atc ctt tgc gat atg tta att agc cat cct    2816
Gln Val Thr Ala Ile His Ile Leu Cys Asp Met Leu Ile Ser His Pro
                710                 715                 720 tcg ctg gtg gct ccc gtt acc cag gcc gat aag gag aca gtt gcg cca    2864
Ser Leu Val Ala Pro Val Thr Gln Ala Asp Lys Glu Thr Val Ala Pro
            725                 730                 735 ccg gcg ttc cag aag cca ctg ctt aag gtc ttt tcc aga gct ctc aaa    2912
Pro Ala Phe Gln Lys Pro Leu Leu Lys Val Phe Ser Arg Ala Leu Lys
        740                 745                 750 cca aat tca ccc gcg tct gta caa acg gca gct gcg aca gct ctt tct    2960
Pro Asn Ser Pro Ala Ser Val Gln Thr Ala Ala Ala Thr Ala Leu Ser
    755                 760                 765 aag ctt ctg ctc act ggt gtt ttt act cca tct gcc gcc aat atc ccc    3008
Lys Leu Leu Leu Thr Gly Val Phe Thr Pro Ser Ala Ala Asn Ile Pro
770                 775                 780                 785 gat gcc att caa gag ttc aac caa cat gcc atc gaa aca ctg cta cag    3056
Asp Ala Ile Gln Glu Phe Asn Gln His Ala Ile Glu Thr Leu Leu Gln
                790                 795                 800 tcc ctc gtt gtc tcc ttc ttc cat ccc cga act cgc gag aat ccc gca    3104
Ser Leu Val Val Ser Phe Phe His Pro Arg Thr Arg Glu Asn Pro Ala
            805                 810                 815 ctc cga cag gca ctc gcg tac ttc ttc cct gtc tac tgc cac tcc cgg    3152
Leu Arg Gln Ala Leu Ala Tyr Phe Phe Pro Val Tyr Cys His Ser Arg
        820                 825                 830 ccg gat aac acc cag cat atg aga aag att act gta cct gtc atc cgg    3200
Pro Asp Asn Thr Gln His Met Arg Lys Ile Thr Val Pro Val Ile Arg
    835                 840                 845 acc atc cta aac tca gcg gaa gaa tac tac tca ctt gag gct gaa gag    3248
Thr Ile Leu Asn Ser Ala Glu Glu Tyr Tyr Ser Leu Glu Ala Glu Glu
850                 855                 860                 865 gac agt gat ggt gat att gat gag tct gtt ggg gag aag gaa ttg aag    3296
Asp Ser Asp Gly Asp Ile Asp Glu Ser Val Gly Glu Lys Glu Leu Lys
                870                 875                 880 gcc ctg atg agc gga gtt ctt ggt atg ctt gcg gag tgg acg gat gag    3344
Ala Leu Met Ser Gly Val Leu Gly Met Leu Ala Glu Trp Thr Asp Glu
            885                 890                 895
```

```
cga aga gtg atc gga ctt ggc ggc gaa cgg gtc ctt gct ggg ggc ctt      3392
Arg Arg Val Ile Gly Leu Gly Gly Glu Arg Val Leu Ala Gly Gly Leu
        900                 905                 910 gct agc tcc aat gtt tgt ggc att atc cac ttg caa ctg att aag gac      3440
Ala Ser Ser Asn Val Cys Gly Ile Ile His Leu Gln Leu Ile Lys Asp
    915                 920                 925 ata ctg gaa cga gtg ctc ggg atc agt gaa ggc agc aat cgc tgc tct      3488
Ile Leu Glu Arg Val Leu Gly Ile Ser Glu Gly Ser Asn Arg Cys Ser
930                 935                 940                 945 aaa caa caa cga aaa ctc ctg ttt tca ctc atg agc aag ctc tat att      3536
Lys Gln Gln Arg Lys Leu Leu Phe Ser Leu Met Ser Lys Leu Tyr Ile
            950                 955                 960 gcg ccg cca acg gca ctt tcg cgc tca gcg tcc cag gcc ccc gaa gac      3584
Ala Pro Pro Thr Ala Leu Ser Arg Ser Ala Ser Gln Ala Pro Glu Asp
                965                 970                 975 gac tcg ttc cgt tcc agc gtg cga agc tcc cat ggc gaa ctc aat ccc      3632
Asp Ser Phe Arg Ser Ser Val Arg Ser Ser His Gly Glu Leu Asn Pro
            980                 985                 990 gaa aac ctt gcc ctc gcg cag gaa gtc aag gag cta ctt gac cag acc      3680
Glu Asn Leu Ala Leu Ala Gln Glu Val Lys Glu Leu Leu Asp Gln Thr
        995                 1000                1005 atc gaa gaa ggt gtg gcg gct gat gct gct agc cga aat gcc ctc gtc      3728
Ile Glu Glu Gly Val Ala Ala Asp Ala Ala Ser Arg Asn Ala Leu Val
1010                1015                1020                1025 aag gtg aag aac gtg gtg ctc aag cta ctg gcg gct ccc atg cga cct      3776
Lys Val Lys Asn Val Val Leu Lys Leu Leu Ala Ala Pro Met Arg Pro
                1030                1035                1040 tct agc gca cgc ggc cgc gag agc agt gtc gaa agt gac att ggc agt      3824
Ser Ser Ala Arg Gly Arg Glu Ser Ser Val Glu Ser Asp Ile Gly Ser
            1045                1050                1055 gtt cga tct tcc aga agt gtt cgg ccg tcc gta gag cct ggc ttt ggg      3872
Val Arg Ser Ser Arg Ser Val Arg Pro Ser Val Glu Pro Gly Phe Gly
        1060                1065                1070 cgc cgc ggt gta tcc gtg gag ccc agt atc atg gag gag gat gag aat      3920
Arg Arg Gly Val Ser Val Glu Pro Ser Ile Met Glu Glu Asp Glu Asn
1075                1080                1085 gag gat agc cgg gcg act ctg gac agt aga atg act gtt atc aaa gag      3968
Glu Asp Ser Arg Ala Thr Leu Asp Ser Arg Met Thr Val Ile Lys Glu
1090                1095                1100                1105 gag gat gcc gac gct atg gag gaa tgattttcgg tctcaagatc tttgctgtct    4022
Glu Asp Ala Asp Ala Met Glu Glu
                1110 ggttcggcgt tgggaggtt tcccggcagg gctaatggtc atatttatgg ttaggttgcg    4082 atgtaattat tcgattcttg gttatgcttg aacatgctct atatgttaca aataattcac    4142 tccaaacgtt catgtatgag tatggatctg ttttatattg gccttaccag gatagctcag    4202 ttcttggcga agtatccca gactgacagc tgcctccagg ccagaattgg ctagtcttag    4262 tcttaggtag catctgagtt atcgcgtggt atcaacagtg atcagtgtgg aagggccatc    4322 cgatctgttt gatcttacca gaacgtgtta caacaattca acccaccata tatatggtat    4382 ctacgtcaat gtgaatgaat ctgcttgggc agccttatga ctctggtgac gcgactcggg    4442 gcttgattca atgcgggcaa gaccgcatgt ggagactcct agcatcggat gtgaggcttc    4502 cgttttaatt tcttcctcca aatcgtctgc ctgcctcgct gctttgaaat actccggagg    4562 taccaaagta aagataaatg gttgactctg agagactgct tgacctcct ggaccaagtc    4622 gtgcctagcc agaaggggag tgttcaatgg gctttgtgag gctactaagg ccgcacgata    4682
```

-continued

```
caccggagat gcaaagaagt ccgatacggt cgtccatatc tcgagcacct ttattactgg      4742
cgcttttgca gttatatgga ggcgtttaat gattgcgtgt tcggaatccg atgaataata      4802
tctcattagt cgactaaacg gggatgagga tggatgactg ctggtatctt ggtctcaaac      4862
tgtaataagc gtctcggcaa caccgtacgg ttgacaatcc tgggcagatg cagcacctg       4922 tagaatccaa gaagacgcag ctggactcat tgagacagtt gaattcctta actataatga     4982
cagactaata atacaaaagt gcggtggtca acttcttccc aatcccctca aaagtcagac      5042
ccgaccctgt tctttctaat aatctgacgc tccaccaaaa gtccagcttc tgggcgactt      5102
tcttttcttt ccccatcctt ttcctttccc actctcctcc ctcctctctc gcttctcttc      5162
ctttcgctgt atgtttttg ttgcttgatt cacgactttc tttttccttc tggtcgtgga       5222
tccgtgtctt ctgcccccac ttgcagaggc acgattttc tccctctccc tctcctccct      5282
tccgtactcc cccctcccc cctgctctgc gcctttggca tccggagcct gcgtcgagac      5342
cgtgagcgat ggcctccgtg tcagctccca cgcccaagct ggaccgctac atcgtcgttc      5402
atgtggcaac tacctgcgat gagcatggcg tctacgtcac caaggactct gcagagtgat     5462
cgagttgggg tggatcttgt tggataccaa aacctgcgag agtcgcagtg attctctccc     5522
tgcaccacac ctattccacc ccctctttg tgtcttgatt ctcgccggcc taccgggatt      5582
ctgccgacga catt                                                        5596
```

<210> SEQ ID NO 2
<211> LENGTH: 684
<212> TYPE: PRT
<213> ORGANISM: Aspergillus nidulans

<400> SEQUENCE: 2

```
Met Pro Ser Arg Val Ser Ala Arg Ser Thr Ser Thr Ala Ser Arg Lys
  1               5                  10                  15

Gly Ser Thr Gln Thr Ala Thr Ser Gly Arg Ala Gly Ser Ala Thr Pro
             20                  25                  30

Ser Phe Ala Ile Pro Glu Glu Thr Ala Leu Pro Glu Ala Val Pro Thr
         35                  40                  45

Leu Arg Arg Asp Val Cys Ala Ile Phe Ala Asp Ala Gln Arg Ser Thr
     50                  55                  60

Ala Gly His Arg Lys Leu Val Val Arg Leu Arg Lys Ile Gln Glu Val
 65                  70                  75                  80

Cys Cys Ala Ile Pro Gln Lys Asn Ser Lys Asp Ser Ser Thr Glu
                 85                  90                  95

Glu Arg Leu Ile Pro Gly Glu Glu Thr Val Pro Glu Lys Glu Phe Asn
            100                 105                 110

Val Glu Val Ser Arg Cys Val Leu Arg Ile Leu Ser Ile Lys Lys Thr
        115                 120                 125

Glu Pro Val Gly Asp Arg Ile Leu Arg Phe Leu Gly Asn Phe Leu Thr
    130                 135                 140

His Ala Ser Glu Lys Asp Ala Glu Ile Phe Gly Ser Glu Glu Asp Glu
145                 150                 155                 160

Asp Asp Met Gln Asn Ser His Glu Arg Pro Thr Ala His Leu Thr Thr
                165                 170                 175

Ser Leu Val Ser Leu Leu Val Pro Leu Leu Ser Ala Lys Asp Lys Val
            180                 185                 190

Val Arg Phe Arg Thr Thr Gln Ile Ile Ala His Ile Val Asn Ser Leu
        195                 200                 205
```

```
Asp Thr Val Asp Asp Glu Leu Tyr His Thr Leu Arg Gln Gly Leu Leu
    210                 215                 220
Lys Arg Ile Arg Asp Lys Glu Pro Ser Val Arg Val Gln Ala Val Met
225                 230                 235                 240
Gly Leu Gly Arg Leu Ala Gly Asn Glu Glu Asp Asp Glu Asn Asp
                245                 250                 255
Asp Thr Ser Ala Leu Val Glu Lys Leu Val Asp Ile Met Gln Asn Asp
            260                 265                 270
Thr Ala Ala Glu Val Arg Arg Thr Leu Leu Asn Leu Pro Leu Ile
        275                 280                 285
Pro Ser Thr Leu Pro Tyr Leu Leu Glu Arg Ala Arg Asp Leu Asp Ala
    290                 295                 300
Pro Thr Arg Arg Ala Leu Tyr Ser Arg Leu Leu Pro Thr Leu Gly Asp
305                 310                 315                 320
Phe Arg His Leu Ser Leu Ser Met Arg Glu Lys Leu Leu Arg Trp Gly
                325                 330                 335
Leu Arg Asp Arg Asp Lys Ser Val Arg Lys Ala Thr Gly Lys Leu Phe
            340                 345                 350
Tyr Asp Arg Trp Ile Glu Ile Ser Leu Ala Arg Thr Met Thr Leu Arg
        355                 360                 365
Ile Arg Ala Ala Leu Gly Thr Arg Ile Pro Ala Leu Leu Glu Leu Leu
    370                 375                 380
Glu Arg Ile Asp Val Val Asn Ser Gly Met Glu Ser Gly Ile Ala His
385                 390                 395                 400
Glu Ala Met Arg Ser Phe Trp Glu Gly Arg Pro Asp Tyr Arg Glu Ala
                405                 410                 415
Val Leu Phe Asp Glu Ala Phe Trp Glu Ser Met Thr Ala Glu Ser Ala
            420                 425                 430
Phe Leu Leu Arg Ser Phe Asn Asp Phe Cys Arg Val Glu Asn Glu Gly
        435                 440                 445
Lys Tyr Asp Ser Leu Ala Asp Glu Lys Ile Pro Val Thr Ala Leu
    450                 455                 460
Ala Met Tyr Leu His Lys Tyr Met Thr Glu Leu Leu Gln Arg Lys Lys
465                 470                 475                 480
Leu Thr Lys Asp Ala Thr Asp Val Asn Asp Asp Thr Val Glu Ile
                485                 490                 495
Glu Phe Ile Val Glu Gln Leu Leu His Ile Ala Met Thr Leu Asp Tyr
            500                 505                 510
Ser Asp Glu Val Gly Arg Arg Lys Met Phe Ser Leu Leu Arg Glu Ala
        515                 520                 525
Leu Ala Val Pro Glu Leu Pro Gln Glu Ser Thr Lys Leu Ala Val Glu
    530                 535                 540
Thr Leu Arg Cys Val Cys Gly Pro Asp Ala Ala Ala Glu Ser Glu Phe
545                 550                 555                 560
Cys Ser Val Val Leu Glu Ala Ile Ala Glu Val His Asp Thr Ile Ser
                565                 570                 575
Thr Glu Asp Ser Phe Val Ser Ala Lys Ser Glu Ile Ser Asp Asp Ala
            580                 585                 590
Ser Ser Arg Gln Arg Ser Glu Thr Pro Met Ser Glu Asp Asp Lys Pro
        595                 600                 605
Phe Asn Lys Glu Glu Ala Lys Ala Lys Val Leu Lys Glu Ile Val Ile
    610                 615                 620
Asn Met Lys Cys Leu His Ile Ala Leu Cys Met Leu Gln Asn Val Glu
```

|  | 625 |  |  |  | 630 |  |  |  | 635 |  |  |  | 640 |
| :-: | :-: | :-: | :-: | :-: | :-: | :-: | :-: | :-: | :-: | :-: | :-: | :-: | :-: |
| Gly | Asn | Leu | Gln | Ala | Asn | Met | Asn | Leu | Val | Thr | Met | Leu | Asn | Asn | Leu |
|  |  |  |  |  | 645 |  |  |  | 650 |  |  |  | 655 |

Val Val Pro Ala Val Arg Ser His Glu Ala Pro Ile Arg Glu Arg Gly
            660                 665                 670

Leu Glu Cys Leu Gly Leu Cys Cys Leu Leu Asp Lys
        675                 680

<210> SEQ ID NO 3
<211> LENGTH: 5596
<212> TYPE: DNA
<213> ORGANISM: Aspergillus nidulans

<400> SEQUENCE: 3

```
tcgcgacgcg tcccgtcgac accgtttagc ggcctgcgaa accgctttgt aggacagtta    60
tagttacgac gaggactttg tcttttctg ttctgcttca aggggcctaa catagagctt    120
actcccctgg ctaaaggccg caatcattct ccagtgcact ttctaccgca cgattgatca   180
tacgttccgt aaagccgagt ccgttttatg ggtcagttgt taaacaacgg acctccacct   240
ttatgctctg ggaactaacg ctcgtcacac actaatccta tcgactccgt aacataagta   300
catagtcctt ggactagcag tttcgcaacg tccgacgacc cgacccgtgc acgacgggat   360
tgggaataga tagatgacca aaccccacaa acaaatacga ggcgggcac tgagagtcgt    420
tgccaatatt gctcatcacc gtcgtcggtt gcttgaagaa acgacggctg gagtgcggtt   480
tgttttcgga aatgaccttt gtccgactag tcgtttagtt ctatatgatc ctactcaact   540
ataatagtgg ccggcgtcta atgactgggc tgtgggaatg acgcagtaat ggggagctag   600
ttctacggct cagctcaaag gcgggcaagt tgtaggtggc ggagcgcgtt tccgagatgt   660
gtctgacgct gttcgccagc gcgaccgagt cgctggggta gtaagcggta gggtctcctt   720
tgacgtaatg ggctccgaca aggttgggaa gcggcgctac atacgcggta aaagcgccta   780
cgggtcgcaa gctgacggcc agtagcgttt gaacagcagg ctgattcctt ttaggtcctc   840
cacacgacac gatatggggt cttcttgagg tttttctgt caagttgact tctcgctaac    900
taagggccgc ttctctgcca tggtcttttc ctcaagttgc agcttcattc agcaacacac   960
aacgcgtaga acagataatt cttctgtctc ggacaaccgc tagcttagga cgccaaagag  1020
cccttgaagg aatgagtacg gagccttttc ctgcgactct agaagccgag acttcttcta  1080
cttctgctat acgtcttaag cgtgctttct ggctgacggg tgaactggtg gtcagaacag  1140
agggacaatc acgaaacaa cagacgtttt ctgttccaac acgcgaaggc atggtgcgtt   1200
taatagcgcg tgtagcagtt aagtgagcta tggcatctgc tgcttaatat ggtgtgagag  1260
gccgttccgg aagatttgc ctaagcgctg tttcttggaa ccacgccca tgttcgtcac    1320
tacccagagc cggcgaaccg gcctttactt ctcctgctac tgcttttact actatggtca  1380
cgggaacacc tcttcgagca cctgtattac gttttactgt gccgacgtct ccaagcctcc  1440
tgtaatgagg agttggaggg taactaaggc agatgggaag gtatgaggga gcttgcgcgg  1500
gcactggagc tacgagggtg tgcttcccgt aatataagag cagatgaagg ctgtgaccct  1560
ctaaaggctg taaatagaga gaggtactct cttttcaacg agtctacccc agaagcacta  1620
gcgctgtttt cacactcctt ccggtgacct ttcaacaaga tactggcgac ctaactctat  1680
agcgaccgtg cttgttactg ggactcttaa gcccgtcgcg agccttgctc ttaagggcga  1740
aatgaccctca acaacctcgc atagctacac cacttgagtc cgtaccttag gccgtatcgc  1800
```

-continued

```
gtgcttcgat acgcgtcaaa gaccettcca gctggtctga tagctctccg ccatgataag    1860
ctgcttcgga agaccctcag ttactgtcgt cttaggcgaa aggaggaagc gagtaagtta    1920
ctgaaaacgg cccaactttt gcttccattt atactgtcgg agcggctact cttctagggt    1980
cagcaatgtc gggagcgtta catagaagta ttcatgtact ggctcgaaga cgtcgcgttc    2040
ttcgagtgtt tcctacgatg actgcatttg ctgctgctat gcagctttta gcttaaatag    2100
cagctcgttg acgaagtgta gcgctactgt gatctgatgt cgctgcttca acccgccgct    2160
ttctacaaaa gagatgaggc actccgagag cgacagggtc tcgagggagt ccttagctgg    2220
ttcgagcgcc aactctgtga ctctacacaa acacccgggc tgcggcgccg tctctcgctt    2280
aagacgtcac aacaagacct tcggtaacga cttcaagtac tgtgttagtc gtggctccta    2340
tcaaagcaaa gacgtttcag actctaatcg ctactacggt cgtcggcggt tgctaggctt    2400
tgcggctact cacttctact gttcggtaag ttgttcctcc tccgtttccg attccaggag    2460
ttcctttagc aataattata cttcacagac gtgtaacggg aaacgtacga ggtcttacaa    2520
cttccgttgg acgttcgttt atacttagac cactggtaca acttattgaa ccatcatgga    2580
cgacaagcct cggtgcttcg cggttaagct ctcgcgccag agcttacaga acccgacacg    2640
acgaacgacc tgttccattc aaggtaggaa tgatttatgt agaagaagag attggagaga    2700
caatctgaga gcgtcttctt ttatactgcg acaaataagt gacaatgtcg ttcccggtgc    2760
ttttggatgt ccagtgacga taagtatagg aaacgctata caattaatcg gtaggaagcg    2820
accaccgagg gcaatgggtc cggctattcc tctgtcaacg cggtggccgc aaggtttcg     2880 gtgacgaatt ccagaaaagg tctcgagagt ttggtttaag tgggcgcaga catgtttgcc    2940
gtcgacgctg tcgagaaaga ttcgaagacg agtgaccaca aaaatgaggt agacggcggt    3000 tatagggct acggtaagtt ctcaagttgg ttgtacggta gctttgtgac gatgtcaggg     3060
agcaacagag gaagaaggta ggggcttgag cgctcttagg gcgtgaggct gtccgtgagc    3120
gcatgaagaa gggacagatg acggtgaggg ccggcctatt gtgggtcgta tactctttct    3180
aatgacatgg acagtaggcc tggtaggatt tgagtcgcct tcttatgatg agtgaactcc    3240
gacttctcct gtcactacca ctataactac tcagacaacc cctcttcctt aacttccggg    3300
actactcgcc tcaagaacca tacgaacgcc tcacctgcct actcgcttct cactagcctg    3360
aaccgccgct tgcccaggaa cgaccccgg  aacgatcgag gttacaaaca ccgtaatagg    3420
tgaacgttga ctaattcctg tatgaccttg ctcacgagcc ctagtcactt ccgtcgttag    3480
cgacgagatt tgttgttgct tttgaggaca aaagtgagta ctcgttcgag atataacgcg    3540
gcggttgccg tgaaagcgcg agtcgcaggg tccggggct  tctgctgagc aaggcaaggt    3600
cgcacgcttc gagggtaccg cttgagttag ggcttttgga acgggagcgc gtccttcagt    3660
tcctcgatga actggtctgg tagcttcttc cacaccgccg actacgacga tcggcttac     3720 gggagcagtt ccacttcttg caccacgagt tcgatgaccg ccgagggtac gctggaagat    3780
cgcgtgcgcc ggcgctctcg tcacagcttt cactgtaacc gtcacaagct agaaggtctt    3840
cacaagccgg caggcatctc ggaccgaaac ccgcggcgcc acataggcac ctcgggtcat    3900
agtacctcct cctactctta ctcctatcgg cccgctgaga cctgtcatct tactgacaat    3960
agtttctcct cctacggctg cgatacctcc ttactaaaag ccagagttct agaaacgaca    4020
gaccaagccg caaccctcc  aaagggccgt cccgattacc agtataaata ccaatccaac    4080
gctacattaa taagctaaga accaatacga acttgtacga gatatacaat gtttattaag    4140
tgaggtttgc aagtacatac tcatacctag acaaaatata accggaatgg tcctatcgag    4200
```

```
tcaagaaccg cttcaatagg gtctgactgt cgacggaggt ccggtcttaa ccgatcagaa      4260
tcagaatcca tcgtagactc aatagcgcac catagttgtc actagtcaca ccttcccggt      4320
aggctagaca aactagaatg gtcttgcaca atgttgttaa gttgggtggt atatatacca      4380
tagatgcagt tacacttact tagacgaacc cgtcggaata ctgagaccac tgcgctgagc      4440
cccgaactaa gttacgcccg ttctggcgta cacctctgag gatcgtagcc tacactccga      4500
aggcaaaatt aaagaaggag gtttagcaga cggacggagc gacgaaactt tatgaggcct      4560
ccatggtttc atttctattt accaactgag actctctgac gaaactggag gacctggttc      4620
agcacggatc ggtcttcccc tcacaagtta cccgaaacac tccgatgatt ccggcgtgct      4680
atgtggcctc tacgtttctt caggctatgc cagcaggtat agagctcgtg gaaataatga      4740
ccgcgaaaac gtcaatatac ctccgcaaat tactaacgca caagccttag gctacttatt      4800
atagagtaat cagctgattt gccccctactc ctacctactg acgaccatag aaccagagtt      4860
tgacattatt cgcagagccg ttgtggcatg ccaactgtta ggacccgtct accgtcgtgg      4920
acatcttagg ttcttctgcg tcgacctgag taactctgtc aacttaagga attgatatta      4980
ctgtctgatt attatgtttt cacgccacca gttgaagaag ggttagggga gttttcagtc      5040
tgggctggga caagaaagat tattagactg cgaggtggtt ttcaggtcga agacccgctg      5100
aaagaaaaag aagggtagg aaaaggaaag ggtgagagga gggaggagag agcgaagaga      5160
aggaaagcga catacaaaaa acaacgaact aagtgctgaa agaaaaagga agaccagcac      5220
ctaggcacag aagacggggg tgaacgtctc cgtgctaaaa agagggagag ggagaggagg      5280
gaaggcatga ggggggggagg ggggacgaga gcggaaacc gtaggcctcg gacgcagctc      5340
tggcactcgc taccggaggc acagtcgagg gtgcgggttc gacctggcga tgtagcagca      5400
agtacaccgt tgatggacgc tactcgtacc gcagatgcag tggttcctga gacgtctcac      5460
tagctcaacc ccacctagaa caacctatgg ttttggacgc tctcagcgtc actaagagag      5520
ggacgtggtg tggataaggt gggggagaaa acacagaact aagagcggcc ggatggccct      5580
aagacggctg ctgtaa                                                     5596
```

<210> SEQ ID NO 4
<211> LENGTH: 1758
<212> TYPE: DNA
<213> ORGANISM: Aspergillus nidulans
<220> FEATURE:
<221> NAME/KEY: CDS
<222> LOCATION: (162)...(1319)

<400> SEQUENCE: 4

```
caaaagtctt gatcacaggg gcacaagcgc aattgagcca ccatgcttac ggacggcatc       60
gaaggggtca aggagaaagt cttttgtgctc gtgaccggtg ccaacaggta cagtgaaacc      120
ctgcgctctg tctcctatct catgcggtcc gttagtggtt t atg ttt cta act gtt      176
                                              Met Phe Leu Thr Val
                                                1               5 acc cct tgt ggg ttt tca ccg ttt agc gga cta gga tac tca acg tgt        224
Thr Pro Cys Gly Phe Ser Pro Phe Ser Gly Leu Gly Tyr Ser Thr Cys
           10                  15                  20 tgc cgt ctt gca gat gaa ttc ctg gcg tct cat cgg aac gac cat cgt        272
Cys Arg Leu Ala Asp Glu Phe Leu Ala Ser His Arg Asn Asp His Arg
       25                  30                  35 tca ttg aca atc atc ttc act acc cgg agc aca aga aag gga agc gac        320
Ser Leu Thr Ile Ile Phe Thr Thr Arg Ser Thr Arg Lys Gly Ser Asp
   40                  45                  50
```

```
acc ctt cgc aac cta cag aat cac ctc cgc acc tcc acc ttc ggt gct      368
Thr Leu Arg Asn Leu Gln Asn His Leu Arg Thr Ser Thr Phe Gly Ala
    55                  60                  65 tcg gcc acc gct cga gtg acc ttc gtt cct gaa aat gtc gac ctc tgc      416
Ser Ala Thr Ala Arg Val Thr Phe Val Pro Glu Asn Val Asp Leu Cys
70                  75                  80                  85 aac ctc ctc tcg gtc cgc gcg cta tcc cgt cgc ctg aac aag acc ttc      464
Asn Leu Leu Ser Val Arg Ala Leu Ser Arg Arg Leu Asn Lys Thr Phe
                90                  95                 100 cca aaa ctc gac gcg att gtg ctt aat gcc ggg ata ggg ggt tgg tct      512
Pro Lys Leu Asp Ala Ile Val Leu Asn Ala Gly Ile Gly Gly Trp Ser
            105                 110                 115 ggc ctc aat tgg cct ctg gcc gta tgg agc gtt tgc acc gac att atc      560
Gly Leu Asn Trp Pro Leu Ala Val Trp Ser Val Cys Thr Asp Ile Ile
        120                 125                 130 cat gcg acg acg tgg cca aag tac aaa att gcg cct gta ggt ctc ata      608
His Ala Thr Thr Trp Pro Lys Tyr Lys Ile Ala Pro Val Gly Leu Ile
    135                 140                 145 acg gac aac cag aca att act gtg acc gac aag gag ccc cgc ctg gga      656
Thr Asp Asn Gln Thr Ile Thr Val Thr Asp Lys Glu Pro Arg Leu Gly
150                 155                 160                 165 acc gtc ttc tgc gcc aac gtc ttc ggc cac tac atg ctc gcg cat aat      704
Thr Val Phe Cys Ala Asn Val Phe Gly His Tyr Met Leu Ala His Asn
                170                 175                 180 gtc atg cct ctc ctg cac cga tcc gga tcc ccc aac gga ccc gga cgc      752
Val Met Pro Leu Leu His Arg Ser Gly Ser Pro Asn Gly Pro Gly Arg
            185                 190                 195 gtg ata tgg ctc tcc agc act gaa gcc acg atc aac ttc ttc gat gtt      800
Val Ile Trp Leu Ser Ser Thr Glu Ala Thr Ile Asn Phe Phe Asp Val
        200                 205                 210 gat gat ttt cag gcg ctc cgg tcc aaa gct ccc tac gag tca tca aaa      848
Asp Asp Phe Gln Ala Leu Arg Ser Lys Ala Pro Tyr Glu Ser Ser Lys
    215                 220                 225 gcg cta aca gac ctc cta tcc ctc acc tca gac ctt ccc agt act gct      896
Ala Leu Thr Asp Leu Leu Ser Leu Thr Ser Asp Leu Pro Ser Thr Ala
230                 235                 240                 245 ccc tgg gtg aaa agc ttc tat tcc acc gac ttc gaa acc gat tcc aag      944
Pro Trp Val Lys Ser Phe Tyr Ser Thr Asp Phe Glu Thr Asp Ser Lys
                250                 255                 260 ccc agc acc gga cct gag acc gcc tcg acc ata ccc aac gta tac ctc      992
Pro Ser Thr Gly Pro Glu Thr Ala Ser Thr Ile Pro Asn Val Tyr Leu
            265                 270                 275 tct cac ccc gga atc tgc gct acg gcg att ata ccc ctt cct aca atc     1040
Ser His Pro Gly Ile Cys Ala Thr Ala Ile Ile Pro Leu Pro Thr Ile
        280                 285                 290 ctc atc tac gca atg gtc gcc gca ttt tgg cta gcc cgc atc ctc ggc     1088
Leu Ile Tyr Ala Met Val Ala Ala Phe Trp Leu Ala Arg Ile Leu Gly
    295                 300                 305 tcc cct tgg cat acc tta tcc acc tac cta ggc gct tgc agc cct gtc     1136
Ser Pro Trp His Thr Leu Ser Thr Tyr Leu Gly Ala Cys Ser Pro Val
310                 315                 320                 325 tgg ctt gct ctc tcc aca caa tca gaa ctc gac gcc gcc gaa gca ccg     1184
Trp Leu Ala Leu Ser Thr Gln Ser Glu Leu Asp Ala Ala Glu Ala Pro
                330                 335                 340 tac cgg aaa cac ggc ggc ggc agg gtg aaa tgg ggg tct tcg gcg tct     1232
Tyr Arg Lys His Gly Gly Gly Arg Val Lys Trp Gly Ser Ser Ala Ser
            345                 350                 355 cga tta ggt gta gcc tcc gtc gta tct tcg gag gtt gac gga tgg ggc     1280
Arg Leu Gly Val Ala Ser Val Val Ser Ser Glu Val Asp Gly Trp Gly
```

-continued

```
                360                 365                 370
tat ggg ggt gtt cct ggg gcc ggc tgt tgt ggc gga gga tagggtctga    1329
Tyr Gly Gly Val Pro Gly Ala Gly Cys Cys Gly Gly Gly
            375                 380                 385 aggcgcaagc gtggtgcagt ggatcttacg gctgagggga aggagggatt ccaggaactg    1389
ggggctatat gttggaggca gatggaggag ctgaggatcc tgtgggataa cttacttgat    1449
gaagagagaa ggggactggt gtgacggcgt aggtggcttg tcctgggagt gagatctctt    1509
acatttcggc cttcgtccct aaaatccttt tctcccttcc tctttattat acgatgtcgg    1569
cggttttatg ttcaatacag cacatctacg gtacaaagac aacatatagc taatataata    1629
tcatagataa tagtaataat caagcacaaa agctcgattc tgcaagatct caatatcttt    1689
attccagttt tcactgctct tgtcttccat atttacattc cacgtccacg tgcatccttt    1749
aaaaacagt                                                           1758
```

<210> SEQ ID NO 5
<211> LENGTH: 386
<212> TYPE: PRT
<213> ORGANISM: Aspergillus nidulans

<400> SEQUENCE: 5

```
Met Phe Leu Thr Val Thr Pro Cys Gly Phe Ser Pro Phe Ser Gly Leu
 1               5                  10                  15

Gly Tyr Ser Thr Cys Cys Arg Leu Ala Asp Glu Phe Leu Ala Ser His
            20                  25                  30

Arg Asn Asp His Arg Ser Leu Thr Ile Ile Phe Thr Thr Arg Ser Thr
        35                  40                  45

Arg Lys Gly Ser Asp Thr Leu Arg Asn Leu Gln Asn His Leu Arg Thr
    50                  55                  60

Ser Thr Phe Gly Ala Ser Ala Thr Ala Arg Val Thr Phe Val Pro Glu
65                  70                  75                  80

Asn Val Asp Leu Cys Asn Leu Leu Ser Val Arg Ala Leu Ser Arg Arg
                85                  90                  95

Leu Asn Lys Thr Phe Pro Lys Leu Asp Ala Ile Val Leu Asn Ala Gly
            100                 105                 110

Ile Gly Gly Trp Ser Gly Leu Asn Trp Pro Leu Ala Val Trp Ser Val
        115                 120                 125

Cys Thr Asp Ile Ile His Ala Thr Thr Trp Pro Lys Tyr Lys Ile Ala
    130                 135                 140

Pro Val Gly Leu Ile Thr Asp Asn Gln Thr Ile Thr Val Thr Asp Lys
145                 150                 155                 160

Glu Pro Arg Leu Gly Thr Val Phe Cys Ala Asn Val Phe Gly His Tyr
                165                 170                 175

Met Leu Ala His Asn Val Met Pro Leu Leu His Arg Ser Gly Ser Pro
            180                 185                 190

Asn Gly Pro Gly Arg Val Ile Trp Leu Ser Ser Thr Glu Ala Thr Ile
        195                 200                 205

Asn Phe Phe Asp Val Asp Phe Gln Ala Leu Arg Ser Lys Ala Pro
    210                 215                 220

Tyr Glu Ser Ser Lys Ala Leu Thr Asp Leu Ser Leu Thr Ser Asp
225                 230                 235                 240

Leu Pro Ser Thr Ala Pro Trp Val Lys Ser Phe Tyr Ser Thr Asp Phe
                245                 250                 255

Glu Thr Asp Ser Lys Pro Ser Thr Gly Pro Glu Thr Ala Ser Thr Ile
```

```
                260             265             270
Pro Asn Val Tyr Leu Ser His Pro Gly Ile Cys Ala Thr Ala Ile Ile
            275             280             285
Pro Leu Pro Thr Ile Leu Ile Tyr Ala Met Val Ala Ala Phe Trp Leu
        290             295             300
Ala Arg Ile Leu Gly Ser Pro Trp His Thr Leu Ser Thr Tyr Leu Gly
305             310             315             320
Ala Cys Ser Pro Val Trp Leu Ala Leu Ser Thr Gln Ser Glu Leu Asp
            325             330             335
Ala Ala Glu Ala Pro Tyr Arg Lys His Gly Gly Arg Val Lys Trp
            340             345             350
Gly Ser Ser Ala Ser Arg Leu Gly Val Ala Ser Val Val Ser Ser Glu
            355             360             365
Val Asp Gly Trp Gly Tyr Gly Gly Val Pro Gly Ala Gly Cys Cys Gly
    370             375             380
Gly Gly
385
```

<210> SEQ ID NO 6
<211> LENGTH: 1758
<212> TYPE: DNA
<213> ORGANISM: Aspergillus nidulans

<400> SEQUENCE: 6

```
gttttcagaa ctagtgtccc cgtgttcgcg ttaactcggt ggtacgaatg cctgccgtag      60
cttccccagt tcctctttca gaaacacgag cactggccac ggttgtccat gtcactttgg     120
gacgcgagac agaggataga gtacgccagg caatcaccaa atacaaagat tgacaatggg     180
gaacacccaa aagtggcaaa tcgcctgatc ctatgagttg cacaacggca gaacgtctac     240
ttaaggaccg cagagtagcc ttgctggtag caagtaactg ttagtagaag tgatgggcct     300
cgtgttcttt ccttcgctg tgggaagcgt tggatgtctt agtggaggcg tggaggtgga     360
agccacgaag ccggtggcga gctcactgga agcaaggact tttacagctg agacgttgg     420
aggagagcca ggcgcgcgat agggcagcgg acttgttctg aagggtttt gagctgcgct     480
aacacgaatt acgcccctat ccccccaacca gaccggagtt aaccggagac cggcataacct    540
cgcaaacgtg gctgtaatag gtacgctgct gcaccggttt catgtttta cgcggacatc     600
cagagtattg cctgttggtc tgttaatgac actggctgtt cctcggggcg gacccttggc     660
agaagacgcg gttgcagaag ccggtgatgt acgagcgcgt attacagtac ggagaggacg     720
tggctaggcc taggggttg cctgggcctg cgcactatac cgagaggtcg tgacttcggt     780
gctagttgaa gaagctacaa ctactaaaag tccgcgaggc caggtttcga gggatgctca     840
gtagttttcg cgattgtctg gaggatatggg agtggagtct ggaagggtca tgacgaggga     900
cccactttc gaagataagg tggctgaagc tttggctaag gttcgggtcg tggcctggac     960
tctggcggag ctggtatggg ttgcatatgg agagagtggg gccttagacg cgatgccgct    1020
aatatgggga aggatgttag gagtagatgc gttaccagcg gcgtaaaacc gatcgggcgt    1080
aggagccgag gggaaccgta tggaataggg ggatggatcc cgaacgtcg ggacagaccg    1140
aacgagagag gtgtgttagt cttgagctgc ggcggcttcg tggcatggcc tttgtgccgc    1200
cgccgtccca ctttacccc agaagccgca gagctaatcc acatcggagg cagcatagaa    1260
gcctccaact gcctaccccg ataccccccac aaggaccccg gccgacaaca ccgcctccta    1320
tcccagactt ccgcgttcgc accacgtcac ctagaatgcc gactccccctt cctccctaag    1380
```

-continued

```
gtccttgacc cccgatatac aacctccgtc tacctcctcg actcctagga cacccctattg    1440 aatgaactac ttctctcttc ccctgaccac actgccgcat ccaccgaaca ggaccctcac    1500
tctagagaat gtaaagccgg aagcagggat tttaggaaaa gagggaagga gaaataatat    1560
gctacagccg ccaaaataca agttatgtcg tgtagatgcc atgtttctgt tgtatatcga    1620
ttatattata gtatctatta tcattattag ttcgtgtttt cgagctaaga cgttctagag    1680
ttatagaaat aaggtcaaaa gtgacgagaa cagaaggtat aaatgtaagg tgcaggtgca    1740
cgtaggaaat ttttgtca                                                  1758

<210> SEQ ID NO 7
<211> LENGTH: 1792
<212> TYPE: DNA
<213> ORGANISM: Aspergillus nidulans
<220> FEATURE:
<221> NAME/KEY: CDS
<222> LOCATION: (230)...(309)
<221> NAME/KEY: CDS
<222> LOCATION: (375)...(815)
<221> NAME/KEY: CDS
<222> LOCATION: (876)...(1149)
<221> NAME/KEY: CDS
<222> LOCATION: (1200)...(1475)

<400> SEQUENCE: 7
gaattcctgt gatggagcag aacctcggag tatgctccga tgtcagtaca ttaaattttg     60
tagcgatcca cgtgatttct attttgcgtc cgcaataggc cttctgatac ggctgaagaa    120
atatagtacg tggtccagtg cctatagacg gaaagtattt tcgtacggtt ggctcccaag    180
gcaataggtc aacctcgcat acggagaata acggtacggt cctgaagga atg agg gga    238
                                                        Met Arg Gly
                                                          1 tgt att ctc ctt ctc cga ggg cca gaa ggg gaa cag gcc cgc act gat      286
Cys Ile Leu Leu Leu Arg Gly Pro Glu Gly Glu Gln Ala Arg Thr Asp
      5                  10                  15 ccg gcg aaa att tcc cct ctc ga gtcttcgctc tccccccac acggctgact      339
Pro Ala Lys Ile Ser Pro Leu Asp
 20                  25 aaccccttcca ttcttgcccg catccagcca gccag c ctt ttg tcg ccg ccc ttg     393
                                        Leu Leu Ser Pro Pro Leu
                                                     30 gtt cgg gct act gtc atc ttc cct tct tca tct tca tgc cgc tct cga      441
Val Arg Ala Thr Val Ile Phe Pro Ser Ser Ser Ser Cys Arg Ser Arg
  35                  40                  45 ctg aaa tat tca gtc tct tgc tct gat tta cag tta cta cgc gca gac      489
Leu Lys Tyr Ser Val Ser Cys Ser Asp Leu Gln Leu Leu Arg Ala Asp
 50                  55                  60                  65 acg ctg cac atc tcc gcg atc atg acc gaa tcc act caa gaa cag ggc      537
Thr Leu His Ile Ser Ala Ile Met Thr Glu Ser Thr Gln Glu Gln Gly
              70                  75                  80 aac gat ggc cag cga atg ccc ccc gcc ccg gcg acc ccc gtt gag gat      585
Asn Asp Gly Gln Arg Met Pro Pro Ala Pro Ala Thr Pro Val Glu Asp
          85                  90                  95 tac gtc ttc cct gaa tat cgc ctg aag cgt gtg atg gat gac ccg gaa      633
Tyr Val Phe Pro Glu Tyr Arg Leu Lys Arg Val Met Asp Asp Pro Glu
         100                 105                 110 aag acg ccg cta ttg ctt ata gct tgc ggt tca ttc tca cct att acg      681
Lys Thr Pro Leu Leu Leu Ile Ala Cys Gly Ser Phe Ser Pro Ile Thr
     115                 120                 125 ttc ctg cac ctg cgc atg ttc gaa atg gcc gcc gat tac gtc aaa ctg      729
```

```
Phe Leu His Leu Arg Met Phe Glu Met Ala Ala Asp Tyr Val Lys Leu
130                 135                 140                 145 agc aca gat ttc gaa ata att gga ggt tat ctt tcg ccc gtc tcg gac         777
Ser Thr Asp Phe Glu Ile Ile Gly Gly Tyr Leu Ser Pro Val Ser Asp
                150                 155                 160 gcc tac cgc aag gca ggt ctt gcg agt gcc aat cac ag gtagttactt           825
Ala Tyr Arg Lys Ala Gly Leu Ala Ser Ala Asn His Arg
                165                 170 taacacactt cttccatagt tactatccag gactgatctg gcggctttag a att gca        882
                                                        Ile Ala
                                                        175 atg tgc caa cga gcc gtg gac caa acg tca gac tgg atg atg gtg gat         930
Met Cys Gln Arg Ala Val Asp Gln Thr Ser Asp Trp Met Met Val Asp
                180                 185                 190 aca tgg gag ccg atg cac aag gag tac cag cca act gcc atc gta ctg         978
Thr Trp Glu Pro Met His Lys Glu Tyr Gln Pro Thr Ala Ile Val Leu
            195                 200                 205 gat cat ttt gac tac gag atc aac act gtc cgc aaa ggt atc gat acc         1026
Asp His Phe Asp Tyr Glu Ile Asn Thr Val Arg Lys Gly Ile Asp Thr
        210                 215                 220 gga aaa ggc act cga aag cga gtg caa gtc gtc tta ttg gcc ggg gca         1074
Gly Lys Gly Thr Arg Lys Arg Val Gln Val Val Leu Leu Ala Gly Ala
225                 230                 235                 240 gat ttg gtc cat acc atg tct acg ccc gga gta tgg agt gag aag gat         1122
Asp Leu Val His Thr Met Ser Thr Pro Gly Val Trp Ser Glu Lys Asp
                245                 250                 255 ctc gat cat att ctt gga cag tac ggg gtatgttatg ttgtatctat               1169
Leu Asp His Ile Leu Gly Gln Tyr Gly
                260                 265 cctaaacttc gcgcaagcta actggtctag act ttc atc gtc gag cga agc ggg        1223
                                 Thr Phe Ile Val Glu Arg Ser Gly
                                                             270 aca gat att gac gag gcg ctc gcg gca ttg cag cca tgg aaa aag aat         1271
Thr Asp Ile Asp Glu Ala Leu Ala Ala Leu Gln Pro Trp Lys Lys Asn
            275                 280                 285 atc cat gtt att caa caa ctt att caa aat gac gtt agc agc act aag         1319
Ile His Val Ile Gln Gln Leu Ile Gln Asn Asp Val Ser Ser Thr Lys
290                 295                 300                 305 att cgc tta ttc ctc agg cga gat atg agc gta cgc tac ttg atc cct         1367
Ile Arg Leu Phe Leu Arg Arg Asp Met Ser Val Arg Tyr Leu Ile Pro
                310                 315                 320 gac ccg gtg att gag tac atc tat gag aat aac ctc tac atg gac gac         1415
Asp Pro Val Ile Glu Tyr Ile Tyr Glu Asn Asn Leu Tyr Met Asp Asp
            325                 330                 335 ggt acg aca caa ccg acg gcc gac aag ggc aag aca cga gag gag ccc         1463
Gly Thr Thr Gln Pro Thr Ala Asp Lys Gly Lys Thr Arg Glu Glu Pro
        340                 345                 350 gcg cct tca aat tagcattgct caaaaagcca gataaggcca cgcgacgacg             1515
Ala Pro Ser Asn
        355 tcatgacgac cattgctggt ttcacgaaga tatcaaaccg ccgggcgaat gcaatctctg       1575 cgctgatctg agcaagcact gattccggta agccgcaagt tgggggagga tttaatgagc      1635 ccaaccgtat gggtttgttc cggtcaagtc actgcgatta acgacacgcc ttatgactgt      1695 catatcgaca ggtccctctc cagagccggc ctacacaaca gtgatgctgg cgttcttcta      1755 ttccaagccc tcaacatcta agtgcagcgg cgaattc                                1792

<210> SEQ ID NO 8
```

```
<211> LENGTH: 27
<212> TYPE: PRT
<213> ORGANISM: Aspergillus nidulans

<400> SEQUENCE: 8

Met Arg Gly Cys Ile Leu Leu Leu Arg Gly Pro Glu Gly Glu Gln Ala
 1               5                  10                  15

Arg Thr Asp Pro Ala Lys Ile Ser Pro Leu Asp
            20                  25

<210> SEQ ID NO 9
<211> LENGTH: 1792
<212> TYPE: DNA
<213> ORGANISM: Aspergillus nidulans

<400> SEQUENCE: 9
cttaaggaca ctacctcgtc ttggagcctc atacgaggct acagtcatgt aatttaaaac       60
atcgctaggt gcactaaaga taaaacgcag gcgttatcca aaagactatg ccgacttctt      120
tatatcatgc accaggtcac ggatatctgc ctttcataaa agcatgccaa ccgagggttc      180
cgttatccag ttggagcgta tgcctcttat tgccatgcca ggacttcctt actcccctac      240
ataagaggaa gaggctcccg gtcttcccct tgtccgggcg tgactaggcc gcttttaaag      300
gggagagctc agaagcgaga gggggggtgt gccgactgat tgggaaggta agaacgggcg      360
taggtcggtc ggtcggaaaa cagcggcggg aaccaagccc gatgacagta gaagggaaga      420
agtagaagta cggcgagagc tgactttata agtcagagaa cgagactaaa tgtcaatgat      480
gcgcgtctgt gcgacgtgta gaggcgctag tactggctta ggtgagttct tgtcccgttg      540
ctaccggtcg cttacggggg gcgggccgc tgggggcaac tcctaatgca gaagggactt      600
atagcggact tcgcacacta cctactgggc cttttctgcg gcgataacga atatcgaacg      660
ccaagtaaga gtggataatg caaggacgtg gacgcgtaca agctttaccg gcggctaatg      720
cagtttgact cgtgtctaaa gctttattaa cctccaatag aaagcgggca gagcctgcgg      780
atggcgttcc gtccagaacg ctcacggtta gtgtccatca atgaaattgt gtgaagaagg      840
tatcaatgat aggtcctgac tagaccgccg aaatcttaac gttacacggt tgctcggcac      900
ctggtttgca gtctgaccta ctaccaccta tgtaccctcg gctacgtgtt cctcatggtc      960
ggttgacggt agcatgacct agtaaaactg atgctctagt tgtgacaggc gtttccatag     1020
ctatggcctt tccgtgagc tttcgctcac gttcagcaga ataaccggcc ccgtctaaac     1080
caggtatggt acagatgcgg gcctcatacc tcactcttcc tagagctagt ataagaacct     1140
gtcatgcccc atacaataca acatagatag gatttgaagc gcgttcgatt gaccagatct     1200
gaaagtagca gctcgcttcg ccctgtctat aactgctccg cgagcgccgt aacgtcggta     1260
cctttttctt ataggtacaa taagttgttg aataagtttt actgcaatcg tcgtgattct     1320
aagcgaataa ggagtccgct ctatactcgc atgcgatgaa ctagggactg ggccactaac     1380
tcatgtagat actcttattg gagatgtacc tgctgccatg ctgtgttggc tgccggctgt     1440
tcccgttctg tgctctcctc gggcgcggaa gtttaatcgt aacgagtttt tcggtctatt     1500
ccggtgcgct gctgcagtac tgctggtaac gaccaaagtg cttctatagt ttggcggccc     1560
gcttacgtta gagacgcgac tagactcgtt cgtgactaag gccattcggc gttcaacccc     1620
ctcctaaatt actcggggttg gcataccaa acaaggccag ttcagtgacg ctaattgctg     1680
tgcggaatac tgacagtata gctgtccagg gagaggtctc ggccggatgt gttgtcacta     1740
cgaccgcaag aagataaggt tcgggagttg tagattcacg tcgccgctta ag            1792
```

<210> SEQ ID NO 10
<211> LENGTH: 1899
<212> TYPE: DNA
<213> ORGANISM: Aspergillus nidulans
<220> FEATURE:
<221> NAME/KEY: CDS
<222> LOCATION: (453)...(627)
<221> NAME/KEY: CDS
<222> LOCATION: (686)...(890)
<221> NAME/KEY: CDS
<222> LOCATION: (949)...(1157)
<221> NAME/KEY: CDS
<222> LOCATION: (1212)...(1288)

<400> SEQUENCE: 10

```
ttgccttctt agacttgata tctgaaggaa tataacggaa gagatcatct ggtttgatgg    60
tactgtatta gcgggagcac gtgattattt ccctccgata ggccagtggc gtatgtcata   120
aggaagactg acgcctggag gggaaaacac ctccctcgcc cgagttccat cttatcactt   180
tcacgctcga tctctccaag tttctggctt cattgactga gtcgctcgcc ttgcctagtg   240
ggtagattta gatctagtcg caaatcactt gcctacattc tcgaacctgt ttgttcagcc   300
ttgcggttcc cctcactact tatctcttct taccttctac cgtttcgaaa acacttcctc   360
ctgcggcgag actagtatct atcgcctgtc gcccactttc accaccgtgt tcactagga   420 gaatagtgaa agactcaagt cgtctaccaa aa atg tgg tca tgg ttc cgg tgg    473
                                    Met Trp Ser Trp Phe Arg Trp
                                     1               5
```

```
tgc ggc cgc gca gaa gcg caa gga agc gcc gaa aac gca atc ctc cag    521
Cys Gly Arg Ala Glu Ala Gln Gly Ser Ala Glu Asn Ala Ile Leu Gln
        10                  15                  20
```

```
ctt cga agc cac ctt gac atg cta cag aag cga gaa aag cac cta gaa    569
Leu Arg Ser His Leu Asp Met Leu Gln Lys Arg Glu Lys His Leu Glu
 25                  30                  35
```

```
aac caa atg aac gaa caa gag gcc atc gct aaa aag aac gtg acc acg    617
Asn Gln Met Asn Glu Gln Glu Ala Ile Ala Lys Lys Asn Val Thr Thr
 40                  45                  50                  55
```

```
aat aag aac g gtgtgtatat tatgggacct ttatacaagt tcccatgctg           667
Asn Lys Asn
```

```
atttgaccac caccgcag cc gcc aaa gcc gcg ctc cga cgg aaa aag gtg     717
                    Ala Ala Lys Ala Ala Leu Arg Arg Lys Lys Val
                                 60                  65
```

```
cac gag aag aac tta gaa cag acg cag gct cag att gta cag ctt gag    765
His Glu Lys Asn Leu Glu Gln Thr Gln Ala Gln Ile Val Gln Leu Glu
 70                  75                  80                  85
```

```
cag cag ata tac tct att gaa gcc gcc aat att aac cac gag acc ctg    813
Gln Gln Ile Tyr Ser Ile Glu Ala Ala Asn Ile Asn His Glu Thr Leu
         90                  95                 100
```

```
gcc gcc atg aag gcc gcc ggt gca gct atg gag aag att cac aac ggc    861
Ala Ala Met Lys Ala Ala Gly Ala Ala Met Glu Lys Ile His Asn Gly
        105                 110                 115
```

```
atg acc gtc gaa cag gtc gac gag aca at gtacgtccct tactgtaccg       910
Met Thr Val Glu Gln Val Asp Glu Thr Met
        120                 125
```

```
ctggtgacat accggaattg gcatgctaac agactcag g gac aaa ctg cgg gaa    964
                                          Asp Lys Leu Arg Glu
                                                  130
```

```
caa caa gcc atc aac gac gaa atc gcg att gcc atc aca aac ccg ggg   1012
Gln Gln Ala Ile Asn Asp Glu Ile Ala Ile Ala Ile Thr Asn Pro Gly
        135                 140                 145
```

```
ttc ggc gag cag gtg gac gaa gaa gat ctg gag gcg gaa ctc gag ggc      1060
Phe Gly Glu Gln Val Asp Glu Glu Asp Leu Glu Ala Glu Leu Glu Gly
    150                 155                 160 atg gag cag gag gct atg gac gag cgc atg ctc cac aca ggc aca gta      1108
Met Glu Gln Glu Ala Met Asp Glu Arg Met Leu His Thr Gly Thr Val
165                 170                 175                 180 cca gtt gca gat cag ctc aat cgg cta cct gcg cca gcg aat gca gaa      1156
Pro Val Ala Asp Gln Leu Asn Arg Leu Pro Ala Pro Ala Asn Ala Glu
                185                 190                 195 c gtaaggctct ccctttccca cctcaaaagc gaactccgac tgacagcctt             1207 ccag cc gcc aaa gcg aaa cag aaa gca gaa gaa gaa gac gag gaa gcc      1255
     Pro Ala Lys Ala Lys Gln Lys Ala Glu Glu Glu Asp Glu Glu Ala
             200                 205                 210 gag ttg gag aag tta cgc gcg gaa atg gcc atg tgagagtggt cctggtgctt    1308
Glu Leu Glu Lys Leu Arg Ala Glu Met Ala Met
            215                 220 tggtctcttt ggtctaactt taatcttttt tcttcccct acacatatga tgaacaggga     1368
atcgttatca tgacgcacta cgattagcca agcactgtgt tcttttttccg tcggctcgtt   1428 gcgattcctt cttctccgcg gcgtaattac ttatctagtt gtaccaacta ccccgcgagg    1488
cttctgttga ggcgagagcg aaagcccaga cgtgtcgccc ttgccctgat tactggccac    1548
tcccgtccga gcacgctacc tccgttctgt ccacgctgtg tatcccactc tgtaataatc    1608
taccaagtga atacttttct ggatgatttg aagggcctat gtttcctacg ccatcatgtc    1668
attagatatg ttttgtggat catgtttccc cagcgcaatt gatgcccatt tgcagttcac    1728
actcgtgtca tatgaacctc agaatatgaa agccgcttct caacccagca aaacgtcact    1788
gaggattaaa attgagtaat tgagtaaaac taaattagta gctagataac tcccgtttcc    1848
caccagacct aacaccgtcc aaacagataa tcaacaagga aagaaagaa a              1899

<210> SEQ ID NO 11
<211> LENGTH: 58
<212> TYPE: PRT
<213> ORGANISM: Aspergillus nidulans

<400> SEQUENCE: 11

Met Trp Ser Trp Phe Arg Trp Cys Gly Arg Ala Glu Ala Gln Gly Ser
1               5                   10                  15

Ala Glu Asn Ala Ile Leu Gln Leu Arg Ser His Leu Asp Met Leu Gln
            20                  25                  30

Lys Arg Glu Lys His Leu Glu Asn Gln Met Asn Glu Gln Glu Ala Ile
        35                  40                  45

Ala Lys Lys Asn Val Thr Thr Asn Lys Asn
    50                  55

<210> SEQ ID NO 12
<211> LENGTH: 1899
<212> TYPE: DNA
<213> ORGANISM: Aspergillus nidulans

<400> SEQUENCE: 12
aacggaagaa tctgaactat agacttcctt atattgcctt ctctagtaga ccaaactacc     60
atgacataat cgccctcgtg cactaataaa gggaggctat ccggtcaccg catacagtat    120
tccttctgac tgcggacctc cccttttgtg gagggagcgg gctcaaggta gaatagtgaa    180
agtgcgagct agagaggttc aaagaccgaa gtaactgact cagcgagcgg aacggatcac    240
ccatctaaat ctagatcagc gtttagtgaa cggatgtaag agcttggaca aacaagtcgg    300
```

```
aacgccaagg ggagtgatga atagagaaga atggaagatg gcaaagcttt tgtgaaggag      360
gacgccgctc tgatcataga tagcggacag cgggtgaaag tggtggcaca aagtgatcct      420
cttatcactt tctgagttca gcagatggtt tttacaccag taccaaggcc accacgccgg      480
cgcgtcttcg cgttccttcg cggcttttgc gttaggaggt cgaagcttcg gtggaactgt      540
acgatgtctt cgctcttttc gtggatcttt tggtttactt gcttgttctc cggtagcgat      600
ttttcttgca ctggtgctta ttcttgccac acatataata ccctggaaat atgttcaagg      660
gtacgactaa actggtggtg gcgtcggcgg tttcggcgcg aggctgcctt tttccacgtg      720
ctcttcttga atcttgtctg cgtccgagtc taacatgtcg aactcgtcgt ctatatgaga      780
taacttcggc ggttataatt ggtgctctgg accggcggg acttccggcg ccacgtcga       840
tacctcttct aagtgttgcc gtactggcag cttgtccagc tgctctgtta catgcaggga      900
atgacatggc gaccactgta tggccttaac cgtacgattg tctgagtccc tgtttgacgc      960
ccttgttgtt cggtagttgc tgctttagcg ctaacggtag tgtttgggcc ccaagccgct     1020
cgtccacctg cttcttctag acctccgcct tgagctcccg tacctcgtcc tccgataccct    1080
gctcgcgtac gaggtgtgtc cgtgtcatgg tcaacgtcta gtcgagttag ccgatggacg     1140
cggtcgctta cgtcttgcat tccgagaggg aaagggtgga gttttcgctt gaggctgact     1200
gtcggaaggt cggcggtttc gctttgtctt tcgtcttctt cttctgctcc ttcggctcaa     1260
cctcttcaat gcgcgccttt accggtacac tctcaccagg accacgaaac cagagaaacc     1320
agattgaaat tagaaaaaag aaggggatg tgtatactac ttgtcccta gcaatagtac       1380
tgcgtgatgc taatcggttc gtgacacaag aaaaaggcag ccgagcaacg ctaaggaaga     1440
agaggcgccg cattaatgaa tagatcaaca tggttgatgg ggcgctccga agacaactcc     1500
gctctcgctt tcgggtctgc acagcgggaa cgggactaat gaccggtgag ggcaggctcg     1560
tgcgatggag gcaagacagg tgcgacacat agggtgagac attattagat ggttcactta     1620
tgaaaagacc tactaaactt cccggataca aggatgcgg tagtacagta atctatacaa      1680
aacacctagt acaaagggt cgcgttaact acgggtaaac gtcaagtgtg agcacagtat      1740
acttggagtc ttatactttc ggcgaagagt tgggtcgttt tgcagtgact cctaatttta     1800
actcattaac tcattttgat ttaatcatcg atctattgag ggcaaagggt ggtctggatt     1860
gtggcaggtt tgtctattag ttgttccttt tctttctttt                           1899
```

```
<210> SEQ ID NO 13
<211> LENGTH: 3800
<212> TYPE: DNA
<213> ORGANISM: Saccharomyces cerevisiae
<220> FEATURE:
<221> NAME/KEY: CDS
<222> LOCATION: (306)...(3458)

<400> SEQUENCE: 13
tttttcttgt cagtctgaaa attttcatt tggtttttg aaaaaaatcc tgcctaatat        60
ggtatcaaga ggaataacaa gaaaaaaaa tcatggggga tacaaaggaa acaaggaga       120
taatgcaggt tatactgaat tgctcatagt attagcctaa agcactttac ctctgattta     180
ttgcatctat cgtattcttg agttattgcg acttttaaaa tccgtgcacc gcatatgaaa     240
gggtagagcc ttcgtgtttg tttacctttt tagctctttg aagatcaaac aaaaacactt     300
cagta atg cct aca gcc ttg gat aag aca aag aag tta aca gcc gcg ccc    350
      Met Pro Thr Ala Leu Asp Lys Thr Lys Lys Leu Thr Ala Ala Pro
        1               5                  10                  15
```

| | | | | | | | | | | | | | | |
|---|---|---|---|---|---|---|---|---|---|---|---|---|---|---|
| atc | atg | caa | gat | cct | gat | ggt | att | gac | att | aat | acg | aaa | atc | ttt | aac | 398 |
| Ile | Met | Gln | Asp | Pro | Asp | Gly | Ile | Asp | Ile | Asn | Thr | Lys | Ile | Phe | Asn |
| | | 20 | | | | | 25 | | | | | 30 | | | |

| tca | gtt | gct | gaa | gta | ttt | caa | aag | gca | cag | ggt | tct | tat | gca | gga | cac | 446 |
| Ser | Val | Ala | Glu | Val | Phe | Gln | Lys | Ala | Gln | Gly | Ser | Tyr | Ala | Gly | His |
| | | | 35 | | | | | 40 | | | | | 45 | | |

| agg | aag | cat | ata | gca | gtt | ttg | aag | aaa | att | cag | tca | aag | gct | gtt | gag | 494 |
| Arg | Lys | His | Ile | Ala | Val | Leu | Lys | Lys | Ile | Gln | Ser | Lys | Ala | Val | Glu |
| | | | 50 | | | | | 55 | | | | | 60 | | |

| caa | ggc | tat | gaa | gat | gct | ttt | aac | ttt | tgg | ttc | gat | aaa | tta | gtt | act | 542 |
| Gln | Gly | Tyr | Glu | Asp | Ala | Phe | Asn | Phe | Trp | Phe | Asp | Lys | Leu | Val | Thr |
| 65 | | | | | 70 | | | | | 75 | | | | | |

| aag | atc | ctt | cct | ctg | aaa | aag | aat | gag | att | atc | gga | gac | agg | ata | gta | 590 |
| Lys | Ile | Leu | Pro | Leu | Lys | Lys | Asn | Glu | Ile | Ile | Gly | Asp | Arg | Ile | Val |
| 80 | | | | | 85 | | | | | 90 | | | | | 95 |

| aag | tta | gta | gct | gca | ttt | ata | gct | tct | tta | gaa | agg | gag | ttg | ata | ttg | 638 |
| Lys | Leu | Val | Ala | Ala | Phe | Ile | Ala | Ser | Leu | Glu | Arg | Glu | Leu | Ile | Leu |
| | | | | 100 | | | | | 105 | | | | | 110 | |

| gcc | aaa | aaa | caa | aac | tat | aag | ctc | acg | aat | gat | gaa | gaa | ggg | ata | ttc | 686 |
| Ala | Lys | Lys | Gln | Asn | Tyr | Lys | Leu | Thr | Asn | Asp | Glu | Glu | Gly | Ile | Phe |
| | | | 115 | | | | | 120 | | | | | 125 | | |

| tca | agg | ttc | gtc | gat | cag | ttc | ata | aga | cat | gtt | ttg | cgt | ggt | gtg | gaa | 734 |
| Ser | Arg | Phe | Val | Asp | Gln | Phe | Ile | Arg | His | Val | Leu | Arg | Gly | Val | Glu |
| | | 130 | | | | | 135 | | | | | 140 | | | |

| agc | cct | gac | aag | aac | gtc | aga | ttt | aga | gtt | tta | cag | tta | tta | gcc | gtt | 782 |
| Ser | Pro | Asp | Lys | Asn | Val | Arg | Phe | Arg | Val | Leu | Gln | Leu | Leu | Ala | Val |
| | 145 | | | | | 150 | | | | | 155 | | | | |

| ata | atg | gat | aat | ata | ggg | gaa | atc | gat | gaa | tca | ctt | ttc | aat | tta | tta | 830 |
| Ile | Met | Asp | Asn | Ile | Gly | Glu | Ile | Asp | Glu | Ser | Leu | Phe | Asn | Leu | Leu |
| 160 | | | | | 165 | | | | | 170 | | | | | 175 |

| ata | ttg | tct | tta | aat | aag | agg | att | tat | gat | aga | gaa | cca | acg | gtt | agg | 878 |
| Ile | Leu | Ser | Leu | Asn | Lys | Arg | Ile | Tyr | Asp | Arg | Glu | Pro | Thr | Val | Arg |
| | | | | 180 | | | | | 185 | | | | | 190 | |

| ata | cag | gct | gtg | ttt | tgt | tta | act | aaa | ttt | cag | gat | gaa | gag | caa | act | 926 |
| Ile | Gln | Ala | Val | Phe | Cys | Leu | Thr | Lys | Phe | Gln | Asp | Glu | Glu | Gln | Thr |
| | | | 195 | | | | | 200 | | | | | 205 | | |

| gaa | cat | tta | act | gag | ctt | tct | gat | aat | gaa | gaa | aat | ttt | gaa | gct | acg | 974 |
| Glu | His | Leu | Thr | Glu | Leu | Ser | Asp | Asn | Glu | Glu | Asn | Phe | Glu | Ala | Thr |
| | | 210 | | | | | 215 | | | | | 220 | | | |

| aga | act | cta | gtt | gct | tct | atc | cag | aac | gat | ccg | tca | gct | gaa | gta | cgg | 1022 |
| Arg | Thr | Leu | Val | Ala | Ser | Ile | Gln | Asn | Asp | Pro | Ser | Ala | Glu | Val | Arg |
| | 225 | | | | | 230 | | | | | 235 | | | | |

| agg | gct | gca | atg | ctg | aat | ttg | atc | aat | gat | aat | aat | act | aga | ccg | tat | 1070 |
| Arg | Ala | Ala | Met | Leu | Asn | Leu | Ile | Asn | Asp | Asn | Asn | Thr | Arg | Pro | Tyr |
| 240 | | | | | 245 | | | | | 250 | | | | | 255 |

| atc | ttg | gag | agg | gct | aga | gat | gta | aac | atc | gtt | aat | aga | agg | ctc | gtg | 1118 |
| Ile | Leu | Glu | Arg | Ala | Arg | Asp | Val | Asn | Ile | Val | Asn | Arg | Arg | Leu | Val |
| | | | | 260 | | | | | 265 | | | | | 270 | |

| tat | tcg | aga | att | ttg | aaa | tca | atg | gga | aga | aag | tgt | ttc | gat | gat | att | 1166 |
| Tyr | Ser | Arg | Ile | Leu | Lys | Ser | Met | Gly | Arg | Lys | Cys | Phe | Asp | Asp | Ile |
| | | | 275 | | | | | 280 | | | | | 285 | | |

| gag | ccg | cat | att | ttt | gat | caa | ttg | att | gag | tgg | ggt | tta | gaa | gat | agg | 1214 |
| Glu | Pro | His | Ile | Phe | Asp | Gln | Leu | Ile | Glu | Trp | Gly | Leu | Glu | Asp | Arg |
| | | 290 | | | | | 295 | | | | | 300 | | | |

| gaa | tta | tca | gtg | aga | aat | gcg | tgt | aag | aga | ctc | att | gct | cat | gat | tgg | 1262 |
| Glu | Leu | Ser | Val | Arg | Asn | Ala | Cys | Lys | Arg | Leu | Ile | Ala | His | Asp | Trp |
| | 305 | | | | | 310 | | | | | 315 | | | | |

| tta | aat | gct | ctg | gat | ggc | gat | ttg | ata | gaa | tta | cta | gaa | aaa | ttg | gat | 1310 |
| Leu | Asn | Ala | Leu | Asp | Gly | Asp | Leu | Ile | Glu | Leu | Leu | Glu | Lys | Leu | Asp |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 320 |     |     |     |     | 325 |     |     |     |     | 330 |     |     |     |     | 335 |      |
| gtc | tca | aga | tcc | tca | gtg | tgt | gtt | aag | gct | ata | gaa | gca | ctt | ttt | caa | 1358 |
| Val | Ser | Arg | Ser | Ser | Val | Cys | Val | Lys | Ala | Ile | Glu | Ala | Leu | Phe | Gln |      |
|     |     |     |     | 340 |     |     |     |     | 345 |     |     |     |     | 350 |     |      | tca agg cca gat ata tta tct aaa atc aaa ttt cct gaa agt att tgg    1406
Ser Arg Pro Asp Ile Leu Ser Lys Ile Lys Phe Pro Glu Ser Ile Trp
            355                 360                 365 aaa gac ttt acc gta gaa att gcc ttc ctc ttt cgg gct att tat ttg    1454
Lys Asp Phe Thr Val Glu Ile Ala Phe Leu Phe Arg Ala Ile Tyr Leu
            370                 375                 380 tac tgt ttg gat aat aat ata aca gaa atg ctg gaa gaa aac ttt cca    1502
Tyr Cys Leu Asp Asn Asn Ile Thr Glu Met Leu Glu Glu Asn Phe Pro
385                 390                 395 gaa gcc tca aaa tta tcc gag cat tta aac cat tat att ctt ctc aga    1550
Glu Ala Ser Lys Leu Ser Glu His Leu Asn His Tyr Ile Leu Leu Arg
400                 405                 410                 415 tat cat cac aac gac att tct aat gac tct cag tcg cat ttt gat tat    1598
Tyr His His Asn Asp Ile Ser Asn Asp Ser Gln Ser His Phe Asp Tyr
                420                 425                 430 aac act tta gag ttt att att gag caa cta tcg att gcc gcc gaa agg    1646
Asn Thr Leu Glu Phe Ile Ile Glu Gln Leu Ser Ile Ala Ala Glu Arg
            435                 440                 445 tat gat tat agc gat gag gtt gga agg aga tcg atg ctt aca gtg gta    1694
Tyr Asp Tyr Ser Asp Glu Val Gly Arg Arg Ser Met Leu Thr Val Val
            450                 455                 460 cga aat atg ctg gcc tta act aca ctc tcc gaa cct ctt att aaa att    1742
Arg Asn Met Leu Ala Leu Thr Thr Leu Ser Glu Pro Leu Ile Lys Ile
465                 470                 475 ggt att cgt gta atg aaa agt ctg tcc ata aat gaa aaa gat ttt gta    1790
Gly Ile Arg Val Met Lys Ser Leu Ser Ile Asn Glu Lys Asp Phe Val
480                 485                 490                 495 aca atg gca ata gaa atc att aat gat att aga gac gac gat att gaa    1838
Thr Met Ala Ile Glu Ile Ile Asn Asp Ile Arg Asp Asp Asp Ile Glu
                500                 505                 510 aaa caa gaa caa gaa gag aaa ata aaa agc aag aag att aat cgc aga    1886
Lys Gln Glu Gln Glu Glu Lys Ile Lys Ser Lys Lys Ile Asn Arg Arg
            515                 520                 525 aat gag act tcc gtc gat gaa gag gac gaa aac ggc aca cat aat gac    1934
Asn Glu Thr Ser Val Asp Glu Glu Asp Glu Asn Gly Thr His Asn Asp
            530                 535                 540 gaa gtt aac gag gat gaa gaa gac gac aat att tca tcc ttc cat tct    1982
Glu Val Asn Glu Asp Glu Glu Asp Asp Asn Ile Ser Ser Phe His Ser
545                 550                 555 gct gta gaa aac tta gtg cag gga aac ggc aac gta tct gag agt gac    2030
Ala Val Glu Asn Leu Val Gln Gly Asn Gly Asn Val Ser Glu Ser Asp
560                 565                 570                 575 ata ata aat aat ctc cca ccc gaa aag gaa gcg tcc tca gca aca att    2078
Ile Ile Asn Asn Leu Pro Pro Glu Lys Glu Ala Ser Ser Ala Thr Ile
                580                 585                 590 gtt ctc tgt ctt aca agg tca tca tat atg cta gaa cta gtt aac aca    2126
Val Leu Cys Leu Thr Arg Ser Ser Tyr Met Leu Glu Leu Val Asn Thr
            595                 600                 605 ccg tta aca gaa aac att tta att gcg tcg ttg atg gac act ttg atc    2174
Pro Leu Thr Glu Asn Ile Leu Ile Ala Ser Leu Met Asp Thr Leu Ile
            610                 615                 620 aca cca gcg gtt aga aat acc gcg cca aat att agg gag ctt ggt gtc    2222
Thr Pro Ala Val Arg Asn Thr Ala Pro Asn Ile Arg Glu Leu Gly Val
625                 630                 635 aag aac ctt ggt tta tgt tgt ctc ttg gat gtg aag ttg gct att gat    2270
Lys Asn Leu Gly Leu Cys Cys Leu Leu Asp Val Lys Leu Ala Ile Asp

```
Lys Asn Leu Gly Leu Cys Cys Leu Leu Asp Val Lys Leu Ala Ile Asp
640                 645                 650                 655 aac atg tac atc tta ggt atg tgc gtt tcg aaa ggt aat gca tca tta    2318
Asn Met Tyr Ile Leu Gly Met Cys Val Ser Lys Gly Asn Ala Ser Leu
                    660                 665                 670 aag tat att gcg tta caa gtc att gta gat att ttt tcc gta cat ggg    2366
Lys Tyr Ile Ala Leu Gln Val Ile Val Asp Ile Phe Ser Val His Gly
                675                 680                 685 aac act gtg gta gac gga gaa ggc aaa gtt gac tca atc tcg ttg cac    2414
Asn Thr Val Val Asp Gly Glu Gly Lys Val Asp Ser Ile Ser Leu His
            690                 695                 700 aaa ata ttt tac aag gtt tta aag aat aac ggt tta ccg gaa tgt cag    2462
Lys Ile Phe Tyr Lys Val Leu Lys Asn Asn Gly Leu Pro Glu Cys Gln
        705                 710                 715 gtg ata gca gcg gag ggt tta tgc aaa cta ttt ttg gca gac gtg ttc    2510
Val Ile Ala Ala Glu Gly Leu Cys Lys Leu Phe Leu Ala Asp Val Phe
720                 725                 730                 735 act gat gat gat ttg ttt gaa acg ttg gtt ttg tca tat ttt tcg ccg    2558
Thr Asp Asp Asp Leu Phe Glu Thr Leu Val Leu Ser Tyr Phe Ser Pro
                740                 745                 750 ata aat tcc tca aac gaa gcg ctg gta cag gca ttt gcc ttc tgc att    2606
Ile Asn Ser Ser Asn Glu Ala Leu Val Gln Ala Phe Ala Phe Cys Ile
                755                 760                 765 cca gtc tat tgt ttt tca cat cct gct cat caa caa cgt atg tct agg    2654
Pro Val Tyr Cys Phe Ser His Pro Ala His Gln Gln Arg Met Ser Arg
            770                 775                 780 acg gct gcg gac ata ctc tta aga cta tgt gtt ctt tgg gac gat tta    2702
Thr Ala Ala Asp Ile Leu Leu Arg Leu Cys Val Leu Trp Asp Asp Leu
        785                 790                 795 cag agc tct gta ata cct gag gta gac cgt gaa gct atg cta aag cct    2750
Gln Ser Ser Val Ile Pro Glu Val Asp Arg Glu Ala Met Leu Lys Pro
800                 805                 810                 815 aac ata ata ttt caa cag ttg cta ttt tgg act gat cca cgt aac tta    2798
Asn Ile Ile Phe Gln Gln Leu Leu Phe Trp Thr Asp Pro Arg Asn Leu
                820                 825                 830 gtt aac cag aca ggt tca aca aaa aaa gat aca gtg cag ctt aca ttc    2846
Val Asn Gln Thr Gly Ser Thr Lys Lys Asp Thr Val Gln Leu Thr Phe
                835                 840                 845 ttg atc gat gtg ctc aaa ata tac gct caa att gag aag aaa gaa ata    2894
Leu Ile Asp Val Leu Lys Ile Tyr Ala Gln Ile Glu Lys Lys Glu Ile
        850                 855                 860 aag aag atg atc atc act aat ata aac gct ata ttt ctt tct tct gaa    2942
Lys Lys Met Ile Ile Thr Asn Ile Asn Ala Ile Phe Leu Ser Ser Glu
865                 870                 875 caa gat tat tct act ttg aaa gaa ctt ctt gag tat tct gac gat att    2990
Gln Asp Tyr Ser Thr Leu Lys Glu Leu Leu Glu Tyr Ser Asp Asp Ile
880                 885                 890                 895 gca gaa aat gat aat tta gac aat gtt agc aaa aat gct ctg gac aag    3038
Ala Glu Asn Asp Asn Leu Asp Asn Val Ser Lys Asn Ala Leu Asp Lys
                900                 905                 910 cta agg aat aat ttg aat tcg ctg att gaa gag atc aat gaa agg tca    3086
Leu Arg Asn Asn Leu Asn Ser Leu Ile Glu Glu Ile Asn Glu Arg Ser
                915                 920                 925 gaa act cag aca aaa gat gag aac aac act gcg aat gac caa tac tcg    3134
Glu Thr Gln Thr Lys Asp Glu Asn Asn Thr Ala Asn Asp Gln Tyr Ser
            930                 935                 940 tct att ttg ggg aat tca ttc aat aaa tct tca aat gac acc ata gaa    3182
Ser Ile Leu Gly Asn Ser Phe Asn Lys Ser Ser Asn Asp Thr Ile Glu
        945                 950                 955
```

```
cac gct gct gat ata act gat gga aat aac aca gaa ttg act aaa aca      3230
His Ala Ala Asp Ile Thr Asp Gly Asn Asn Thr Glu Leu Thr Lys Thr
960                 965                 970                 975 act gtt aat att tcg gca gtt gac aat aca aca gag caa agt aac tca      3278
Thr Val Asn Ile Ser Ala Val Asp Asn Thr Thr Glu Gln Ser Asn Ser
                980                 985                 990 agg aaa aga acg aga tca gaa gcg gag caa att gac aca tcc aaa aac      3326
Arg Lys Arg Thr Arg Ser Glu Ala Glu Gln Ile Asp Thr Ser Lys Asn
            995                 1000                1005 ctg gaa aac atg agt att caa gac acg tca act gta gca aaa aat gta      3374
Leu Glu Asn Met Ser Ile Gln Asp Thr Ser Thr Val Ala Lys Asn Val
        1010                1015                1020 agt ttt gtt tta cct gac gag aaa tca gat gca atg tcc ata gat gaa      3422
Ser Phe Val Leu Pro Asp Glu Lys Ser Asp Ala Met Ser Ile Asp Glu
    1025                1030                1035 gaa gat aag gat tca gag tct ttc agc gag gtc tgt taaaattgat           3468
Glu Asp Lys Asp Ser Glu Ser Phe Ser Glu Val Cys
1040                1045                1050 atgcgagctc ttcatctatt taagttgatt ttttggttgt aaacatattt gtattttatt    3528
cttaggtttg ttaattcttc tacgcttacc agatatagat gctatatgtt attgcattac    3588
gcacattacc cggtgggaca aattatggaa atattccaag gctataaatt ctttggtgaa    3648
aggaactgaa attatgtcca gtaatgcacc agaaatggac atataaaact attaatgcat    3708
tttattacaa ttatcctaag aaaatatcct atatataatt aaagtaaaag aaataagatc    3768
aaaagaacaa aataaagtcg agtagaattt tc                                  3800
```

<210> SEQ ID NO 14
<211> LENGTH: 1051
<212> TYPE: PRT
<213> ORGANISM: Saccharomyces cerevisiae

<400> SEQUENCE: 14

```
Met Pro Thr Ala Leu Asp Lys Thr Lys Lys Leu Thr Ala Ala Pro Ile
1               5                   10                  15

Met Gln Asp Pro Asp Gly Ile Asp Ile Asn Thr Lys Ile Phe Asn Ser
            20                  25                  30

Val Ala Glu Val Phe Gln Lys Ala Gln Gly Ser Tyr Ala Gly His Arg
        35                  40                  45

Lys His Ile Ala Val Leu Lys Lys Ile Gln Ser Lys Ala Val Glu Gln
    50                  55                  60

Gly Tyr Glu Asp Ala Phe Asn Phe Trp Phe Asp Lys Leu Val Thr Lys
65                  70                  75                  80

Ile Leu Pro Leu Lys Lys Asn Glu Ile Ile Gly Asp Arg Ile Val Lys
                85                  90                  95

Leu Val Ala Ala Phe Ile Ala Ser Leu Glu Arg Glu Leu Ile Leu Ala
            100                 105                 110

Lys Lys Gln Asn Tyr Lys Leu Thr Asn Asp Glu Glu Gly Ile Phe Ser
        115                 120                 125

Arg Phe Val Asp Gln Phe Ile Arg His Val Leu Arg Gly Val Glu Ser
    130                 135                 140

Pro Asp Lys Asn Val Arg Phe Arg Val Leu Gln Leu Leu Ala Val Ile
145                 150                 155                 160

Met Asp Asn Ile Gly Glu Ile Asp Glu Ser Leu Phe Asn Leu Leu Ile
                165                 170                 175

Leu Ser Leu Asn Lys Arg Ile Tyr Asp Arg Glu Pro Thr Val Arg Ile
            180                 185                 190
```

-continued

```
Gln Ala Val Phe Cys Leu Thr Lys Phe Gln Asp Glu Glu Gln Thr Glu
        195                 200                 205
His Leu Thr Glu Leu Ser Asp Asn Glu Glu Asn Phe Glu Ala Thr Arg
        210                 215                 220
Thr Leu Val Ala Ser Ile Gln Asn Asp Pro Ser Ala Glu Val Arg Arg
225                 230                 235                 240
Ala Ala Met Leu Asn Leu Ile Asn Asp Asn Thr Arg Pro Tyr Ile
                245                 250                 255
Leu Glu Arg Ala Arg Asp Val Asn Ile Val Asn Arg Arg Leu Val Tyr
                260                 265                 270
Ser Arg Ile Leu Lys Ser Met Gly Arg Lys Cys Phe Asp Asp Ile Glu
        275                 280                 285
Pro His Ile Phe Asp Gln Leu Ile Glu Trp Gly Leu Glu Asp Arg Glu
        290                 295                 300
Leu Ser Val Arg Asn Ala Cys Lys Arg Leu Ile Ala His Asp Trp Leu
305                 310                 315                 320
Asn Ala Leu Asp Gly Asp Leu Ile Glu Leu Leu Glu Lys Leu Asp Val
                325                 330                 335
Ser Arg Ser Ser Val Cys Val Lys Ala Ile Glu Ala Leu Phe Gln Ser
        340                 345                 350
Arg Pro Asp Ile Leu Ser Lys Ile Lys Phe Pro Glu Ser Ile Trp Lys
        355                 360                 365
Asp Phe Thr Val Glu Ile Ala Phe Leu Phe Arg Ala Ile Tyr Leu Tyr
        370                 375                 380
Cys Leu Asp Asn Asn Ile Thr Glu Met Leu Glu Glu Asn Phe Pro Glu
385                 390                 395                 400
Ala Ser Lys Leu Ser Glu His Leu Asn His Tyr Ile Leu Leu Arg Tyr
                405                 410                 415
His His Asn Asp Ile Ser Asn Asp Ser Gln Ser His Phe Asp Tyr Asn
                420                 425                 430
Thr Leu Glu Phe Ile Ile Glu Gln Leu Ser Ile Ala Ala Glu Arg Tyr
        435                 440                 445
Asp Tyr Ser Asp Glu Val Gly Arg Arg Ser Met Leu Thr Val Val Arg
450                 455                 460
Asn Met Leu Ala Leu Thr Thr Leu Ser Glu Pro Leu Ile Lys Ile Gly
465                 470                 475                 480
Ile Arg Val Met Lys Ser Leu Ser Ile Asn Glu Lys Asp Phe Val Thr
                485                 490                 495
Met Ala Ile Glu Ile Ile Asn Asp Ile Arg Asp Asp Ile Glu Lys
        500                 505                 510
Gln Glu Gln Glu Glu Lys Ile Lys Ser Lys Lys Ile Asn Arg Arg Asn
        515                 520                 525
Glu Thr Ser Val Asp Glu Glu Asp Glu Asn Gly Thr His Asn Asp Glu
        530                 535                 540
Val Asn Glu Asp Glu Glu Asp Asp Asn Ile Ser Ser Phe His Ser Ala
545                 550                 555                 560
Val Glu Asn Leu Val Gln Gly Asn Gly Asn Val Ser Glu Ser Asp Ile
                565                 570                 575
Ile Asn Asn Leu Pro Pro Glu Lys Glu Ala Ser Ser Ala Thr Ile Val
                580                 585                 590
Leu Cys Leu Thr Arg Ser Ser Tyr Met Leu Glu Leu Val Asn Thr Pro
        595                 600                 605
```

```
Leu Thr Glu Asn Ile Leu Ile Ala Ser Leu Met Asp Thr Leu Ile Thr
        610                 615                 620

Pro Ala Val Arg Asn Thr Ala Pro Asn Ile Arg Glu Leu Gly Val Lys
625                 630                 635                 640

Asn Leu Gly Leu Cys Cys Leu Leu Asp Val Lys Leu Ala Ile Asp Asn
                645                 650                 655

Met Tyr Ile Leu Gly Met Cys Val Ser Lys Gly Asn Ala Ser Leu Lys
                660                 665                 670

Tyr Ile Ala Leu Gln Val Ile Val Asp Ile Phe Ser Val His Gly Asn
            675                 680                 685

Thr Val Val Asp Gly Glu Gly Lys Val Asp Ser Ile Ser Leu His Lys
        690                 695                 700

Ile Phe Tyr Lys Val Leu Lys Asn Asn Gly Leu Pro Glu Cys Gln Val
705                 710                 715                 720

Ile Ala Ala Glu Gly Leu Cys Lys Leu Phe Leu Ala Asp Val Phe Thr
                725                 730                 735

Asp Asp Asp Leu Phe Glu Thr Leu Val Leu Ser Tyr Phe Ser Pro Ile
                740                 745                 750

Asn Ser Ser Asn Glu Ala Leu Val Gln Ala Phe Ala Phe Cys Ile Pro
            755                 760                 765

Val Tyr Cys Phe Ser His Pro Ala His Gln Gln Arg Met Ser Arg Thr
            770                 775                 780

Ala Ala Asp Ile Leu Leu Arg Leu Cys Val Leu Trp Asp Asp Leu Gln
785                 790                 795                 800

Ser Ser Val Ile Pro Glu Val Asp Arg Glu Ala Met Leu Lys Pro Asn
                805                 810                 815

Ile Ile Phe Gln Gln Leu Leu Phe Trp Thr Asp Pro Arg Asn Leu Val
                820                 825                 830

Asn Gln Thr Gly Ser Thr Lys Lys Asp Thr Val Gln Leu Thr Phe Leu
            835                 840                 845

Ile Asp Val Leu Lys Ile Tyr Ala Gln Ile Glu Lys Lys Glu Ile Lys
        850                 855                 860

Lys Met Ile Ile Thr Asn Ile Asn Ala Ile Phe Leu Ser Ser Glu Gln
865                 870                 875                 880

Asp Tyr Ser Thr Leu Lys Glu Leu Leu Glu Tyr Ser Asp Asp Ile Ala
                885                 890                 895

Glu Asn Asp Asn Leu Asp Asn Val Ser Lys Asn Ala Leu Asp Lys Leu
                900                 905                 910

Arg Asn Asn Leu Asn Ser Leu Ile Glu Glu Ile Asn Glu Arg Ser Glu
            915                 920                 925

Thr Gln Thr Lys Asp Glu Asn Asn Thr Ala Asn Asp Gln Tyr Ser Ser
        930                 935                 940

Ile Leu Gly Asn Ser Phe Asn Lys Ser Ser Asn Asp Thr Ile Glu His
945                 950                 955                 960

Ala Ala Asp Ile Thr Asp Gly Asn Asn Thr Glu Leu Thr Lys Thr Thr
                965                 970                 975

Val Asn Ile Ser Ala Val Asp Asn Thr Thr Glu Gln Ser Asn Ser Arg
            980                 985                 990

Lys Arg Thr Arg Ser Glu Ala Glu Gln Ile Asp Thr Ser Lys Asn Leu
            995                 1000                1005

Glu Asn Met Ser Ile Gln Asp Thr Ser Thr Val Ala Lys Asn Val Ser
        1010                1015                1020

Phe Val Leu Pro Asp Glu Lys Ser Asp Ala Met Ser Ile Asp Glu Glu
```

Asp Lys Asp Ser Glu Ser Phe Ser Glu Val Cys
           1045                1050

<210> SEQ ID NO 15
<211> LENGTH: 3800
<212> TYPE: DNA
<213> ORGANISM: Saccharomyces cerevisiae

<400> SEQUENCE: 15

| | | | | | |
|---|---|---|---|---|---|
| aaaaagaaca | gtcagacttt | taaaaagtaa | accaaaaaac | ttttttttagg | acggattata | 60 |
| ccatagttct | ccttattgtt | cttttttttt | agtaccccct | atgtttcctt | ttgttcctct | 120 |
| attacgtcca | atatgactta | acgagtatca | taatcggatt | tcgtgaaatg | gagactaaat | 180 |
| aacgtagata | gcataagaac | tcaataacgc | tgaaaatttt | aggcacgtgg | cgtatacttt | 240 |
| cccatctcgg | aagcacaaac | aaatggaaaa | atcgagaaac | ttctagtttg | tttttgtgaa | 300 |
| gtcattacgg | atgtcggaac | ctattctgtt | tcttcaattg | tcggcgcggg | tagtacgttc | 360 |
| taggactacc | ataactgtaa | ttatgctttt | agaaattgag | tcaacgactt | cataaagttt | 420 |
| tccgtgtccc | aagaatacgt | cctgtgtcct | tcgtatatcg | tcaaaacttc | ttttaagtca | 480 |
| gtttccgaca | actcgttccg | atacttctac | gaaaattgaa | aaccaagcta | tttaatcaat | 540 |
| gattctagga | aggagacttt | ttcttactct | aatagcctct | gtcctatcat | ttcaatcatc | 600 |
| gacgtaaata | tcgaagaaat | ctttccctca | actataaccg | gttttttgtt | ttgatattcg | 660 |
| agtgcttact | acttcttccc | tataagagtt | ccaagcagct | agtcaagtat | tctgtacaaa | 720 |
| acgcaccaca | cctttcggga | ctgttcttgc | agtctaaatc | tcaaaatgtc | aataatcggc | 780 |
| aatattacct | attatatccc | ctttagctac | ttagtgaaaa | gttaaataat | tataacagaa | 840 |
| atttattctc | ctaaatacta | tctcttggtt | gccaatccta | tgtccgacac | aaaacaaatt | 900 |
| gatttaaagt | cctacttctc | gtttgacttg | taaattgact | cgaaagacta | ttacttcttt | 960 |
| taaaacttcg | atgctcttga | gatcaacgaa | gataggtctt | gctaggcagt | cgacttcatg | 1020 |
| cctcccgacg | ttacgactta | aactagttac | tattattatg | atctggcata | tagaacctct | 1080 |
| cccgatctct | acatttgtag | caattatctt | ccgagcacat | aagctcttaa | aactttagtt | 1140 |
| acccttcttt | cacaaagcta | ctataactcg | gcgtataaaa | actagttaac | taactcaccc | 1200 |
| caaatcttct | atcccttaat | agtcactctt | tacgcacatt | ctctgagtaa | cgagtactaa | 1260 |
| ccaatttacg | agaccaccg | ctaaactatc | ttaatgatct | tttaaccta | cagagttcta | 1320 |
| ggagtcacac | acaattccga | tatcttcgtg | aaaaagttag | ttccggtcta | tataatagat | 1380 |
| tttagtttaa | aggactttca | taaacctttc | tgaaatggca | tctttaacgg | aaggagaaag | 1440 |
| cccgataaat | aaacatgaca | aacctattat | tatattgtct | ttacgacctt | cttttgaaag | 1500 |
| gtcttcggag | ttttaatagg | ctcgtaaatt | tggtaatata | agaagagtct | atagtagtgt | 1560 |
| tgctgtaaag | attactgaga | gtcagcgtaa | aactaatatt | gtgaaatctc | aaataataac | 1620 |
| tcgttgatag | ctaacggcgg | ctttccatac | taatatcgct | actccaacct | tcctctagct | 1680 |
| acgaatgtca | ccatgcttta | tacgaccgga | attgatgtga | gaggcttgga | gaataatttt | 1740 |
| aaccataagc | acattacttt | tcagacaggt | atttactttt | tctaaaacat | tgttaccgtt | 1800 |
| atctttagta | attactataa | tctctgctgc | tataaacttt | tgttcttgtt | cttctctttt | 1860 |
| atttttcgtt | cttctaatta | gcgtctttac | tctgaaggca | gctacttctc | ctgcttttgc | 1920 |
| cgtgtgtatt | actgcttcaa | ttgctcctac | ttcttctgct | gttataaagt | aggaaggtaa | 1980 |

-continued

```
gacgacatct tttgaatcac gtcccttttgc cgttgcatag actctcactg tattatttat    2040
tagagggtgg gcttttcctt cgcaggagtc gttgttaaca agagacagaa tgttccagta    2100
gtatatacga tcttgatcaa ttgtgtggca attgtctttt gtaaaattaa cgcagcaact    2160
acctgtgaaa ctagtgtggt cgccaatctt tatggcgcgg tttataatcc ctcgaaccac    2220
agttcttgga accaaataca acagagaacc tacacttcaa ccgataacta ttgtacatgt    2280
agaatccata cacgcaaagc tttccattac gtagtaattt catataacgc aatgttcagt    2340
aacatctata aaaaggcat gtacccttgt gacaccatct gcctcttccg tttcaactga    2400
gttagagcaa cgtgtttat aaaatgttcc aaaatttctt attgccaaat ggccttacag    2460
tccactatcg tcgcctccca aatacgtttg ataaaaaccg tctgcacaag tgactactac    2520
taaacaaact ttgcaaccaa aacagtataa aaagcggcta tttaaggagt ttgcttcgcg    2580
accatgtccg taaacggaag acgtaaggtc agataacaaa aagtgtagga cgagtagttg    2640
ttgcatacag atcctgccga cgcctgtatg agaattctga tacacaagaa accctgctaa    2700
atgtctcgag acattatgga ctccatctgg cacttcgata cgatttcgga ttgtattata    2760
aagttgtcaa cgataaaacc tgactaggtg cattgaatca attggtctgt ccaagttgtt    2820
tttttctatg tcacgtcgaa tgtaagaact agctacacga gttttatatg cgagtttaac    2880
tcttctttct ttatttcttc tactagtagt gattatattt gcgatataaa gaaagaagac    2940
ttgttctaat aagatgaaac tttcttgaag aactcataag actgctataa cgtcttttac    3000
tattaaatct gttacaatcg ttttacgag acctgttcga ttccttatta aacttaagcg    3060
actaacttct ctagttactt tccagtcttt gagtctgttt tctactcttg ttgtgacgct    3120
tactggttat gagcagataa aacccctttaa gtaagttatt tagaagttta ctgtggtatc    3180
ttgtgcgacg actatattga ctacctttat tgtgtcttaa ctgattttgt tgacaattat    3240
aaagccgtca actgttatgt tgtctcgttt cattgagttc ctttcttgc tctagtcttc    3300 gcctcgttta actgtgtagg tttttggacc ttttgtactc ataagttctg tgcagttgac    3360 atcgttttt acattcaaaa caaatggac tgctctttag tctacgttac aggtatctac    3420
ttcttctatt cctaagtctc agaaagtcgc tccagacaat tttaactata cgctcgagaa    3480
gtagataaat tcaactaaaa aaccaacatt tgtataaaca taaataaga atccaaacaa    3540 ttaagaagat gcgaatggtc tatatctacg atatacaata acgtaatgcg tgtaatgggc    3600
cacctgtttt aatacctta taaggttccg atatttaaga aaccactttc cttgacttta    3660
atacaggtca ttacgtggtc tttacctgta tattttgata attacgtaaa ataatgttaa    3720
taggattctt ttataggata tatattaatt tcattttctt tattctagtt ttcttgtttt    3780
atttcagctc atcttaaaag                                                3800
```

<210> SEQ ID NO 16
<211> LENGTH: 2156
<212> TYPE: DNA
<213> ORGANISM: Saccharomyces cerevisiae
<220> FEATURE:
<221> NAME/KEY: CDS
<222> LOCATION: (543)...(1727)

<400> SEQUENCE: 16

```
tcttttggtg tcaatggtgt attattccga gttactccag gctaggttca ggagtaccaa      60
gaatgtactt tatttattta tacaccggag caagtcatat aattacgcaa acgattcgaa     120
attgttaaaa gcaggatcaa cgtatctcat ttcttttga aagacgggta atagaaagtc     180
```

-continued

```
tctgagtcgc accccacatg gatatcgtac tattcgtata tggaatgtaa aatactcgca      240
atacgatttt atttagcttc acaatctctc aaacttatcg tcttgatcaa tctttacgtt      300
ttaccaaata atcgcctgtt tctggccatt ttttgcttat accatctacc atactcgctg      360
tccatatgtg acggtgtcgt ctccaagaaa aataacaatg taaattgacc cagcgtgacg      420
acagtagact gtaagttata gtacaatcat actctacctt agtcactgtt cctccactgt      480
taagtagaga gagagagaga gtttaaagtg gagaaggcaa gaaaaagtgc acttattacg      540
```

| | | | | | | | | | | | | | | | | |
|---|---|---|---|---|---|---|---|---|---|---|---|---|---|---|---|---|
| ta atg | gat | ccc | acc | aaa | gca | ccc | gat | ttt | aaa | ccg | cca | cag | cca | aat | | 587 |
| Met | Asp | Pro | Thr | Lys | Ala | Pro | Asp | Phe | Lys | Pro | Pro | Gln | Pro | Asn | | |
| 1 | | | 5 | | | | | 10 | | | | | 15 | | | |

| gaa | gaa | cta | caa | cca | ccg | cca | gat | cca | aca | cat | acg | ata | cca | aaa | tct | 635 |
|---|---|---|---|---|---|---|---|---|---|---|---|---|---|---|---|---|
| Glu | Glu | Leu | Gln | Pro | Pro | Pro | Asp | Pro | Thr | His | Thr | Ile | Pro | Lys | Ser | |
| | | | 20 | | | | | 25 | | | | | 30 | | | |

| gga | ccc | ata | gtt | cca | tat | gtt | tta | gct | gat | tat | aat | tct | tcg | atc | gat | 683 |
|---|---|---|---|---|---|---|---|---|---|---|---|---|---|---|---|---|
| Gly | Pro | Ile | Val | Pro | Tyr | Val | Leu | Ala | Asp | Tyr | Asn | Ser | Ser | Ile | Asp | |
| | | | 35 | | | | | 40 | | | | | 45 | | | |

| gct | cct | ttc | aat | ctc | gac | att | tac | aaa | acc | ctg | tcg | tca | agg | aaa | aaa | 731 |
|---|---|---|---|---|---|---|---|---|---|---|---|---|---|---|---|---|
| Ala | Pro | Phe | Asn | Leu | Asp | Ile | Tyr | Lys | Thr | Leu | Ser | Ser | Arg | Lys | Lys | |
| | | 50 | | | | | 55 | | | | | 60 | | | | |

| aac | gcc | aac | tca | agc | aac | cga | atg | gac | cat | att | cca | tta | aat | act | agt | 779 |
|---|---|---|---|---|---|---|---|---|---|---|---|---|---|---|---|---|
| Asn | Ala | Asn | Ser | Ser | Asn | Arg | Met | Asp | His | Ile | Pro | Leu | Asn | Thr | Ser | |
| | 65 | | | | | 70 | | | | | 75 | | | | | |

| gac | ttc | cag | cca | cta | tct | cgg | gat | gta | tca | tcg | gag | gag | gaa | agt | gaa | 827 |
|---|---|---|---|---|---|---|---|---|---|---|---|---|---|---|---|---|
| Asp | Phe | Gln | Pro | Leu | Ser | Arg | Asp | Val | Ser | Ser | Glu | Glu | Glu | Ser | Glu | |
| 80 | | | | | 85 | | | | | 90 | | | | | 95 | |

| ggg | caa | tcg | aat | gga | att | gac | gct | act | cta | cag | gat | gtt | acg | atg | act | 875 |
|---|---|---|---|---|---|---|---|---|---|---|---|---|---|---|---|---|
| Gly | Gln | Ser | Asn | Gly | Ile | Asp | Ala | Thr | Leu | Gln | Asp | Val | Thr | Met | Thr | |
| | | | 100 | | | | | 105 | | | | | 110 | | | |

| ggg | aat | ttg | ggg | gta | ctg | aag | agc | caa | att | gct | gat | ttg | gaa | gaa | gtt | 923 |
|---|---|---|---|---|---|---|---|---|---|---|---|---|---|---|---|---|
| Gly | Asn | Leu | Gly | Val | Leu | Lys | Ser | Gln | Ile | Ala | Asp | Leu | Glu | Glu | Val | |
| | | | 115 | | | | | 120 | | | | | 125 | | | |

| cct | cac | aca | att | gta | aga | caa | gcc | aga | act | att | gaa | gat | tac | gaa | ttt | 971 |
|---|---|---|---|---|---|---|---|---|---|---|---|---|---|---|---|---|
| Pro | His | Thr | Ile | Val | Arg | Gln | Ala | Arg | Thr | Ile | Glu | Asp | Tyr | Glu | Phe | |
| | | 130 | | | | | 135 | | | | | 140 | | | | |

| cct | gta | cac | aga | ttg | acg | aaa | aag | tta | caa | gat | cct | gaa | aaa | ctg | cct | 1019 |
|---|---|---|---|---|---|---|---|---|---|---|---|---|---|---|---|---|
| Pro | Val | His | Arg | Leu | Thr | Lys | Lys | Leu | Gln | Asp | Pro | Glu | Lys | Leu | Pro | |
| | 145 | | | | | 150 | | | | | 155 | | | | | |

| ctg | atc | atc | gtt | gct | tgt | gga | tca | ttt | tct | ccc | ata | aca | tac | cta | cat | 1067 |
|---|---|---|---|---|---|---|---|---|---|---|---|---|---|---|---|---|
| Leu | Ile | Ile | Val | Ala | Cys | Gly | Ser | Phe | Ser | Pro | Ile | Thr | Tyr | Leu | His | |
| 160 | | | | | 165 | | | | | 170 | | | | | 175 | |

| ttg | aga | atg | ttt | gaa | atg | gct | tta | gat | gat | atc | aat | gag | caa | acg | cgt | 1115 |
|---|---|---|---|---|---|---|---|---|---|---|---|---|---|---|---|---|
| Leu | Arg | Met | Phe | Glu | Met | Ala | Leu | Asp | Asp | Ile | Asn | Glu | Gln | Thr | Arg | |
| | | | 180 | | | | | 185 | | | | | 190 | | | |

| ttt | gaa | gtg | gtt | ggt | ggt | tat | ttt | tct | cca | gta | agt | gat | aac | tat | caa | 1163 |
|---|---|---|---|---|---|---|---|---|---|---|---|---|---|---|---|---|
| Phe | Glu | Val | Val | Gly | Gly | Tyr | Phe | Ser | Pro | Val | Ser | Asp | Asn | Tyr | Gln | |
| | | | 195 | | | | | 200 | | | | | 205 | | | |

| aag | cga | ggg | tta | gcc | cca | gct | tat | cat | cgt | gtc | cgc | atg | tgc | gaa | tta | 1211 |
|---|---|---|---|---|---|---|---|---|---|---|---|---|---|---|---|---|
| Lys | Arg | Gly | Leu | Ala | Pro | Ala | Tyr | His | Arg | Val | Arg | Met | Cys | Glu | Leu | |
| | | 210 | | | | | 215 | | | | | 220 | | | | |

| gca | tgc | gag | cgg | aca | tca | tct | tgg | tta | atg | gtt | gat | gcc | tgg | gaa | tct | 1259 |
|---|---|---|---|---|---|---|---|---|---|---|---|---|---|---|---|---|
| Ala | Cys | Glu | Arg | Thr | Ser | Ser | Trp | Leu | Met | Val | Asp | Ala | Trp | Glu | Ser | |
| | 225 | | | | | 230 | | | | | 235 | | | | | |

| tta | caa | tca | agt | tat | aca | agg | aca | gca | aaa | gtc | ttg | gac | cat | ttc | aat | 1307 |
|---|---|---|---|---|---|---|---|---|---|---|---|---|---|---|---|---|
| Leu | Gln | Ser | Ser | Tyr | Thr | Arg | Thr | Ala | Lys | Val | Leu | Asp | His | Phe | Asn | |
| 240 | | | | | 245 | | | | | 250 | | | | | 255 | |

| cat | gaa | ata | aat | atc | aag | aga | ggt | gga | atc | atg | act | gta | gat | ggt | gaa | 1355 |
|---|---|---|---|---|---|---|---|---|---|---|---|---|---|---|---|---|
| His | Glu | Ile | Asn | Ile | Lys | Arg | Gly | Gly | Ile | Met | Thr | Val | Asp | Gly | Glu | |
| | | | 260 | | | | | 265 | | | | | 270 | | | |

```
aaa atg ggc gta aaa atc atg tta ttg gca ggc ggt gat ctt atc gaa    1403
Lys Met Gly Val Lys Ile Met Leu Leu Ala Gly Gly Asp Leu Ile Glu
            275                 280                 285 tcc atg ggc gag cct cat gtg tgg gct gat tca gac ctg cac cat att    1451
Ser Met Gly Glu Pro His Val Trp Ala Asp Ser Asp Leu His His Ile
        290                 295                 300 ttg ggt aat tat gga tgt ttg atc gtg gaa agg act ggt tct gat gtt    1499
Leu Gly Asn Tyr Gly Cys Leu Ile Val Glu Arg Thr Gly Ser Asp Val
    305                 310                 315 agg tcc ttc ttg ctt tcc cat gat atc atg tat gaa cac aga aga aat    1547
Arg Ser Phe Leu Leu Ser His Asp Ile Met Tyr Glu His Arg Arg Asn
320                 325                 330                 335 atc ctt att atc aaa caa ctt att tac aat gat att tcc tct acg aaa    1595
Ile Leu Ile Ile Lys Gln Leu Ile Tyr Asn Asp Ile Ser Ser Thr Lys
                340                 345                 350 gtg cgg ctt ttc atc aga cgt gga atg tca gtt caa tat ctt ctt cca    1643
Val Arg Leu Phe Ile Arg Arg Gly Met Ser Val Gln Tyr Leu Leu Pro
            355                 360                 365 aac tct gtc atc cgt tac atc caa gag tat aat cta tac att aat caa    1691
Asn Ser Val Ile Arg Tyr Ile Gln Glu Tyr Asn Leu Tyr Ile Asn Gln
        370                 375                 380 agt gaa ccg gtc aag cag gtc ttg gat agc aaa gag tgagtttatt         1737
Ser Glu Pro Val Lys Gln Val Leu Asp Ser Lys Glu
    385                 390                 395 acaactctga tactgcagca gttcaaattt accactttcc tcttcaaggt gcatagaaaa   1797
aaagttcctg gatgcacgat ttaaaatgtt tacagcagag caacaatcat gtgaacaatg   1857
tcaaacattt attttaacac ttaataatta taatataacc acaccagcgg taagtttcat   1917
aaggaaaacc tttcagacaa acattccagt gaatcgtata cgtaaatcag caaaattagc   1977
ttataaaata cagaatccga agatacttga tctactcgcg ttactattaa tgcgggtaat   2037
gatctatatt gaattttgca cgtctatagt aacttaaaag tcttgtaata tttgaagtaa   2097
caatgccgta taatactgca aatagcccct atcaatcgga atataccaaa acatcctttt   2156
```

<210> SEQ ID NO 17
<211> LENGTH: 395
<212> TYPE: PRT
<213> ORGANISM: Saccharomyces cerevisiae

<400> SEQUENCE: 17

```
Met Asp Pro Thr Lys Ala Pro Asp Phe Lys Pro Pro Gln Pro Asn Glu
  1               5                  10                  15

Glu Leu Gln Pro Pro Pro Asp Pro Thr His Thr Ile Pro Lys Ser Gly
                 20                  25                  30

Pro Ile Val Pro Tyr Val Leu Ala Asp Tyr Asn Ser Ser Ile Asp Ala
             35                  40                  45

Pro Phe Asn Leu Asp Ile Tyr Lys Thr Leu Ser Ser Arg Lys Lys Asn
         50                  55                  60

Ala Asn Ser Ser Asn Arg Met Asp His Ile Pro Leu Asn Thr Ser Asp
 65                  70                  75                  80

Phe Gln Pro Leu Ser Arg Asp Val Ser Glu Glu Ser Glu Gly
                 85                  90                  95

Gln Ser Asn Gly Ile Asp Ala Thr Leu Gln Asp Val Thr Met Thr Gly
                100                 105                 110

Asn Leu Gly Val Leu Lys Ser Gln Ile Ala Asp Leu Glu Glu Val Pro
            115                 120                 125
```

-continued

```
His Thr Ile Val Arg Gln Ala Arg Thr Ile Glu Asp Tyr Glu Phe Pro
    130                 135                 140
Val His Arg Leu Thr Lys Lys Leu Gln Asp Pro Glu Lys Leu Pro Leu
145                 150                 155                 160
Ile Ile Val Ala Cys Gly Ser Phe Ser Pro Ile Thr Tyr Leu His Leu
                165                 170                 175
Arg Met Phe Glu Met Ala Leu Asp Asp Ile Asn Glu Gln Thr Arg Phe
            180                 185                 190
Glu Val Val Gly Gly Tyr Phe Ser Pro Val Ser Asp Asn Tyr Gln Lys
        195                 200                 205
Arg Gly Leu Ala Pro Ala Tyr His Arg Val Arg Met Cys Glu Leu Ala
    210                 215                 220
Cys Glu Arg Thr Ser Ser Trp Leu Met Val Asp Ala Trp Glu Ser Leu
225                 230                 235                 240
Gln Ser Ser Tyr Thr Arg Thr Ala Lys Val Leu Asp His Phe Asn His
                245                 250                 255
Glu Ile Asn Ile Lys Arg Gly Gly Ile Met Thr Val Asp Gly Glu Lys
            260                 265                 270
Met Gly Val Lys Ile Met Leu Leu Ala Gly Gly Asp Leu Ile Glu Ser
        275                 280                 285
Met Gly Glu Pro His Val Trp Ala Asp Ser Asp Leu His His Ile Leu
    290                 295                 300
Gly Asn Tyr Gly Cys Leu Ile Val Glu Arg Thr Gly Ser Asp Val Arg
305                 310                 315                 320
Ser Phe Leu Leu Ser His Asp Ile Met Tyr Glu His Arg Arg Asn Ile
                325                 330                 335
Leu Ile Ile Lys Gln Leu Ile Tyr Asn Asp Ile Ser Ser Thr Lys Val
            340                 345                 350
Arg Leu Phe Ile Arg Arg Gly Met Ser Val Gln Tyr Leu Leu Pro Asn
        355                 360                 365
Ser Val Ile Arg Tyr Ile Gln Glu Tyr Asn Leu Tyr Ile Asn Gln Ser
    370                 375                 380
Glu Pro Val Lys Gln Val Leu Asp Ser Lys Glu
385                 390                 395
```

<210> SEQ ID NO 18
<211> LENGTH: 2156
<212> TYPE: DNA
<213> ORGANISM: Saccharomyces cerevisiae

<400> SEQUENCE: 18

| | | | | | |
|---|---|---|---|---|---|
| agaaaaccac | agttaccaca | taataaggct | caatgaggtc | cgatccaagt | cctcatggtt | 60 |
| cttacatgaa | ataaataaat | atgtggcctc | gttcagtata | ttaatgcgtt | tgctaagctt | 120 |
| taacaatttt | cgtcctagtt | gcatagagta | aagaaaaact | ttctgcccat | tatctttcag | 180 |
| agactcagcg | tggggtgtac | ctatagcatg | ataagcatat | accttacatt | ttatgagcgt | 240 |
| tatgctaaaa | taaatcgaag | tgttagagag | tttaatagc | agaactagtt | agaaatgcaa | 300 |
| aatggtttat | tagcggacaa | agaccggtaa | aaacgaata | tggtagatgg | tatgagcgac | 360 |
| aggtatacac | tgccacagca | gaggttcttt | ttattgttac | atttaactgg | gtcgcactgc | 420 |
| tgtcatctga | cattcaatat | catgttagta | tgagatggaa | tcagtgacaa | ggaggtgaca | 480 |
| attcatctct | ctctctctct | caaatttcac | ctcttccgtt | ctttttcacg | tgaataatgc | 540 |
| attacctagg | gtggtttcgt | gggctaaaat | ttggcggtgt | cggtttactt | cttgatgttg | 600 |

-continued

| | |
|---|---|
| gtggcggtct aggttgtgta tgctatggtt ttagacctgg gtatcaaggt atacaaaatc | 660 |
| gactaatatt aagaagctag ctacgaggaa agttagagct gtaaatgttt tgggacagca | 720 |
| gttccttttt tttgcggttg agttcgttgg cttacctggt ataaggtaat ttatgatcac | 780 |
| tgaaggtcgg tgatagagcc ctacatagta gcctcctcct ttcacttccc gttagcttac | 840 |
| cttaactgcg atgagatgtc ctacaatgct actgacccctt aaaccccccat gacttctcgg | 900 |
| tttaacgact aaaccttctt caaggagtgt gttaacattc tgttcggtct tgataacttc | 960 |
| taatgcttaa aggacatgtg tctaactgct ttttcaatgt tctaggactt tttgacggag | 1020 |
| actagtagca acgaacacct agtaaaagag ggtattgtat ggatgtaaac tcttacaaac | 1080 |
| tttaccgaaa tctactatag ttactcgttt gcgcaaaact tcaccaacca ccaataaaaa | 1140 |
| gaggtcattc actattgata gttttcgctc ccaatcgggg tcgaatagta gcacaggcgt | 1200 |
| acacgcttaa tcgtacgctc gcctgtagta gaaccaatta ccaactacgg acccttagaa | 1260 |
| atgttagttc aaatatgttcc tgtcgttttc agaacctggt aaagttagta ctttatttat | 1320 |
| agttctctcc accttagtac tgacatctac cacttttttta cccgcatttt tagtacaata | 1380 |
| accgtccgcc actagaatag cttaggtacc cgctcggagt acacacccga ctaagtctgg | 1440 |
| acgtggtata aaacccatta atacctacaa actagcacct ttcctgacca agactacaat | 1500 |
| ccaggaagaa cgaagggta ctatagtaca tacttgtgtc ttctttatag gaataatagt | 1560 |
| ttgttgaata aatgttacta taaggagat gctttcacgc cgaaaagtag tctgcacctt | 1620 |
| acagtcaagt tatagaagaa ggtttgagac agtaggcaat gtaggttctc atattagata | 1680 |
| tgtaattagt ttcacttggc cagttcgtcc agaacctatc gtttctcact caaataatgt | 1740 |
| tgagactatg acgtcgtcaa gtttaaatgg tgaaggaga agttccacgt atctttttt | 1800 |
| caaggaccta cgtgctaaat tttacaaatg tcgtctcgtt gttagtacac ttgttacagt | 1860 |
| ttgtaaataa aattgtgaat tattaatatt atattggtgt ggtcgccatt caaagtattc | 1920 |
| cttttggaaa gtctgtttgt aaggtcactt agcatatgca tttagtcgtt ttaatcgaat | 1980 |
| attttatgtc ttaggcttct atgaactaga tgagcgcaat gataattacg cccattacta | 2040 |
| gatataactt aaaacgtgca gatatcattg aattttcaga acattataaa cttcattgtt | 2100 |
| acggcatatt atgacgtatt atcgggatag ttagccttat atggttttgt aggaaa | 2156 |

<210> SEQ ID NO 19
<211> LENGTH: 3343
<212> TYPE: DNA
<213> ORGANISM: Saccharomyces cerevisiae
<220> FEATURE:
<221> NAME/KEY: CDS
<222> LOCATION: (1526)...(2728)

<400> SEQUENCE: 19

| | |
|---|---|
| gtttgaattg tgtttgtgtt agaaatttgt gtgctttaat gttatgttat aatgaaatct | 60 |
| tattagattt atttaacgtt tttgctgtgc ttataataaa cattacataa taaaaggagt | 120 |
| agaagaaagt ggtagagagg agtacaaatc tacctgccag aactctctcc ttatatatat | 180 |
| ttccagtggt gtctggatta cctacctcaa gccataccat atccatacca tatccataaa | 240 |
| cgcctacaaa atttctaccc caatccagca gcttctatca ctatctcgta taccaccata | 300 |
| ggcaccacca ctgtttgtgt aaatttactc ctgaggggg ggtggctcaa cacggtgtag | 360 |
| gccttcttcc cgcacaatcc gatgaaaccc cacaatcgcc tccgtctctt ccactgtgca | 420 |
| cggcgctagc tcaacatctt ccccgccaca tttactgtgg caaagaaggt gcataatcta | 480 |

-continued

```
aaaaaacata cgtatgagaa tggaaagggc aagataatat cggaccgtag tgagtcactt      540
gcttttggta ttgcaaccaa ctgccgcccc tcttcccgct cttgcaccaa aacgctaaat      600
gcccattgtg atggctcatc caccctcacg acgaagtaag acccggggca caagaaaata      660
cgagatcata acagttcgag tccgtttatt gtgtgcggtt ttggtacgct ttttcgtgag      720
gtgtactacc attcatgaga gtcgttttag gagctgtcat gaaagatatg tatcttgttg      780
atgaactgta aaaatttgca gaaattgcgc tattccgttt atttcattgt cgattcggtg      840
ttaatattag gggtacaaaa tatactagaa gttctccctc gaggatatag aatgcgcaa       900 atgggcattt gatgtgacac aaaatttgga caatataacg attcattttt agatcgttgt      960
tcaaccgtcc cagtggccga gtggttaagg cgatgcctgc tatttcctca gaaaagcaat     1020
taggcattgg gttttacctg cgcaggttcg aatcctgtct gtgacgcttt ttttaatttc     1080
tttactccat gacaaaagcg gataaaaatt cccgcattcg gcgtaaaaaa atccggtttt     1140 tttttttagca ctcgctgttt tgcctctac cgggtgaaaa atgacgatga agacggctgg    1200
aattgcgctg catccgctta cgtaggatag aacacctaca aagatttacg aactttattg     1260
ctcgaagatt cgctatccat atcttttag tttcccccca tttcacaatg ggataccgtt      1320 gtttttctg taggtacgct ttctcatagt taatagagtc agtaattcat ttcattttt       1380 gcagaaagga atttcttcac ctaatttaga atttcatcaa catttattgt atctgcatgg     1440
tataacaaat tagaaaaatt tggaagggaa aaaaaactg ttgcgtcaat tacttatacc     1500
agggatagaa aaaaaaaag gaaac atg gat ccc aca aga gct ccg gat ttc       1552
                              Met Asp Pro Thr Arg Ala Pro Asp Phe
                                1               5 aaa ccg cca tct gca gac gag gaa ttg att cct cca ccc gac ccg gaa       1600
Lys Pro Pro Ser Ala Asp Glu Glu Leu Ile Pro Pro Pro Asp Pro Glu
 10              15                  20                  25 tct aaa att ccc aaa tct att cca att att cca tac gtc tta gcc gat       1648
Ser Lys Ile Pro Lys Ser Ile Pro Ile Ile Pro Tyr Val Leu Ala Asp
             30                  35                  40 gcg aat tcc tct ata gat gca cct ttt aat att aag agg aag aaa aag       1696
Ala Asn Ser Ser Ile Asp Ala Pro Phe Asn Ile Lys Arg Lys Lys Lys
         45                  50                  55 cat cct aag cat cat cat cac cat cat cac agt cgt aaa gaa ggc aat       1744
His Pro Lys His His His His His His Ser Arg Lys Glu Gly Asn
     60                  65                  70 gat aaa aaa cat cag cat att cca ttg aac caa gac gac ttt caa cca       1792
Asp Lys Lys His Gln His Ile Pro Leu Asn Gln Asp Asp Phe Gln Pro
 75                  80                  85 ctt tcc gca gaa gtg tct tcc gaa gat gat gac gcg gat ttt aga tcc       1840
Leu Ser Ala Glu Val Ser Ser Glu Asp Asp Asp Ala Asp Phe Arg Ser
 90                  95                 100                 105 aag gag aga tac ggt tca gat tca acc aca gaa tca gaa act aga ggt       1888
Lys Glu Arg Tyr Gly Ser Asp Ser Thr Thr Glu Ser Glu Thr Arg Gly
            110                 115                 120 gtt cag aaa tat cag att gct gat tta gaa gaa gtt cca cat gga atc       1936
Val Gln Lys Tyr Gln Ile Ala Asp Leu Glu Glu Val Pro His Gly Ile
        125                 130                 135 gtt cgt caa gca aga acc ttg gaa gac tac gaa ttc ccc tca cac aga       1984
Val Arg Gln Ala Arg Thr Leu Glu Asp Tyr Glu Phe Pro Ser His Arg
    140                 145                 150 tta tcg aaa aaa tta ctg gat cca aat aaa ctg ccg tta gta ata gta       2032
Leu Ser Lys Lys Leu Leu Asp Pro Asn Lys Leu Pro Leu Val Ile Val
155                 160                 165 gca tgt ggg tct ttt tca cca atc acc tac ttg cat cta aga atg ttt       2080
```

```
                                                                    -continued Ala Cys Gly Ser Phe Ser Pro Ile Thr Tyr Leu His Leu Arg Met Phe
170                 175                 180                 185 gaa atg gct tta gat gca atc tct gaa caa aca agg ttt gaa gtc ata    2128
Glu Met Ala Leu Asp Ala Ile Ser Glu Gln Thr Arg Phe Glu Val Ile
            190                 195                 200 ggt gga tat tac tcc cct gtt agt gat aac tat caa aag caa ggc ttg    2176
Gly Gly Tyr Tyr Ser Pro Val Ser Asp Asn Tyr Gln Lys Gln Gly Leu
                205                 210                 215 gcc cca tcc tac cat aga gta cgt atg tgt gaa ttg gcc tgc gaa aga    2224
Ala Pro Ser Tyr His Arg Val Arg Met Cys Glu Leu Ala Cys Glu Arg
            220                 225                 230 acc tca tct tgg ttg atg gtg gat gca tgg gag tca ttg caa cct tca    2272
Thr Ser Ser Trp Leu Met Val Asp Ala Trp Glu Ser Leu Gln Pro Ser
        235                 240                 245 tac aca aga act gcc aag gtc ttg gat cat ttc aat cac gaa atc aat    2320
Tyr Thr Arg Thr Ala Lys Val Leu Asp His Phe Asn His Glu Ile Asn
250                 255                 260                 265 att aag aga ggt ggt gta gct act gtt act gga gaa aaa att ggt gtg    2368
Ile Lys Arg Gly Gly Val Ala Thr Val Thr Gly Glu Lys Ile Gly Val
                270                 275                 280 aaa ata atg ttg ctg gct ggt ggt gac cta ata gag tca atg ggt gaa    2416
Lys Ile Met Leu Leu Ala Gly Gly Asp Leu Ile Glu Ser Met Gly Glu
            285                 290                 295 cca aac gtt tgg gcg gac gcc gat tta cat cac att ctc ggt aat tac    2464
Pro Asn Val Trp Ala Asp Ala Asp Leu His His Ile Leu Gly Asn Tyr
        300                 305                 310 ggt tgt ttg att gtc gaa cgt act ggt tct gat gta agg tct ttt ttg    2512
Gly Cys Leu Ile Val Glu Arg Thr Gly Ser Asp Val Arg Ser Phe Leu
315                 320                 325 tta tcc cat gat att atg tat gaa cat aga agg aat att ctt atc atc    2560
Leu Ser His Asp Ile Met Tyr Glu His Arg Arg Asn Ile Leu Ile Ile
330                 335                 340                 345 aag caa ctc atc tat aat gat att tct tcc acg aaa gtt cgt cta ttt    2608
Lys Gln Leu Ile Tyr Asn Asp Ile Ser Ser Thr Lys Val Arg Leu Phe
                350                 355                 360 atc aga cgc gcc atg tct gta caa tat ttg tta cct aat tcg gtc atc    2656
Ile Arg Arg Ala Met Ser Val Gln Tyr Leu Leu Pro Asn Ser Val Ile
            365                 370                 375 agg tat atc caa gaa cat aga cta tat gtg gac caa acc gaa cct gtt    2704
Arg Tyr Ile Gln Glu His Arg Leu Tyr Val Asp Gln Thr Glu Pro Val
        380                 385                 390 aag caa gtt ctt gga aac aaa gaa tgatttgccg tccggaattg cttcgttctt   2758
Lys Gln Val Leu Gly Asn Lys Glu
395                 400 tctttcatct ttctctttac aatttccaat ttttccctac aggaattaat tggagggtac  2818
aagcgagtag aaatgtgaca tatgacttac ctatctgtgt tttagtatag ttttttttc   2878 tgtagtataa ttactttta cactaatttt ttcgccttt tctcttaaag agctaatttc    2938
tataaccttc agcggttata ccaaatataa aaaatggaag gaaaacaaac agtaagaaat  2998
aagcgcaaca gcacgttagt tcaccattgg attccaacat ttcaaaattt aatctaatgg  3058
caagagatat cacattttg accgtatttt tagaaagttg tggcgctgta aataatgatg   3118
aggcaggaaa attgttatct gcttggactt caaccgtacg cattgaggga ccggaatcaa  3178
ccgactctaa ttcattatat attccactgc taccacctgg aatgttgaaa gtatgtttct  3238
cctagcaaaa ttaaacccca tccgtgaatg aagcgttact aactataata actggtagct  3298
ttgtcactcg taccaggaaa agtgaagatt aaactgaatt ttaaa                  3343
```

```
<210> SEQ ID NO 20
<211> LENGTH: 401
<212> TYPE: PRT
<213> ORGANISM: Saccharomyces cerevisiae

<400> SEQUENCE: 20

Met Asp Pro Thr Arg Ala Pro Asp Phe Lys Pro Pro Ser Ala Asp Glu
 1               5                  10                  15

Glu Leu Ile Pro Pro Asp Pro Glu Ser Lys Ile Pro Lys Ser Ile
             20                  25                  30

Pro Ile Ile Pro Tyr Val Leu Ala Asp Ala Asn Ser Ser Ile Asp Ala
             35                  40                  45

Pro Phe Asn Ile Lys Arg Lys Lys His Pro Lys His His His
     50                  55                  60

His His His Ser Arg Lys Glu Gly Asn Asp Lys Lys His Gln His Ile
 65                  70                  75                  80

Pro Leu Asn Gln Asp Asp Phe Gln Pro Leu Ser Ala Glu Val Ser Ser
                 85                  90                  95

Glu Asp Asp Ala Asp Phe Arg Ser Lys Glu Arg Tyr Gly Ser Asp
            100                 105                 110

Ser Thr Thr Glu Ser Glu Thr Arg Gly Val Gln Lys Tyr Gln Ile Ala
            115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
                180                 185                 190

Ser Glu Gln Thr Arg Phe Glu Val Ile Gly Gly Tyr Tyr Ser Pro Val
            195                 200                 205

Ser Asp Asn Tyr Gln Lys Gln Gly Leu Ala Pro Ser Tyr His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
            260                 265                 270

Thr Val Thr Gly Glu Lys Ile Gly Val Lys Ile Met Leu Leu Ala Gly
            275                 280                 285

Gly Asp Leu Ile Glu Ser Met Gly Glu Pro Asn Val Trp Ala Asp Ala
290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Ile Lys Gln Leu Ile Tyr Asn Asp
            340                 345                 350

Ile Ser Ser Thr Lys Val Arg Leu Phe Ile Arg Arg Ala Met Ser Val
            355                 360                 365

Gln Tyr Leu Leu Pro Asn Ser Val Ile Arg Tyr Ile Gln Glu His Arg
370                 375                 380
```

Leu Tyr Val Asp Gln Thr Glu Pro Val Lys Gln Val Leu Gly Asn Lys
385                 390                 395                 400

Glu

<210> SEQ ID NO 21
<211> LENGTH: 3343
<212> TYPE: DNA
<213> ORGANISM: Saccharomyces cerevisiae

<400> SEQUENCE: 21

```
caaacttaac acaaacacaa tctttaaaca cacgaaatta caatacaata ttactttaga      60
ataatctaaa taaattgcaa aaacgacacg aatattattt gtaatgtatt attttcctca     120
tcttctttca ccatctctcc tcatgtttag atggacggtc ttgagagagg aatatatata     180
aaggtcacca cagacctaat ggatggagtt cggtatggta taggtatggt ataggtattt     240
gcggatgttt taagatgggg gttaggtcgt cgaagatagt gatagagcat atggtggtat     300
ccgtggtggt gacaaacaca tttaaatgag gactcccccc ccaccgagtt gtgccacatc     360
cggaagaagg gcgtgttagg ctactttggg gtgttagcgg aggcagagaa ggtgacacgt     420
gccgcgatcg agttgtagaa ggggcggtgt aaatgacacc gtttcttcca cgtattagat     480
tttttttgtat gcatactctt acctttcccg ttctattata gcctggcatc actcagtgaa     540
cgaaaaccat aacgttggtt gacggcgggg agaagggcga gaacgtggtt ttgcgattta     600
cgggtaacac taccgagtag gtgggagtgc tgcttcattc tgggcccccgt gttcttttat     660
gctctagtat tgtcaagctc aggcaaataa cacacgccaa aaccatgcga aaaagcactc     720
cacatgatgg taagtactct cagcaaaatc ctcgacagta ctttctatac atagaacaac     780
tacttgacat tttttaaacgt ctttaacgcg ataaggcaaa taagtaaca gctaagccac     840
aattataatc cccatgtttt tatgatctt caagagggag ctcctatatc cttacgcgtt     900
tacccgtaaa ctacactgtg ttttaaacct gttatattgc taagtaaaaa tctagcaaca     960
agttggcagg gtcaccggct caccaattcc gctacgacg ataaaggagt cttttcgtta    1020
atccgtaacc caaaatggac gcgtccaagc ttaggacaga cactgcgaaa aaaattaaag    1080
aaatgaggta ctgttttcgc ctatttttaa gggcgtaagc cgcatttttt taggccaaaa    1140
aaaaaatcgt gagcgacaaa acggagatg gcccactttt tactgctact ctgccgacc    1200
ttaacgcgac gtaggcgaat gcatcctatc ttgtggatgt ttctaaatgc ttgaaataac    1260
gagcttctaa gcgataggta tagaaaaatc aaagggggggt aaagtgttac cctatggcaa    1320
caaaaaagac atccatgcga aagagtatca attatctcag tcattaagta aagtaaaaaa    1380
cgtctttcct taagaagtg gattaaatct taagtagtt gtaaataaca tagacgtacc    1440
atattgttta atcttttttaa accttcccttt tttttttgac aacgcagtta atgaatatgg    1500
tccctatctt ttttttttttc ctttgtacct agggtgttct cgaggcctaa agtttggcgg    1560
tagacgtctg ctccttaact aaggaggtgg gctgggcctt agattttaag ggtttagata    1620
aggttaataa ggtatgcaga atcggctacg cttaaggaga tatctacgtg gaaaattata    1680
attctccttc ttttttcgtag gattcgtagt agtagtggta gtagtgtcag catttcttcc    1740
gttactattt tttgtagtcg tataaggtaa cttggttctg ctgaaagttg gtgaaaggcg    1800
tcttcacaga aggcttctac tactgcgcct aaaatctagg ttcctctcta tgccaagtct    1860
aagttggtgt cttagtcttt gatctccaca agtctttata gtctaacgac taaatcttct    1920
tcaaggtgta ccttagcaag cagttcgttc ttggaacctt ctgatgctta aggggagtgt    1980
```

-continued

```
gtctaatagc ttttttaatg acctaggttt atttgacggc aatcattatc atcgtacacc      2040
cagaaaaagt ggttagtgga tgaacgtaga ttcttacaaa ctttaccgaa atctacgtta      2100
gagacttgtt tgttccaaac ttcagtatcc acctataatg aggggacaat cactattgat      2160
agttttcgtt ccgaaccggg gtaggatggt atctcatgca tacacactta accgacgct       2220
ttcttggagt agaaccaact accacctacg taccctcagt aacgttggaa gtatgtgttc      2280
ttgacggttc cagaacctag taaagttagt gctttagtta taattctctc caccacatcg      2340
atgacaatga cctctttttt aaccacactt ttattacaac gaccgaccac cactggatta      2400
tctcagttac ccacttggtt tgcaaacccg cctgcggcta aatgtagtgt aagagccatt      2460
aatgccaaca aactaacagc ttgcatgacc aagactacat tccagaaaaa acaatagggt      2520
actataatac atacttgtat cttccttata agaatagtag ttcgttgagt agatattact      2580
ataagaagg tgctttcaag cagataaata gtctgcgcgg tacagacatg ttataaacaa       2640
tggattaagc cagtagtcca tataggttct tgtatctgat atacacctgg tttggcttgg      2700
acaattcgtt caagaacctt tgtttcttac taaacggcag gccttaacga agcaagaaag      2760
aaagtagaaa gagaaatgtt aaaggttaaa aggggatgtc cttaattaac ctcccatgtt      2820
cgctcatctt tacactgtat actgaatgga tagacacaaa atcatatcaa aaaaaaagac      2880
atcatattaa gtgaaaatgt gattaaaaaa gcggaaaaag agaatttctc gattaaagat      2940
attggaagtc gccaatatgg tttatatttt ttaccttcct tttgtttgtc attctttatt      3000
cgcgttgtcg tgcaatcaag tggtaaccta aggttgtaaa gttttaaatt agattaccgt      3060
tctctatagt gtaaaaactg gcataaaaat ctttcaacac cgcgacattt attactactc      3120
cgtcctttta acaatagacg aacctgaagt tggcatgcgt aactccctgg ccttagttgg      3180
ctgagattaa gtaatatata aggtgacgat ggtggacctt acaactttca tacaaagagg      3240
atcgtttttaa ttttgggtag gcacttactt cgcaatgatt gatattattg accatcgaaa      3300
cagtgagcat ggtccttttc acttctaatt tgacttaaaa ttt                        3343
```

<210> SEQ ID NO 22
<211> LENGTH: 1900
<212> TYPE: DNA
<213> ORGANISM: Saccharomyces cerevisiae
<220> FEATURE:
<221> NAME/KEY: CDS
<222> LOCATION: (813)...(1853)

<400> SEQUENCE: 22

```
ttctactact ccacgtacaa aaagagcac gctgctttat ttatactttt gtgccacaag        60
aatgatcaac atcaacataa atatcaacta gtatctgcaa cacatctgct ccacggaact      120
aaacccgttg agcagtgccc cgtggaaacg taaactatcg caaattggga ttaacaagcc      180
aaaaacagcc aagcaagatt cacgaaaccg cgcctcgttt ggaccccgaa ggcccattta      240
acggccggcc gttacaagca agatcggcag agcaaaccac tccccagcac cacagcacat      300
cactgcacga gcaacaataa ctagaacatg gcagatagcg aggataccctc tgtgatcctg     360
cagggcatcg acacaatcaa cagcgtggag ggcctggaag aagatggtta cctcagcgac      420
gaggacacgt cactcagcaa cgagctcgca gatgcacagc gtcaatggga agagtcgctg      480
caacagttga acaagctgct caactgggtc ctgctgcccc tgctgggcaa gtatataggt      540
aggagaatgg ccaagactct atggagtagg ttcattgaac actttgtata agtgtttgtt      600
gtttatgtat ccgcatatag cagttataac agataaatgg cacttttcgc acacccgttg      660
```

```
ttttatctcc gatagtacgt gggcctttat ttatggtcgt ttaacgaaag aacggcatct        720
tgaattgagc aggtatttaa aagataggac gagaaacaag cacatgatct gtgtcgaaaa        780
aaagtagcaa agagaaaaag taggaggata gg atg aac agg aaa gta gct atc          833
                                    Met Asn Arg Lys Val Ala Ile
                                     1               5 gta acg ggt act aat agt aat ctt ggt ctg aac att gtg ttc cgt ctg          881
Val Thr Gly Thr Asn Ser Asn Leu Gly Leu Asn Ile Val Phe Arg Leu
         10                  15                  20 att gaa act gag gac acc aat gtc aga ttg acc att gtg gtg act tct          929
Ile Glu Thr Glu Asp Thr Asn Val Arg Leu Thr Ile Val Val Thr Ser
     25                  30                  35 aga acg ctt cct cga gtg cag gag gtg att aac cag att aaa gat ttt          977
Arg Thr Leu Pro Arg Val Gln Glu Val Ile Asn Gln Ile Lys Asp Phe
 40                  45                  50                  55 tac aac aaa tca ggc cgt gta gag gat ttg gaa ata gac ttt gat tat         1025
Tyr Asn Lys Ser Gly Arg Val Glu Asp Leu Glu Ile Asp Phe Asp Tyr
                 60                  65                  70 ctg ttg gtg gac ttc acc aac atg gtg agt gtc ttg aac gca tat tac         1073
Leu Leu Val Asp Phe Thr Asn Met Val Ser Val Leu Asn Ala Tyr Tyr
             75                  80                  85 gac atc aac aaa aag tac agg gcg ata aac tac ctt ttc gtg aat gct         1121
Asp Ile Asn Lys Lys Tyr Arg Ala Ile Asn Tyr Leu Phe Val Asn Ala
         90                  95                 100 gcg caa ggt atc ttt gac ggt ata gat tgg atc gga gcg gtc aag gag         1169
Ala Gln Gly Ile Phe Asp Gly Ile Asp Trp Ile Gly Ala Val Lys Glu
     105                 110                 115 gtt ttc acc aat cca ttg gag gca gtg aca aat ccg aca tac aag ata         1217
Val Phe Thr Asn Pro Leu Glu Ala Val Thr Asn Pro Thr Tyr Lys Ile
120                 125                 130                 135 caa ctg gtg ggc gtc aag tct aaa gat gac atg ggg ctt att ttc cag         1265
Gln Leu Val Gly Val Lys Ser Lys Asp Asp Met Gly Leu Ile Phe Gln
                 140                 145                 150 gcc aat gtg ttt ggt ccg tac tac ttt atc agt aaa att ctg cct caa         1313
Ala Asn Val Phe Gly Pro Tyr Tyr Phe Ile Ser Lys Ile Leu Pro Gln
             155                 160                 165 ttg acc agg gga aag gct tat att gtt tgg att tcg agt att atg tcc         1361
Leu Thr Arg Gly Lys Ala Tyr Ile Val Trp Ile Ser Ser Ile Met Ser
         170                 175                 180 gat cct aag tat ctt tcg ttg aac gat att gaa cta cta aag aca aat         1409
Asp Pro Lys Tyr Leu Ser Leu Asn Asp Ile Glu Leu Leu Lys Thr Asn
     185                 190                 195 gcc tct tat gag ggc tcc aag cgt tta gtt gat tta ctg cat ttg gcc         1457
Ala Ser Tyr Glu Gly Ser Lys Arg Leu Val Asp Leu Leu His Leu Ala
200                 205                 210                 215 acc tac aaa gac ttg aaa aag ctg ggc ata aat cag tat gta gtt caa         1505
Thr Tyr Lys Asp Leu Lys Lys Leu Gly Ile Asn Gln Tyr Val Val Gln
                 220                 225                 230 ccg ggc ata ttt aca agc cat tcc ttc tcc gaa tat ttg aat ttt ttc         1553
Pro Gly Ile Phe Thr Ser His Ser Phe Ser Glu Tyr Leu Asn Phe Phe
             235                 240                 245 acc tat ttc ggc atg cta tgc ttg ttc tat ttg gcc agg ctg ttg ggg         1601
Thr Tyr Phe Gly Met Leu Cys Leu Phe Tyr Leu Ala Arg Leu Leu Gly
         250                 255                 260 tct cca tgg cac aat att gat ggt tat aaa gct gcc aat gcc cca gta         1649
Ser Pro Trp His Asn Ile Asp Gly Tyr Lys Ala Ala Asn Ala Pro Val
     265                 270                 275 tac gta act aga ttg gcc aat cca aac ttt gag aaa caa gac gta aaa         1697
Tyr Val Thr Arg Leu Ala Asn Pro Asn Phe Glu Lys Gln Asp Val Lys
```

```
              280                 285                 290                 295
tac ggt tct gct acc tct agg gat ggt atg cca tat atc aag acg cag        1745
Tyr Gly Ser Ala Thr Ser Arg Asp Gly Met Pro Tyr Ile Lys Thr Gln
                    300                 305                 310 gaa ata gac cct act gga atg tct gat gtc ttc gct tat ata cag aag        1793
Glu Ile Asp Pro Thr Gly Met Ser Asp Val Phe Ala Tyr Ile Gln Lys
                315                 320                 325 aag aaa ctg gaa tgg gac gag aaa ctg aaa gat caa att gtt gaa act        1841
Lys Lys Leu Glu Trp Asp Glu Lys Leu Lys Asp Gln Ile Val Glu Thr
            330                 335                 340 aga acc ccc att taatatatct ctgcgtacat atgtatatat atatatgtgt            1893
Arg Thr Pro Ile
    345 gtatata                                                                1900

<210> SEQ ID NO 23
<211> LENGTH: 347
<212> TYPE: PRT
<213> ORGANISM: Saccharomyces cerevisiae

<400> SEQUENCE: 23

Met Asn Arg Lys Val Ala Ile Val Thr Gly Thr Asn Ser Asn Leu Gly
 1               5                  10                  15

Leu Asn Ile Val Phe Arg Leu Ile Glu Thr Glu Asp Thr Asn Val Arg
                20                  25                  30

Leu Thr Ile Val Val Thr Ser Arg Thr Leu Pro Arg Val Gln Glu Val
            35                  40                  45

Ile Asn Gln Ile Lys Asp Phe Tyr Asn Lys Ser Gly Arg Val Glu Asp
         50                  55                  60

Leu Glu Ile Asp Phe Asp Tyr Leu Leu Val Asp Phe Thr Asn Met Val
 65                  70                  75                  80

Ser Val Leu Asn Ala Tyr Tyr Asp Ile Asn Lys Lys Tyr Arg Ala Ile
                85                  90                  95

Asn Tyr Leu Phe Val Asn Ala Ala Gln Gly Ile Phe Asp Gly Ile Asp
               100                 105                 110

Trp Ile Gly Ala Val Lys Glu Val Phe Thr Asn Pro Leu Glu Ala Val
           115                 120                 125

Thr Asn Pro Thr Tyr Lys Ile Gln Leu Val Gly Val Lys Ser Lys Asp
       130                 135                 140

Asp Met Gly Leu Ile Phe Gln Ala Asn Val Phe Gly Pro Tyr Tyr Phe
145                 150                 155                 160

Ile Ser Lys Ile Leu Pro Gln Leu Thr Arg Gly Lys Ala Tyr Ile Val
               165                 170                 175

Trp Ile Ser Ser Ile Met Ser Asp Pro Lys Tyr Leu Ser Leu Asn Asp
           180                 185                 190

Ile Glu Leu Leu Lys Thr Asn Ala Ser Tyr Glu Gly Ser Lys Arg Leu
       195                 200                 205

Val Asp Leu Leu His Leu Ala Thr Tyr Lys Asp Leu Lys Lys Leu Gly
   210                 215                 220

Ile Asn Gln Tyr Val Val Gln Pro Gly Ile Phe Thr Ser His Ser Phe
225                 230                 235                 240

Ser Glu Tyr Leu Asn Phe Phe Thr Tyr Phe Gly Met Leu Cys Leu Phe
               245                 250                 255

Tyr Leu Ala Arg Leu Leu Gly Ser Pro Trp His Asn Ile Asp Gly Tyr
           260                 265                 270
```

```
Lys Ala Ala Asn Ala Pro Val Tyr Val Thr Arg Leu Ala Asn Pro Asn
            275                 280                 285

Phe Glu Lys Gln Asp Val Lys Tyr Gly Ser Ala Thr Ser Arg Asp Gly
        290                 295                 300

Met Pro Tyr Ile Lys Thr Gln Glu Ile Asp Pro Thr Gly Met Ser Asp
305                 310                 315                 320

Val Phe Ala Tyr Ile Gln Lys Lys Lys Leu Glu Trp Asp Glu Lys Leu
                325                 330                 335

Lys Asp Gln Ile Val Glu Thr Arg Thr Pro Ile
            340                 345

<210> SEQ ID NO 24
<211> LENGTH: 1900
<212> TYPE: DNA
<213> ORGANISM: Saccharomyces cerevisiae

<400> SEQUENCE: 24
aagatgatga ggtgcatgtt ttttctcgtg cgacgaaata aatatgaaaa cacggtgttc      60
ttactagttg tagttgtatt tatagttgat catagacgtt gtgtagacga ggtgccttga     120
tttgggcaac tcgtcacggg gcacctttgc atttgatagc gtttaaccct aattgttcgg     180
tttttgtcgg ttcgttctaa gtgctttggc gcggagcaaa cctggggctt ccgggtaaat     240
tgccggccgg caatgttcgt tctagccgtc tcgtttggtg aggggtcgtg gtgtcgtgta     300
gtgacgtgct cgttgttatt gatcttgtac cgtctatcgc tcctatggag acactaggac     360
gtcccgtagc tgtgttagtt gtcgcacctc ccggaccttc ttctaccaat ggagtcgctg     420
ctcctgtgca gtgagtcgtt gctcgagcgt ctacgtgtcg cagttaccct tctcagcgac     480
gttgtcaact tgttcgacga gttgacccag gacgacgggg acgaccgtt catatatcca      540
tcctcttacc ggttctgaga tacctcatcc aagtaacttg tgaaacatat tcacaaacaa     600
caaatacata ggcgtatatc gtcaatattg tctatttacc gtgaaaagcg tgtgggcaac     660
aaaatagagg ctatcatgca cccggaaata aataccagca aattgctttc ttgccgtaga     720
acttaactcg tccataaatt ttctatcctg ctctttgttc gtgtactaga cacagctttt     780
tttcatcgtt tctcttttc atcctcctat cctacttgtc ctttcatcga tagcattgcc      840
catgattatc attagaacca gacttgtaac acaaggcaga ctaactttga ctcctgtggt     900
tacagtctaa ctggtaacac cactgaagat cttgcgaagg agctcacgtc ctccactaat     960
tggtctaatt tctaaaaatg ttgtttagtc cggcacatct cctaaacctt tatctgaaac    1020
taatagacaa ccacctgaag tggttgtacc actcacagaa cttgcgtata atgctgtagt    1080
tgtttttcat gtcccgctat ttgatggaaa agcacttacg acgcgttcca tagaaactgc    1140
catatctaac ctagcctcgc cagttcctcc aaaagtggtt aggtaacctc cgtcactgtt    1200
taggctgtat gttctatgtt gaccacccgc agttcagatt tctactgtac cccgaataaa    1260
aggtccggtt acacaaacca ggcatgatga aatagtcatt ttaagacgga gttaactggt    1320
cccctttccg aatataacaa acctaaagct cataatacag gctaggattc atagaaagca    1380
acttgctata acttgatgat ttctgtttac ggagaatact cccgaggttc gcaaatcaac    1440
taaatgacgt aaaccggtgg atgtttctga acttttttcga cccgtattta gtcatacatc    1500
aagttggccc gtataaatgt tcggtaagga agaggcttat aaacttaaaa aagtggataa    1560
agccgtacga tacgaacaag ataaaccggt ccgacaaccc cagaggtacc gtgttataac    1620
taccaatatt tcgacggtta cggggtcata tgcattgatc taaccggtta ggtttgaaac    1680
```

-continued

```
tctttgttct gcattttatg ccaagacgat ggagatccct accatacggt atatagttct    1740
gcgtccttta tctgggatga ccttacagac tacagaagcg aatatatgtc ttcttctttg    1800
accttaccct gctctttgac tttctagttt aacaactttg atcttggggg taaattatat    1860
agagacgcat gtatacatat atatatatac acacatatat                          1900
```

<210> SEQ ID NO 25
<211> LENGTH: 59
<212> TYPE: DNA
<213> ORGANISM: Saccharomyces cerevisiae

<400> SEQUENCE: 25

```
aggaaagtag ctatcgtaac gggtactaat agtaatcttg gtctcttggc ctcctctag       59
```

<210> SEQ ID NO 26
<211> LENGTH: 59
<212> TYPE: DNA
<213> ORGANISM: Saccharomyces cerevisiae

<400> SEQUENCE: 26

```
tacgcagaga tatattaaat gggggttcta gtttcaacaa tttcgttcag aatgacacg       59
```

<210> SEQ ID NO 27
<211> LENGTH: 62
<212> TYPE: DNA
<213> ORGANISM: Saccharomyces cerevisiae

<400> SEQUENCE: 27

```
ttaacagccg cgcccatcat gcaagatcct gatggtattg acattctctt ggcctcctct       60
ag                                                                      62
```

<210> SEQ ID NO 28
<211> LENGTH: 59
<212> TYPE: DNA
<213> ORGANISM: Saccharomyces cerevisiae

<400> SEQUENCE: 28

```
gcatatcaat tttaacagac ctcgctgaaa gactctgaat cctcgttcag aatgacacg       59
```

<210> SEQ ID NO 29
<211> LENGTH: 429
<212> TYPE: PRT
<213> ORGANISM: Aspergillus nidulans

<400> SEQUENCE: 29

```
Thr Leu Ala Glu Glu Asn Met Thr Leu Phe Ile His Cys Tyr Ser Lys
 1               5                  10                  15

Gly His Glu Asn Leu Gln Val Thr Ala Ile His Ile Leu Cys Asp Met
                20                  25                  30

Leu Ile Ser His Pro Ser Leu Val Ala Pro Val Thr Gln Ala Asp Lys
            35                  40                  45

Glu Thr Val Ala Pro Pro Ala Phe Gln Lys Pro Leu Leu Lys Val Phe
        50                  55                  60

Ser Arg Ala Leu Lys Pro Asn Ser Pro Ala Ser Val Gln Thr Ala Ala
    65                  70                  75                  80

Ala Thr Ala Leu Ser Lys Leu Leu Leu Thr Gly Val Phe Thr Pro Ser
                85                  90                  95

Ala Ala Asn Ile Pro Asp Ala Ile Gln Glu Phe Asn Gln His Ala Ile
               100                 105                 110
```

```
Glu Thr Leu Leu Gln Ser Leu Val Val Ser Phe Phe His Pro Arg Thr
            115                 120                 125

Arg Glu Asn Pro Ala Leu Arg Gln Ala Leu Ala Tyr Phe Phe Pro Val
        130                 135                 140

Tyr Cys His Ser Arg Pro Asp Asn Thr Gln His Met Arg Lys Ile Thr
145                 150                 155                 160

Val Pro Val Ile Arg Thr Ile Leu Asn Ser Ala Glu Glu Tyr Tyr Ser
                165                 170                 175

Leu Glu Ala Glu Glu Asp Ser Asp Gly Asp Ile Asp Glu Ser Val Gly
            180                 185                 190

Glu Lys Glu Leu Lys Ala Leu Met Ser Gly Val Leu Gly Met Leu Ala
        195                 200                 205

Glu Trp Thr Asp Glu Arg Arg Val Ile Gly Leu Gly Gly Glu Arg Val
        210                 215                 220

Leu Ala Gly Gly Leu Ala Ser Ser Asn Val Cys Gly Ile Ile His Leu
225                 230                 235                 240

Gln Leu Ile Lys Asp Ile Leu Glu Arg Val Leu Gly Ile Ser Glu Gly
                245                 250                 255

Ser Asn Arg Cys Ser Lys Gln Gln Arg Lys Leu Leu Phe Ser Leu Met
            260                 265                 270

Ser Lys Leu Tyr Ile Ala Pro Pro Thr Ala Leu Ser Arg Ser Ala Ser
        275                 280                 285

Gln Ala Pro Glu Asp Asp Ser Phe Arg Ser Ser Val Arg Ser Ser His
        290                 295                 300

Gly Glu Leu Asn Pro Glu Asn Leu Ala Leu Ala Gln Glu Val Lys Glu
305                 310                 315                 320

Leu Leu Asp Gln Thr Ile Glu Gly Val Ala Ala Asp Ala Ala Ser
                325                 330                 335

Arg Asn Ala Leu Val Lys Val Lys Asn Val Val Leu Lys Leu Leu Ala
            340                 345                 350

Ala Pro Met Arg Pro Ser Ser Ala Arg Gly Arg Glu Ser Ser Val Glu
        355                 360                 365

Ser Asp Ile Gly Ser Val Arg Ser Ser Arg Ser Val Arg Pro Ser Val
370                 375                 380

Glu Pro Gly Phe Gly Arg Arg Gly Val Ser Val Glu Pro Ser Ile Met
385                 390                 395                 400

Glu Glu Asp Glu Asn Glu Asp Ser Arg Ala Thr Leu Asp Ser Arg Met
            405                 410                 415

Thr Val Ile Lys Glu Glu Asp Ala Asp Ala Met Glu Glu
                420                 425

<210> SEQ ID NO 30
<211> LENGTH: 147
<212> TYPE: PRT
<213> ORGANISM: Aspergillus nidulans

<400> SEQUENCE: 30

Leu Leu Ser Pro Pro Leu Val Arg Ala Thr Val Ile Phe Pro Ser Ser
  1               5                  10                  15

Ser Ser Cys Arg Ser Arg Leu Lys Tyr Ser Val Ser Cys Ser Asp Leu
            20                  25                  30

Gln Leu Leu Arg Ala Asp Thr Leu His Ile Ser Ala Ile Met Thr Glu
        35                  40                  45

Ser Thr Gln Glu Gln Gly Asn Asp Gly Gln Arg Met Pro Pro Ala Pro
    50                  55                  60
```

```
Ala Thr Pro Val Glu Asp Tyr Val Phe Pro Tyr Arg Leu Lys Arg
 65                  70                  75                  80

Val Met Asp Asp Pro Glu Lys Thr Pro Leu Leu Ile Ala Cys Gly
                 85                  90                  95

Ser Phe Ser Pro Ile Thr Phe Leu His Leu Arg Met Phe Glu Met Ala
                100                 105                 110

Ala Asp Tyr Val Lys Leu Ser Thr Asp Phe Glu Ile Ile Gly Gly Tyr
            115                 120                 125

Leu Ser Pro Val Ser Asp Ala Tyr Arg Lys Ala Gly Leu Ala Ser Ala
        130                 135                 140

Asn His Arg
145
```

<210> SEQ ID NO 31
<211> LENGTH: 91
<212> TYPE: PRT
<213> ORGANISM: Aspergillus nidulans

<400> SEQUENCE: 31

```
Ile Ala Met Cys Gln Arg Ala Val Asp Gln Thr Ser Asp Trp Met Met
 1               5                  10                  15

Val Asp Thr Trp Glu Pro Met His Lys Glu Tyr Gln Pro Thr Ala Ile
                20                  25                  30

Val Leu Asp His Phe Asp Tyr Glu Ile Asn Thr Val Arg Lys Gly Ile
            35                  40                  45

Asp Thr Gly Lys Gly Thr Arg Lys Arg Val Gln Val Leu Leu Ala
        50                  55                  60

Gly Ala Asp Leu Val His Thr Met Ser Thr Pro Gly Val Trp Ser Glu
 65                  70                  75                  80

Lys Asp Leu Asp His Ile Leu Gly Gln Tyr Gly
                85                  90
```

<210> SEQ ID NO 32
<211> LENGTH: 92
<212> TYPE: PRT
<213> ORGANISM: Aspergillus nidulans

<400> SEQUENCE: 32

```
Thr Phe Ile Val Glu Arg Ser Gly Thr Asp Ile Asp Glu Ala Leu Ala
 1               5                  10                  15

Ala Leu Gln Pro Trp Lys Lys Asn Ile His Val Ile Gln Gln Leu Ile
                20                  25                  30

Gln Asn Asp Val Ser Ser Thr Lys Ile Arg Leu Phe Leu Arg Arg Asp
            35                  40                  45

Met Ser Val Arg Tyr Leu Ile Pro Asp Pro Val Ile Glu Tyr Ile Tyr
        50                  55                  60

Glu Asn Asn Leu Tyr Met Asp Asp Gly Thr Thr Gln Pro Thr Ala Asp
 65                  70                  75                  80

Lys Gly Lys Thr Arg Glu Glu Pro Ala Pro Ser Asn
                85                  90
```

<210> SEQ ID NO 33
<211> LENGTH: 69
<212> TYPE: PRT
<213> ORGANISM: Aspergillus nidulans

<400> SEQUENCE: 33

-continued

```
Ala Ala Lys Ala Ala Leu Arg Arg Lys Lys Val His Glu Lys Asn Leu
 1               5                  10                  15

Glu Gln Thr Gln Ala Gln Ile Val Gln Leu Glu Gln Gln Ile Tyr Ser
                20                  25                  30

Ile Glu Ala Ala Asn Ile Asn His Glu Thr Leu Ala Ala Met Lys Ala
            35                  40                  45

Ala Gly Ala Ala Met Glu Lys Ile His Asn Gly Met Thr Val Glu Gln
        50                  55                  60

Val Asp Glu Thr Met
 65

<210> SEQ ID NO 34
<211> LENGTH: 69
<212> TYPE: PRT
<213> ORGANISM: Aspergillus nidulans

<400> SEQUENCE: 34

Asp Lys Leu Arg Glu Gln Gln Ala Ile Asn Asp Glu Ile Ala Ile Ala
 1               5                  10                  15

Ile Thr Asn Pro Gly Phe Gly Glu Gln Val Asp Glu Glu Asp Leu Glu
                20                  25                  30

Ala Glu Leu Glu Gly Met Glu Gln Glu Ala Met Asp Glu Arg Met Leu
            35                  40                  45

His Thr Gly Thr Val Pro Val Ala Asp Gln Leu Asn Arg Leu Pro Ala
        50                  55                  60

Pro Ala Asn Ala Glu
 65

<210> SEQ ID NO 35
<211> LENGTH: 26
<212> TYPE: PRT
<213> ORGANISM: Aspergillus nidulans

<400> SEQUENCE: 35

Pro Ala Lys Ala Lys Gln Lys Ala Glu Glu Glu Asp Glu Glu Ala Glu
 1               5                  10                  15

Leu Glu Lys Leu Arg Ala Glu Met Ala Met
                20                  25
```

What is claimed is:

1. An isolated nucleic acid encoding an AN97 polypeptide comprising the amino acid sequence set forth as SEQ ID NOs: 2 or 29, as depicted in FIG. 1.

2. An isolated nucleic acid consisting essentially of a sequence selected from the group consisting of:
   (a) SEQ ID NO: 1, as depicted in FIG. 1, or degenerate variants thereof that encode the same amino acid sequence as SEQ ID NO: 1 encodes;
   (b) SEQ ID NO: 1, as depicted in FIG. 1, or degenerate variants thereof that encode the same amino acid sequence as SEQ ID NO: 1 encodes, wherein T is replaced by U;
   (c) SEQ ID NO: 3; and
   (d) SEQ ID NO: 3, wherein T is replaced by U.

3. An isolated nucleic acid from Aspergillus consisting essentially of the nucleic acid sequence set forth as SEQ ID NO:1, and encoding an AN97 polypeptide.

4. An isolated nucleic acid molecule, said molecule comprising the cDNA sequence contained within American Type Culture Collection (ATCC) accession number 209473.

5. A vector comprising the nucleic acid of claim 1.

6. A vector comprising the nucleic acid of claim 2.

7. An expression vector comprising the nucleic acid of claim 1 operably linked to a nucleotide sequence regulatory element that controls expression of said nucleic acid.

8. An expression vector comprising the nucleic acid of claim 2 operably linked to a nucleotide sequence regulatory element that controls expression of said nucleic acid.

9. A genetically engineered host cell comprising the nucleic acid of claim 1.

10. A genetically engineered host cell comprising the nucleic acid of claim 2.

11. The host cell of claim 9, wherein the cell is a yeast or bacterium.

12. The host cell of claim 10, wherein the cell is a yeast or bacterium.

13. A genetically engineered host cell comprising the nucleic acid of claim 1 operably linked to a nucleotide sequence regulatory element that controls expression of the nucleic acid in the host cell.

14. The host cell of claim 13, wherein the cell is a yeast or bacterium.

15. A genetically engineered host cell comprising the nucleic acid of claim 2 operably linked to a nucleotide sequence regulatory element that controls expression of the nucleic acid in the host cell.

16. The host cell of claim 15, wherein the cell is a yeast or bacterium.

17. A method for identifying an antifungal agent, the method comprising:
   (a) contacting a nucleic acid encoding an AN97 polypeptide with a test compound, wherein the AN97 polypeptide has the amino acid sequence set forth as SEQ ID NOs: 2 and 29;
   (b) detecting binding of the test compound to the nucleic acid; and
   (c) determining whether a test compound that binds to the nucleic acid inhibits growth of fungi, relative to growth of fungi cultured in the absence of the test compound that binds to the nucleic acid, wherein inhibition of growth is an indication that the test compound is an antifungal agent.

18. The method of claim 17, wherein the test compound is selected from the group consisting of polypeptides, small molecules, ribonucleic acids, and deoxyribonucleic acids.

19. The method of claim 17, wherein the test compound is an antisense oligonucleotide.

20. The method of claim 17, wherein the test compound is a ribozyme.

21. A method for identifying an antifungal agent, the method comprising:
   (a) contacting the nucleic acid of claim 2 with a test compound;
   (b) detecting binding of the test compound to the nucleic acid; and
   (c) determining whether a test compound that binds to the nucleic acid inhibits growth of fungi, relative to growth of fungi cultured in the absence of the test compound that binds to the nucleic acid, wherein inhibition of growth indicates that the test compound is an antifungal agent.

22. The method of claim 21, wherein the test compound is selected from the group consisting of polypeptides, small molecules, ribonucleic acids, and deoxyribonucleic acids.

23. The method of claim 21, wherein the test compound is an antisense molecule.

24. The method of claim 21, wherein the test compound is a ribozyme.

\* \* \* \* \*